United States Patent
Pei

(10) Patent No.: US 11,859,019 B2
(45) Date of Patent: *Jan. 2, 2024

(54) BICYCLIC PEPTIDYL INHIBITOR OF TUMOR NECROSIS FACTOR-ALPHA

(71) Applicant: Ohio State Innovation Foundation, Columbus, OH (US)

(72) Inventor: Dehua Pei, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 152 days.

This patent is subject to a terminal disclaimer.

(21) Appl. No.: 17/136,578

(22) Filed: Dec. 29, 2020

(65) Prior Publication Data

US 2021/0115088 A1  Apr. 22, 2021

Related U.S. Application Data

(63) Continuation of application No. 16/462,914, filed as application No. PCT/US2017/062945 on Nov. 22, 2017, now Pat. No. 10,913,773.

(60) Provisional application No. 62/425,471, filed on Nov. 22, 2016.

(51) Int. Cl.
| | | |
|---|---|---|
| *C07K 7/56* | (2006.01) | |
| *A61P 29/00* | (2006.01) | |
| *A61K 38/00* | (2006.01) | |

(52) U.S. Cl.
CPC ............... *C07K 7/56* (2013.01); *A61P 29/00* (2018.01); *A61K 38/00* (2013.01)

(58) Field of Classification Search
CPC ............ C07K 7/56; A61P 29/00; A61K 38/00
See application file for complete search history.

(56) References Cited

U.S. PATENT DOCUMENTS

| | | | |
|---|---|---|---|
| 5,804,558 | A | 9/1998 | Lehrer et al. |
| 6,864,355 | B1 | 3/2005 | May et al. |
| 6,960,648 | B2 | 11/2005 | Bonny |
| 7,850,949 | B2 | 12/2010 | Fang |
| 9,868,767 | B2 | 1/2018 | Pei et al. |
| 10,501,496 | B2 | 12/2019 | Pei et al. |
| 10,626,147 | B2 | 4/2020 | Pei et al. |
| 10,738,093 | B2 | 8/2020 | Qian et al. |
| 10,815,276 | B2 | 10/2020 | Pei |
| 10,913,773 | B2 * | 2/2021 | Pei .................. C07K 7/56 |
| 11,225,506 | B2 | 1/2022 | Pei |
| 11,339,192 | B2 * | 5/2022 | Pei .................. A61P 35/00 |
| 11,351,222 | B2 * | 6/2022 | Pei .................. C07K 14/001 |
| 11,352,394 | B2 * | 6/2022 | Pei .................. C07K 14/001 |
| 11,576,946 | B2 * | 2/2023 | Pei .................. C07K 16/289 |
| 2002/0035243 | A1 | 3/2002 | Imfeld |
| 2002/0120100 | A1 | 8/2002 | Bonny |
| 2003/0032594 | A1 | 2/2003 | Bonny |
| 2004/0014669 | A1 | 1/2004 | Selsted et al. |
| 2005/0107289 | A1 | 5/2005 | Ghadiri |
| 2007/0041904 | A1 | 2/2007 | Jiang et al. |
| 2010/0292148 | A1 | 11/2010 | Krippner et al. |
| 2013/0085736 | A1 | 4/2013 | Reihsen et al. |
| 2014/0294942 | A1 | 10/2014 | French et al. |
| 2015/0297742 | A1 | 10/2015 | Strieker et al. |
| 2016/0115202 | A1 | 4/2016 | Pei et al. |
| 2016/0235807 | A1 | 8/2016 | Shailubhai |
| 2016/0271216 | A1 | 9/2016 | Kemper et al. |
| 2017/0190743 | A1 | 7/2017 | Pei et al. |
| 2017/0355730 | A1 | 12/2017 | Pei et al. |
| 2018/0030094 | A1 | 2/2018 | Pei et al. |
| 2019/0282654 | A1 | 9/2019 | Pei et al. |
| 2019/0284240 | A1 | 9/2019 | Pei et al. |
| 2019/0309020 | A1 | 10/2019 | Pei et al. |
| 2020/0291070 | A1 | 9/2020 | Pei et al. |

FOREIGN PATENT DOCUMENTS

| | | | |
|---|---|---|---|
| EP | 2420255 | 2/2012 | |
| JP | 2010526091 A | 7/2010 | |
| WO | 2007055578 A1 | 5/2007 | |
| WO | 2008/134761 A2 | 11/2008 | |
| WO | 2009098450 | 8/2009 | |
| WO | 2001/052875 A1 | 7/2010 | |
| WO | 2014053882 | 4/2014 | |
| WO | 2014190313 A2 | 11/2014 | |
| WO | WO2014/190257 | * 11/2014 | ............. A61K 38/12 |
| WO | 2015051030 | 4/2015 | |
| WO | 2015179434 A1 | 11/2015 | |
| WO | 2015179691 | 11/2015 | |
| WO | 2016054510 | 4/2016 | |

(Continued)

OTHER PUBLICATIONS

Final Office Action issued in U.S. Appl. No. 17/053,684 dated Aug. 5, 2022.
Communication pursuant to Article 94(3) EPC issued in European Application 17870556.2 dated Sep. 1, 2022.
Restriction Requirement issued in U.S. Appl. No. 17/538,330 dated Oct. 14, 2022.
Almarsson, Örn, and Michael J. Zaworotko. "Crystal engineering of the composition of pharmaceutical phases. Do pharmaceutical co-crystals represent a new path to improved medicines?" Chemical communications 17 (2004): 1889-1896.
Alzani, R. et al. "Suramin induces deoligomerization of human tumor necrosis factor alpha." J. Biol. Chem. 268, (1993): 12526-12529.
Angelini, Alessandro, et al. "Bicyclic peptide inhibitor reveals large contact interface with a protease target." ACS chemical biology 7.5 (2012): 817-821.

(Continued)

*Primary Examiner* — Marcela M Cordero Garcia
(74) *Attorney, Agent, or Firm* — Meunier Carlin & Curfman LLC

(57) ABSTRACT

Anticachexin C1 inhibits the TNFα-TNFα receptor interaction. In this work, analogs of anticachexin C1 are disclosed. The resulting bicyclic peptides inhibit TNFα TNFα-induced cell death, NF-κB activation, and c-Jun N-terminal kinase (JNK) signaling in cultured mammalian cells. Methods of using the bicyclic peptide anticachexin C1 analogs to treat cancer, inflammatory disorders and immune disorders are also described.

25 Claims, 9 Drawing Sheets

Specification includes a Sequence Listing.

(56) References Cited

FOREIGN PATENT DOCUMENTS

| WO | 2017109076 | 6/2017 |
|----|------------|--------|
| WO | 2017114440 | 7/2017 |
| WO | 2018098231 A1 | 5/2018 |

OTHER PUBLICATIONS

Appelbaum, Jacob S., et al. "Arginine topology controls escape of minimally cationic proteins from early endosomes to the cytoplasm." Chemistry & biology 19.7 (2012): 819-830.
Ardi, V. C., et al., "Macrocycles that inhibit the binding between heat shock protein 90 and TPR-containing proteins." ACS Chem. Biol. 6, (2011): 1357-1366.
Baud, Véronique, and Michael Karin. "Is NF-κB a good target for cancer therapy? Hopes and pitfalls." Nature reviews Drug discovery 8.1 (2009): 33.
Beste, G. et al. "Small antibody-like proteins with prescribed ligand specificities derivedfrom the lipocalin fold." Proc. Natl. Acad. Sci. USA 96, (1999): 1898-1903.
Beutler, B. et al. "Purification of cachectin, a lipoprotein-lipase suppressing hormone secreted by endotoxin-induced RAW 264.7 cells." J. Exp. Med. 161, (1985): 984-995.
Birts, C. N. et al. "A cyclic peptide inhibitor of C-terminal binding protein dimerization links metabolism with mitotic fidelity in breast cancer cells." Chem. Sci., 4, (2013): 3046-3057.
Buller, F., et al. "Discovery of TNF inhibitors from a DNA-encoded chemical library based on Diels-Alder cycloaddition." Chem. Biol. 16, (2009): 1075-1086.
Chan, D. S. et al. "Structure-based discovery of natural-product-like TNF-a inhibitors." Angew. Chem. Int. Ed. Engl. 49, (2010): 2860-2864.
Chatterjee, Jayanta, et al. "N-methylation of peptides: a new perspective in medicinal chemistry." Accounts of chemical research 41.10 (2008): 1331-1342.
Chen et al. "Bicyclic Peptide Ligands Pulled out of Cysteine-Rich Peptide Libraries," JACS, 135(17), (2013): 6562-6569.
Chen, G. & Goeddel, D. V. "TNF-R1 signaling: a beautiful pathway." Science 296, (2002): 1634-1635.
Chen, S., et al., "Structurally diverse cyclization linkers impose different backbone conformations in bicyclic peptides." ChemBioChem. 13, (2012): 1032-1038.
Chen, X., Tan, P. H., Zhang, Y. & Pei, D. "On-bead screening of combinatorial libraries: Reduction of nonspecific binding by decreasing surface ligand density." J. Comb. Chem. 11, (2009): 604-611.
Cheng, Seng H., et al. "Defective intracellular transport and processing of CFTR is the molecular basis of most cystic fibrosis." Cell 63.4 (1990): 827-834.
Choi, H., et al., "Discovery of the inhibitors of tumor necrosis factor alpha with structure-based virtual screening." Bioorg. Med. Chem. Lett. 20, (2010): 6195- 6198.
Cildir, Gökhan, Kee Chung Low, and Vinay Tergaonkar. "Noncanonical NF-κB signaling in health and disease." Trends in molecular medicine 22.5 (2016): 414-429.
Cochran, Andrea G., Nicholas J. Skelton, and Melissa A. Starovasnik. "Tryptophan zippers: Stable, monomeric β-hairpins." Proceedings of the National Academy of Sciences 98.10 (2001): 5578-5583.
Cooley, Christina B., et al. "Oligocarbonate molecular transporters: oligomerization-based syntheses and cell-penetrating studies." Journal of the American Chemical Society 131.45 (2009): 16401-16403.
Craik, David J., et al. "The future of peptide-based drugs." Chemical biology & drug design 81.1 (2013): 136-147.
Cushing, Patrick R., et al. "A Stabilizing Influence: CAL PDZ Inhibition Extends the Half-Life of ΔF508-CFTR." Angewandte Chemie International Edition 49.51 (2010): 9907-9911.
Dai, Simon, et al. "The IκB kinase (IKK) inhibitor, NEMO-binding domain peptide, blocks osteoclastogenesis and bone erosion in inflammatory arthritis." Journal of Biological Chemistry 279.36 (2004): 37219-37222.

Davé, Shaival H., et al. "Amelioration of chronic murine colitis by peptide-mediated transduction of the IκB kinase inhibitor NEMO binding domain peptide." The Journal of Immunology 179.11 (2007): 7852-7859.
Delfín, Dawn A., et al. "Improvement of cardiac contractile function by peptide-based inhibition of NF-κB in the utrophin/dystrophin-deficient murine model of muscular dystrophy." Journal of translational medicine 9.1 (2011): 68.
Deshayes, Sebastien, et al. "Cell-penetrating peptides: tools for intracellular delivery of therapeutics." Cellular and Molecular Life Sciences CMLS 62.16 (2005): 1839-1849.
Desimmie, B. A. et al. "Phage Display-directed Discovery of LEDGF/p75 Binding Cyclic Peptide Inhibitors of HIV Replication." Mol. Therapy 20, (2012): 2064-2075.
Dewan, V. et al. "Cyclic peptide inhibitors of HIV-I capsid-human lysyl-tRNA synthetase interaction." ACS Chem. Biol. 7, (2012):761-769.
Dong et al., A Photocontrolled β-Hairpin Peptide. Chemistry—A European Journal. 2006, 12 (4): 1114-1120.
Duchardt, Falk, et al. "A comprehensive model for the cellular uptake of cationic cell-penetrating peptides." Traffic 8.7 (2007): 848-866.
Eguchi, Akiko, et al. "Protein transduction domain of HIV-1 Tat protein promotes efficient delivery of DNA into mammalian cells." Journal of Biological Chemistry 276.28 (2001): 26204-26210.
Eisenberg, David, Robert M. Weiss, and Thomas C. Terwilliger. "The hydrophobic moment detects periodicity in protein hydrophobicity." Proceedings of the National Academy of Sciences 81.1 (1984): 140-144.
El Andaloussi, Samir, et al. "Design of a peptide-based vector, PepFect6, for efficient delivery of siRNA in cell culture and systemically in vivo." Nucleic acids research 39.9 (2011): 3972-3987.
El-Sayed, Ayman, Shiroh Futaki, and Hideyoshi Harashima. "Delivery of macromolecules using arginine-rich cell-penetrating peptides: ways to overcome endosomal entrapment." The AAPS journal 11.1 (2009): 13-22.
Engelman, D. M., T. A. Steitz, and A. Goldman. "Identifying nonpolar transbilayer helices in amino acid sequences of membrane proteins." Annual review of biophysics and biophysical chemistry 15.1 (1986): 321-353.
Esposito, E. & Cuzzocrea, S. "TNF-alpha as a therapeutic target in inflammatory diseases, ischemia-reperfusion injury and trauma." Curr. Med. Chem. 16, (2009): 3152-3167.
Ferrari, Aldo, et al. "Caveolae-mediated internalization of extracellular HIV-1 tat fusion proteins visualized in real time." Molecular therapy 8.2 (2003): 284-294.
Fittipaldi, Antonio, et al. "Cell membrane lipid rafts mediate caveolar endocytosis of HIV-1 Tat fusion proteins." Journal of Biological Chemistry 278.36 (2003): 34141-34149.
Fosgerau, Keld, and Torsten Hoffmann. "Peptide therapeutics: current status and future directions." Drug discovery today 20.1 (2015): 122-128.
Frankel, Alan D., and Carl O. Pabo. "Cellular uptake of the tat protein from human immunodeficiency virus." Cell 55.6 (1988): 1189-1193.
Furka, A., et al. "General method for rapid synthesis of multicomponent peptide mixtures." Int. J. Pep. Prat. Res. 37, (1991): 487-493.
Futaki, Shiroh. "Membrane-permeable arginine-rich peptides and the translocation mechanisms." Advanced drug delivery reviews 57.4 (2005): 547-558.
Gaurnier-Hausser, Anita, et al. "NEMO-binding domain peptide inhibits constitutive NF-κB activity and reduces tumor burden in a canine model of relapsed, refractory diffuse large B-cell lymphoma." Clinical Cancer Research 17.14 (2011): 4661-4671.
Gotoh, Yusuke, et al. "A homogeneous time-resolved fluorescence-based high-throughput screening system for discovery of inhibitors of IKKβ-NEMO interaction." Analytical biochemistry 405.1 (2010): 19-27.
Goun, Elena A., et al. "Molecular transporters: synthesis of oligoguanidinium transporters and their application to drug delivery and real-time imaging." Chem Bio Chem 7.10 (2006): 1497-1515.

(56) References Cited

OTHER PUBLICATIONS

Green, Maurice, and Paul M. Loewenstein. "Autonomous functional domains of chemically synthesized human immunodeficiency virus tat trans-activator protein." Cell 55.6 (1988): 1179-1188.
Guo, Bingqian, et al. "Protein engineering of the N-terminus of NEMO: structure stabilization and rescue of IKKβ binding." Biochemistry 53.43 (2014): 6776-6785.
Gupta, Bhawna, Tatiana S. Levchenko, and Vladimir P. Torchilin. "Intracellular delivery of large molecules and small particles by cell-penetrating proteins and peptides." Advanced drug delivery reviews 57.4 (2005): 637-651.
Gupta, Subash C., et al. "Inhibiting NF-κB activation by small molecules as a therapeutic strategy." Biochimica et Biophysica Acta (BBA)-Gene Regulatory Mechanisms 1799.10-12 (2010): 775-787.
Hancock R., et al., Peptide inhibitors of the Keap1-Nrf2 protein-protein interaction. Free Radic. Biol. Med. 52, (2012):444-451.
He, M. M. et al. "Small-molecule inhibition of TNF-a." Science 310, (2005): 1022-1025.
Heinis, C., Rutherford, T., Freund, S. & Winter, G. "Phage-encoded combinatorial chemical libraries based on bicyclic peptides." Nat. Chem. Biol. 5, (2009): 502-507.
Herce, H. D., et al. "Arginine-rich peptides destabilize the plasma membrane, consistent with a pore formation translocation mechanism of cell-penetrating peptides." Biophysical journal 97.7 (2009): 1917-1925.
Herce, Henry D., and Angel E. Garcia. "Molecular dynamics simulations suggest a mechanism for translocation of the HIV-1 TAT peptide across lipid membranes." Proceedings of the National Academy of Sciences 104.52 (2007): 20805-20810.
Herndon, Thomas M., et al. "US Food and Drug Administration approval: carfilzomib for the treatment of multiple myeloma." Clinical cancer research 19.17 (2013): 4559-4563.
Herrington, Felicity D., Ruaidhri J. Carmody, and Carl S. Goodyear. "Modulation of NF-κB signaling as a therapeutic target in autoimmunity." Journal of biomolecular screening 21.3 (2016): 223-242.
Hintersteiner, M. et al. "Single bead labeling method for combining confocal fluorescence on-bead screening and solution validation of tagged one-bead one-compound libraries." Chem. Biol. 16, (2009): 724-735.
Hirose, Hisaaki, et al. "Transient focal membrane deformation induced by arginine-rich peptides leads to their direct penetration into cells." Molecular Therapy 20.5 (2012): 984-993.
Hopp, Thomas P., and Kenneth R. Woods. "Prediction of protein antigenic determinants from amino acid sequences." Proceedings of the National Academy of Sciences 78.6 (1981): 3824-3828.
Houghten, R. A et al. "Generation and use of synthetic peptide combinatorial libraries for basic research and drug discovery." Nature 354, (1991): 84-86.
Hoyer, J. A. N., and Ines Neundorf. "Peptide vectors for the nonviral delivery of nucleic acids." Accounts of chemical research 45.7 (2012): 1048-1056.
Hu, B. H., Jones, M. R. & Messersmith, P. B. "Method for screening and MALDI-TOF MS sequencing of encoded combinatorial libraries." Anal. Chem. 79, (2007): 7275-7285.
Huang, H-C., Truyen Nguyen, and Cecil B. Pickett. "Regulation of the antioxidant response element by protein kinase C-mediated phosphorylation of NF-E2-related factor 2." Proceedings of the National Academy of Sciences 97.23 (2000): 12475-12480.
Inoyama, Daigo, et al. "Optimization of fluorescently labeled Nrf2 peptide probes and the development of a fluorescence polarization assay for the discovery of inhibitors of Keap1-Nrf2 interaction." Journal of biomolecular screening 17.4 (2012): 435-447.
Ishii, Tetsuro, et al. "Transcription factor Nrf2 coordinately regulates a group of oxidative stress-inducible genes in macrophages." Journal of Biological Chemistry 275.21 (2000): 16023-16029.
Janin, J. O. E. L. "Surface and inside volumes in globular proteins." Nature 277, 5696 (1979): 491.
Jeong, Ji Hoon, et al. "siRNA conjugate delivery systems." Bioconjugate chemistry 20.1 (2008): 5-14.

Jimi, Eijiro, et al. "Selective inhibition of NF-κB blocks osteoclastogenesis and prevents inflammatory bone destruction in vivo." Nature medicine 10.6 (2004): 617.
Joo, S. H., Xiao, Q., Ling, Y., Gopishetty, B. & Pei, D. "High-throughput sequence determination of cyclic peptide library members by partial Edman degradation/mass spectrometry." J. Am. Chem. Soc. 128, (2006): 13000-13009.
Josephson, Lee, et al. "High-efficiency intracellular magnetic labeling with novel superparamagnetic-Tat peptide conjugates." Bioconjugate chemistry 10.2 (1999): 186-191.
Kansanen, Emilia, et al. "The Keap1-Nrf2 pathway: mechanisms of activation and dysregulation in cancer." Redox biology 1.1 (2013): 45-49.
Kaplan, Ian M., Jehangir S. Wadia, and Steven F. Dowdy. "Cationic TAT peptide transduction domain enters cells by macropinocytosis." Journal of Controlled Release 102.1 (2005): 247-253.
Kawakami, M., & Cerami, A. Studies of endotoxin-induced decrease in lipoprotein-lipase activity. J. Exp. Med. 154, (1981): 631-639.
Kerem, Bat-sheva, et al. "Identification of the cystic fibrosis gene: genetic analysis." Science 245.4922 (1989): 1073-1080.
Khabar, K. S., Siddiqui, S. & Armstrong, J. A. "WEHI-13V AR: a stable and sensitive variant of WEHI 164 clone 13 fibrosarcoma for tumor necrosis factor bioassay." Immunol. Lett. 46, (1995): 107-110.
Khakshoor, Omid, and James S. Nowick. "Artificial B-sheets: chemical models of β-sheets." Current opinion in chemical biology 12.6 (2008): 722-729.
Kimber, Matthew S., et al. "Structural basis for specificity switching of the Src SH2 domain." Molecular cell 5.6 (2000): 1043-1049.
Kodadek, T. & Bachhawat-Sikder, K. "Optimized protocols for the isolation of specific protein-binding peptides or peptoids from combinatorial libraries displayed on beads." Mol. BioSyst. 2, (2006): 25-35.
Koide, A. et al. "The fibronectin type III domain as a scaffold for novel binding proteins." J. Mol. Biol. 284, (1998): 1141-1151.
Kornegay, Joe N., et al. "NBD delivery improves the disease phenotype of the golden retriever model of Duchenne muscular dystrophy." Skeletal muscle 4.1 (2014): 18.
Kriegler, M. et al. "A Novel Form of TNF/cachectin Is a Cell Surface Cytotoxic Transmembrane Protein: Ramifications for the Complex Physiology of TNF." Cell 53, (1988): 45-53.
Kyte, Jack, and Russell F. Doolittle. "A simple method for displaying the hydropathic character of a protein." Journal of molecular biology 157.1 (1982): 105-132.
Lam, K. S. et al. "A new type of synthetic peptide library for identifying ligand-binding activity." Nature 354, (1991): 82-84.
LaRochelle, Jonathan R., et al. "Fluorescence correlation spectroscopy reveals highly efficient cytosolic delivery of certain penta-arg proteins and stapled peptides." Journal of the American Chemical Society 137.7 (2015): 2536-2541.
Lättig-Tünnemann, Gisela, et al. "Backbone rigidity and static presentation of guanidinium groups increases cellular uptake of arginine-rich cell-penetrating peptides." Nature communications 2 (2011): 453.
Leduc, A. M. et al. "Helix-stabilized cyclic peptides as selective inhibitors of steroid receptor-coactivator interactions." Proc. Natl. Acad. Sci. USA 100, (2003): 11273-11278.
Leung, C. H. et al. "Structure-based repurposing of FDA-approved drugs as TNF-a inhibitors." ChemMedChem 6, (2011): 765-768.
Lewis, Kaitlyn N., et al. "Nrf2, a guardian of healthspan and gatekeeper of species longevity." Integrative and comparative biology 50.5 (2010): 829-843.
Lian, Wenlong, et al. "Cell-permeable bicyclic peptide inhibitors against intracellular proteins." Journal of the American Chemical Society 136.28 (2014): 9830-9833.
Lian, Wenlong, et al. "Screening bicyclic peptide libraries for protein-protein interaction inhibitors: discovery of a tumor necrosis factor-a antagonist." Journal of the American Chemical Society 135.32 (2013): 11990-11995.
Liu, Jianquan, et al. "Nanostructured materials designed for cell binding and transduction." Biomacromolecules 2.2 (2001): 362-368.

(56) References Cited

OTHER PUBLICATIONS

Liu, R., Maril, J. & Lam, K. S. "A novel peptide-based encoding system for "one-bead one-compound" peptidomimetic and small molecule combinatorial libraries." J. Am. Chem. Soc. 124, (2002): 7678-7680.
Liu, T. et al. "Synthesis and screening of a cyclic peptide library: Discovery of small-molecule ligands against human prolactin receptor." Bioorg. Med. Chem. 17, (2009): 1026-1033.
Liu, T., Qian, Z., Xiao, Q. & Pei, D. "High-throughput screening of one-bead-one compound libraries: identification of cyclic peptidyl inhibitors against calcineurin/NFAT interaction." ACS Comb. Sci. 13, (2011): 537-546.
Liu, X., Chen, C. & Hop, C. E. "Do we need to optimize plasma protein and tissue binding in drug discovery?" Curr. Top. Med. Chem. 11, (2011):450-466.
Lo, Shih-Ching, et al. "Structure of the Keap1: Nrf2 interface provides mechanistic insight into Nrf2 signaling." The EMBO journal 25.15 (2006): 3605-3617.
Luzi et al. Subunit disassembly and inhibition of TNFalpha by a semi-synthetic bicyclic peptide, Protein Engineering, Design, & Selection 28(2), (2015): 45-52.
Ma, Bing, et al. "Total synthesis of the antimitotic bicyclic peptide celogentin c." Journal of the American Chemical Society 132.3 (2009): 1159-1171.
Ma, L. et al. "A Novel Small-Molecule Tumor Necrosis Factor α Inhibitor Attenuates Inflammation in a Hepatitis Mouse Model." J. Biol. Chem. 289, (2014): 12457-12466.
Maiolo, et al. "Effects of cargo molecules on the cellular uptake of arginine-rich cell-penetrating peptides." Biochimica et Biophysica Acta (BBA)—Biomembranes 1712.2 (2005): 161-172.
Mancini, F., Toro, C. M., Mabilia, M., Giannangeli, M., Pinza, M. & Milanese, C. Inhibition of tumor necrosis factor-a (TNF-a)-TNF-a receptor binding by structural analogues of suramin. Biochem. Pharmocol. 58, (1999): 851-859.
Mandal, Deendayal, Amir Nasrolahi Shirazi, and Keykavous Parang. "Cell-penetrating homochiral cyclic peptides as nuclear-targeting molecular transporters." Angewandte Chemie International Edition 50.41 (2011): 9633-9637.
Martin, T. L., Mufson, E. J. & Mesulam, M. M. The light side of horseradish peroxidase histochemistry. J. Histochem. Cytochem. 32, (1984):793.
May, Michael J., et al. "Selective inhibition of NF-κB activation by a peptide that blocks the interaction of NEMO with the IκB kinase complex." Science 289.5484 (2000): 1550-1554.
Millward, S.W., et al., "Design of cyclic peptides that bind protein surfaces with antibody-like affinity." ACS Chem. Biol. 2, (2007): 625-634.
Miranda, E. et al. "A Cyclic Peptide Inhibitor of HIF-1 Heterodimerization That Inhibits Hypoxia Signaling in Cancer Cells." J. Am. Chem. Soc. 135, (2013): 10418-10425.
Mitra, Sayantan, and Amy M. Barrios. "Highly sensitive peptide-based probes for protein tyrosine phosphatase activity utilizing a fluorogenic mimic of phosphotyrosine." Bioorganic & medicinal chemistry letters 15.23 (2005): 5142-5145.
Mueller, Judith, et al. "Comparison of cellular uptake using 22 CPPs in 4 different cell lines." Bioconjugate chemistry 19.12 (2008): 2363-2374.
Muratovska, Aleksandra, and Michael R. Eccles. "Conjugate for efficient delivery of short interfering RNA (siRNA) into mammalian cells." FEBS letters 558.1-3 (2004): 63-68.
Nakase, Ikuhiko, et al. "Efficient intracellular delivery of nucleic acid pharmaceuticals using cell-penetrating peptides." Accounts of chemical research 45.7 (2011): 1132-1139.
Nakase, Ikuhiko, et al. "Interaction of arginine-rich peptides with membrane-associated proteoglycans is crucial for induction of actin organization and macropinocytosis." Biochemistry 46.2 (2007): 492-501.

Ndikuyeze, Georges Habineza, et al. "A phase I clinical trial of systemically delivered NEMO binding domain peptide in dogs with spontaneous activated B-cell like diffuse large B-cell lymphoma." PloS one 9.5 (2014): e95404.
Nevola, Laura, and Ernest Giralt. "Modulating protein-protein interactions: the potential of peptides." Chemical Communications 51.16 (2015): 3302-3315.
Nguyen, Leonard T., et al. "Serum stabilities of short tryptophan- and arginine-rich antimicrobial peptide analogs." PloS one 5.9 (2010): e12684.
Nori, Aparna, et al. "Tat-conjugated synthetic macromolecules facilitate cytoplasmic drug delivery to human ovarian carcinoma cells." Bioconjugate chemistry 14.1 (2003): 44-50.
Oeckinghaus, Andrea, and Sankar Ghosh. "The NF-κB family of transcription factors and its regulation." Cold Spring Harbor perspectives in biology 1.4 (2009): a000034.
Orange et al. "Cell penetrating peptide inhibitors of Nuclear Factor-kappa B," Cell Mol Life Sci, 2008, 62(22), 3564-3591.
Palm-Apergi, Caroline, et al. "The membrane repair response masks membrane disturbances caused by cell-penetrating peptide uptake." The FASEB Journal 23.1 (2009): 214-223.
Pelay-Gimeno, Marta, et al. "Structure-based design of inhibitors of protein—protein interactions: mimicking peptide binding epitopes." Angewandte Chemie International Edition 54.31 (2015): 8896-8927.
Pelay-Gimeno, Marta, et al. "Strukturbasierte Entwicklung von Protein-Protein-Interaktionsinhibitoren: Stabilisierung und Nachahmung von Peptidliganden." Angewandte Chemie 127.31 (2015): 9022-9054.
Pennica, D. et al. "Human Tumour Necrosis Factor: Precursor Structure, Expression and Homology to Lymphotoxin." Nature 312, (1984):724-729.
Peterson, Jennifer M., et al. "Peptide-based inhibition of NF-κB rescues diaphragm muscle contractile dysfunction in a murine model of Duchenne muscular dystrophy." Molecular medicine 17.5-6 (2011): 508-515.
Pham, Wellington, et al. "Enhancing membrane permeability by fatty acylation of oligoarginine peptides." Chembiochem 5.8 (2004): 1148-1151.
Pooga, Margus, et al. "Cellular translocation of proteins by transportan." The FASEB Journal 15.8 (2001): 1451-1453.
Qian et al. "Enhancing the Cell Permeability and Metabolic Stability of Peptidyl Drugs by Reversible Bicylcization," Angew Chem Int Ed English 56(6) (2016): 1525-1529.
Qian, Ziqing, et al. "Discovery and mechanism of highly efficient cyclic cell-penetrating peptides." Biochemistry 55.18 (2016): 2601-2612.
Qian, Ziqing, et al. "Efficient delivery of cyclic peptides into mammalian cells with short sequence motifs." ACS chemical biology 8.2 (2012): 423-431.
Qian, Ziqing, et al. "Intracellular delivery of peptidyl ligands by reversible cyclization: discovery of a PDZ domain inhibitor that rescues CFTR activity." Angewandte Chemie International Edition 54.20 (2015): 5874-5878. Angew. Chem. 2015, 127, 5972.
Qian, Ziqing, et al. "Monitoring the cytosolic entry of cell-penetrating peptides using a pH-sensitive fluorophore." Chemical Communications 51.11 (2015): 2162- 2165.
Qian, Ziqing, et al. "Early endosomal escape of a cyclic cell-penetrating peptide allows effective cytosolic cargo delivery." Biochemistry 53.24 (2014): 4034-4046.
Rajendran, Peramaiyan, et al. "Antioxidants and human diseases." Clinica chimica acta 436 (2014): 332-347.
Reay, Daniel P., et al. "Systemic delivery of NEMO binding domain/IKKγ inhibitory peptide to young mdx mice improves dystrophic skeletal muscle histopathology." Neurobiology of disease 43.3 (2011): 598-608.
Rezai, Taha, et al. "Conformational flexibility, internal hydrogen bonding, and passive membrane permeability: successful in silico prediction of the relative permeabilities of cyclic peptides." Journal of the American Chemical Society 128.43 (2006): 14073-14080.

(56) References Cited

OTHER PUBLICATIONS

Richard, Jean Philippe, et al. "Cellular uptake of unconjugated TAT peptide involves clathrin-dependent endocytosis and heparan sulfate receptors." Journal of Biological Chemistry 280.15 (2005): 15300-15306.

Robinson, John A. "β-Hairpin peptidomimetics: design, structures and biological activities." Accounts of chemical research 41.10 (2008): 1278-1288.

Rothbard, Jonathan B., et al. "Conjugation of arginine oligomers to cyclosporin A facilitates topical delivery and inhibition of inflammation." Nature medicine 6.11 (2000): 1253.

Rothwarf, David M., et al. "IKK-γ is an essential regulatory subunit of the IκB kinase complex." Nature 395.6699 (1998): 297.

Rueping, Magnus, et al. "Cellular uptake studies with β-peptides." ChemBioChem 3.2-3 (2002): 257-259.

Rushe, Mia, et al. "Structure of a NEMO/IKK-associating domain reveals architecture of the interaction site." Structure 16.5 (2008): 798-808.

Rutledge, S.E., Volkman, H.M. & Schepartz, A. "Molecular recognition of protein surfaces: high affinity ligands for the CBPKIX domain." J. Am. Chem. Soc. 125, (2003): 14336-14347.

Saar, Külliki, et al. "Cell-penetrating peptides: a comparative membrane toxicity study." Analytical biochemistry 345.1 (2005): 55-65.

Saito, H. et al. "A tumor necrosis factor receptor loop peptide mimic inhibits bone destruction to the same extent as anti-tumor necrosis factor monoclonal antibody in murine collagen-induced arthritis." Arthritis Rheum. 56, (2007):1164-1174.

Sako, Y., Morimoto, J., Murakami, H. & Suga, H. "Ribosomal synthesis of bicyclic peptides via two orthogonal inter-side-chain reactions." J. Am. Chem. Soc. 130, (2008): 7232-7234.

Sandberg, Mats, et al. "NRF2-regulation in brain health and disease: implication of cerebral inflammation." Neuropharmacology 79 (2014): 298-306.

Schmidt, Nathan, et al. "Arginine-rich cell-penetrating peptides." FEBS letters 584.9 (2010): 1806-1813.

Scholl, Markus, Zuzana Kadlecova, and Harm-Anton Klok. "Dendritic and hyperbranched polyamides." Progress in Polymer Science 34.1 (2009): 24-61.

Schwarze, Steven R., et al. "In vivo protein transduction: delivery of a biologically active protein into the mouse." Science 285.5433 (1999): 1569-1572.

Shen, Q. et al., "De novo design of helical peptides to inhibit tumor necrosis factor-α by disrupting its trimer formation." Med. Chem. Commun. 7, (2016): 725-729.

Shibata, Wataru, et al. "Cutting edge: the IκB kinase (IKK) inhibitor, NEMO-binding domain peptide, blocks inflammatory injury in murine colitis." The Journal of Immunology 179.5 (2007): 2681-2685.

Shrake, A., and J. A. Rupley. "Environment and exposure to solvent of protein atoms. Lysozyme and insulin." Journal of molecular biology 79.2 (1973): 351-371.

Skelton, Nicholas J., et al. "β-hairpin polypeptides by design and selection." Journal of Spectroscopy 17.2-3 (2003): 213-230.

Stanford, Stephanie M., et al. "High-throughput screen using a single-cell tyrosine phosphatase assay reveals biologically active inhibitors of tyrosine phosphatase CD45." Proceedings of the National Academy of Sciences 109.35 (2012): 13972-13977.

Steiner, D., Forrer, P. & Plueckthun, A. "Efficient selection of DARPins with subnanomolar affinities using SRP phage display." J. Mol. Biol. 382, (2008):1211-1227.

Stewart, Kelly M., Kristin L. Horton, and Shana O. Kelley. "Cell-penetrating peptides as delivery vehicles for biology and medicine." Organic & biomolecular chemistry 6.13 (2008): 2242-2255.

Suhorutsenko, Julia, et al. "Cell-penetrating peptides, PepFects, show no evidence of toxicity and immunogenicity in vitro and in vivo." Bioconjugate chemistry 22.11 (2011): 2255-2262.

Sun, Shao-Cong, Jae-Hoon Chang, and Jin Jin. "Regulation of nuclear factor-κB in autoimmunity." Trends in immunology 34.6 (2013): 282-289.

Sun, Y., Lu, G. & Tam, J. P. "A thioester ligation approach to amphipathic bicyclic peptide library." Org. Lett. 3, (2001): 1681-1684.

Sweeney, M. C et al. "Decoding protein-protein interactions through combinatorial chemistry: sequence specificity of SHP-1, SHP-2, and SHIP SH2 domains." Biochemistry 44, (2005): 14932-14947.

Taguchi, Keiko, Hozumi Motohashi, and Masayuki Yamamoto. "Molecular mechanisms of the Keap1—Nrf2 pathway in stress response and cancer evolution." Genes to cells 16.2 (2011): 123-140.

Takada, Y. et al. "Evodiamine Abolishes Constitutive and Inducible NF-κB Activation by Inhibiting IκBα Kinase Activation, Thereby Suppressing NF-κB-regulated Antiapoptotic and Metastatic Gene Expression, Up-regulating Apoptosis, and Inhibiting Invasion." J. Biol. Chem. 280, (2005): 17203-17212.

Takasaki, W., et al., "Structure-based design and characterization of exocyclic peptidomimetics that inhibit TNF alpha binding to its receptor." Nat. Biotechnol. 15, (1997): 1266-1270.

Tang, P. et al. "Human pro-Tumor Necrosis Factor Is a Homotrimer." Biochemistry (Mosc.) 35, (1995): 8216-8225.

Tavassoli, A., et al., "Inhibition of HN budding by a genetically selected cyclic peptide targeting the Gag-TSG 101 interaction." ACS Chem. Biol. 3, (2008): 757-764.

Thakkar, A., Thi, T. B. & Pei, D. "Global analysis of peptide cyclization efficiency." ACS Comb. Sci. 15, (2013): 120-129.

Thakkar, A., Wavreille, A-S. & Pei, D. "Traceless capping agent for peptide sequencing by partial Edman degradation and mass spectrometry." Anal. Chem. 78, (2006): 5935-5939.

Tien, Matthew Z., et al. "Maximum allowed solvent accessibilites of residues in proteins." PloS one 8.11 (2013): e80635.

Timmerman, P. et al. "A combinatorial approach for the design of complementarity determining region-derived peptidomimetics with in vitro anti-tumoral activity." J. Biol. Chem. 284, (2009): 34126-34134.

Tong, Kit I., et al. "Different electrostatic potentials define ETGE and DLG motifs as hinge and latch in oxidative stress response." Molecular and cellular biology 27.21 (2007): 7511-7521.

Tong, Kit I., et al. "Keap1 recruits Neh2 through binding to ETGE and DLG motifs: characterization of the two-site molecular recognition model." Molecular and cellular biology 26.8 (2006): 2887-2900.

Trinh, Thi B., et al. "Discovery of a direct Ras inhibitor by screening a combinatorial library of cell-permeable bicyclic peptides." ACS combinatorial science 18.1 (2015): 75-85.

Upadhyaya, et al. "Direct Ras inhibitors identified from a structurally ridigified bicyclic peptide library." Tetrahedron, 2014, 70(42), 7714-7720.

Upadhyaya, Punit, et al. "Inhibition of Ras signaling by blocking Ras—effector interactions with cyclic peptides." Angewandte Chemie International Edition 54.26 (2015): 7602-7606. Angew. Chem. 127, (2015): 7712.

Varkouhi, Amir K., et al. "Endosomal escape pathways for delivery of biologicals." Journal of Controlled Release 151.3 (2011): 220-228.

Virta, P. & Lonnberg, H. J. "Solid-supported synthesis of cryptand-like macrobicyclic peptides." J. Org. Chem. 68, (2003): 8534.

Vriens, Kim, Bruno Cammue, and Karin Thevissen. "Antifungal plant defensins: mechanisms of action and production." Molecules 19.8 (2014): 12280-12303.

Wadia, Jehangir S., and Steven F. Dowdy. "Transmembrane delivery of protein and peptide drugs by TAT-mediated transduction in the treatment of cancer." Advanced drug delivery reviews 57.4 (2005): 579-596.

Wajant, H. et al. "Tumor Necrosis Factor Signaling." Cell Death Differ 10, (2003): 45-65.

Wells, James A., and Christopher L. McClendon. "Reaching for high-hanging fruit in drug discovery at protein-protein interfaces." Nature 450.7172 (2007): 1001.

White, Tina R., et al. "On-resin N-methylation of cyclic peptides for discovery of orally bioavailable scaffolds." Nature chemical biology 7.11 (2011): 810.

(56) References Cited

OTHER PUBLICATIONS

Wolde, Michael, et al. "Targeting CAL as a negative regulator of AF508-CFTR cell-surface expression an rna interference and structure-based mutagenetic approaCH." Journal of Biological Chemistry 282.11 (2007): 8099-8109.
Wu, X., et al., "Inhibition of Ras-effector interactions by cyclic peptides." Med. Chem. Commun. 4, (2013): 378-382.
Xu, L.H. et al. "Directed evolution of high-affinity antibody mimics using mRNA display." Chem. Biol. 9, (2002):933-942.
Yamagishi, Y. et al. "Natural product-like macrocyclic N-methyl-peptide inhibitors against a ubiquitin ligase uncovered from a ribosome-expressed de novo library." Chem. Biol. 18, (2011):1562-1570.
Yamaoka, Shoji, et al. "Complementation cloning of NEMO, a component of the IκB kinase complex essential for NF-κB activation." Cell 93.7 (1998): 1231-1240.
Yin, J. et al. "Genetically encoded short peptide tag for versatile protein labeling by Sfp phosphopantetheinyl transferase." Proc. Natl. Acad. Sci. USA 102 (2005): 15815-15820.
Zhang, Donna D., et al. "Distinct cysteine residues in Keap1 are required for Keap1-dependent ubiquitination of Nrf2 and for stabilization of Nrf2 by chemopreventive agents and oxidative stress." Molecular and cellular biology 23.22 (2003): 8137-8151.
Zhang, Meijuan, et al. "Emerging roles of Nrf2 and phase II antioxidant enzymes in neuroprotection." Progress in neurobiology 100 (2013): 30-47.
Zhao, Bingchuan, et al. "A Thioether-Stabilized d-Proline-1-Proline-Induced β-Hairpin Peptide of Defensin Segment Increases Its Anti-Candida albicans Ability." ChemBioChem 17.15 (2016): 1416-1420.
Zhao, Kun, et al. "Enhanced activity of cyclic transporter sequences driven by phase behavior of peptide-lipid complexes." Soft Matter 8.24 (2012): 6430-6433.
Zhou, H. et al. "Structure-based design of high-affinity macrocyclic peptidomimetics to block the menin-mixed lineage leukemia 1 (MLLI) protein-protein interaction." J. Med. Chem. (2013) 56, 1113-1123.
International Preliminary Report on Patentability issued for Application No. PCT/US2017/062951 dated Jun. 6, 2019.
International Search Report and Written Opinion. Issued by the International Searching Authority (US) in Application No. PCT/US2017/062951 dated Apr. 30, 2018. 12 pages.
International Search Report and Written Opinion issued for Application No. PCT/US2017/060881 dated Apr. 26, 2018.
International Preliminary Report on Patentability issued for Application No. PCT/US17/60881, dated May 23, 2019.
International Preliminary Report on Patentability issued for Application No. PCT/US2017/063020 dated Jun. 6, 2019.
International Search Report and Written Opinion issued for Application No. PCT/US2017/063020 dated May 4, 2018.
International Search Report and Written Opinion issued for Application No. PCT/US2019/031522, dated Sep. 27, 2019.
International Search Report and Written Opinion issued for Application No. PCT/US2014/039332, dated Dec. 3, 2014,.
International Search Report and Written Opinion issued for Application No. PCT/US2017/062945, dated Feb. 16, 2018.
International Preliminary Report on Patentability issued for Application No. PCT/US2017/062945, dated Jun. 6, 2019.
International Preliminary Report on Patentability issued for Application No. PCT/US2019/031522, dated Nov. 19, 2020.
Extended European Search Report dated Nov. 17, 2016 in European Application No. 14800563.
Extended European Search Report issued in EP 17870556.2, dated Sep. 8, 2020.
Communication Pursuant to Rule 164(1) EPC, issued for U.S. Appl. No. 17/874,485, dated Feb. 3, 2021.
Non-Final Office Action issued in U.S. Appl. No. 16/462,920, dated Aug. 18, 2020.
Final Office Action issued in U.S. Appl. No. 16/462,920, dated Feb. 16, 2021.
Restriction Requirement issued in U.S. Appl. No. 16/462,920, dated Apr. 13, 2020.
Non-Final Office Action issued in U.S. Appl. No. 16/348,706, dated Nov. 16, 2020.
Srinivas, et al., Biaryl amino acid templates in place of D-Pro-L-Pro in cyclic beta-hairpin cationic antimicrobial peptidemimetics, Organic and Biomolecular Chemistry vol. 5, pp. 3100-3105, 2007.
Junkes, Christof, et al. "Cyclic antimicrobial R-, W-rich peptides: the role of peptide structure and E. coli outer and inner membranes in activity and the mode of action." European Biophysics Journal 40.4 (2011): 515-528.
Lai, Jonathan R., et al. "Design of non-cysteine-containing antimicrobial β-hairpins: Structure—activity relationship studies with linear protegrin-1 analogues." Biochemistry 41.42 (2002): 12835-12842.
Langham, Allison A., Alan J. Waring, and Y. N. Kaznessis. "Comparison of interactions between beta-hairpin decapeptides and SDS/DPC micelles from experimental and simulation data." BMC biochemistry 8.1 (2007): 1-13.
D'Souza et al., Structural parameters modulating the cellular uptake of disulfide-rich cyclic cell-penetrating peptides: MCoTl-II and SFTl-1, European Journal of Medicinal Chemistry, vol. 88, 99 10-18, 2014.
Office Action issued for U.S. Appl. No. 17/053,684, dated Apr. 1, 2022.
Office Action issued for U.S. Appl. No. 16/348,706, dated Apr. 15, 2022.
Oh, Donghoon, et al. "Enhanced cellular uptake of short polyarginine peptides through fatty acylation and cyclization." Molecular pharmaceutics 11.8 (2014): 2845-2854.
Do, Hung, et al. "Difatty acyl-conjugated linear and cyclic peptides for siRNA delivery." ACS omega 2.10 (2017): 6939-6957.
Bedewy, Walaa, et al. "Generation of a cell-permeable cycloheptapeptidyl inhibitor against the peptidyl-prolyl somerase Pin1." Organic & biomolecular chemistry 15.21 (2017): 4540-4543.
Extended European Search Report issued for European Application No. 19799961.8, dated Feb. 2, 2022.
Office Action issued for Japanese Application No. 219-524067, dated May 10, 2022.
Office Action issued for U.S. Appl. No. 16/462,922, dated May 10, 2022.
Liu, et al., Cyclic Peptidyl Inhibitors against Human Peptidyl-Prolyl Isomerase Pin1. J Med Chem; 2010, 53: 2491-2501.
U.S. Patent & Trademark Office. Notice of Allowance. Issued in U.S. Appl. No. 16/348,706 dated Aug. 30, 2021. 14 pages.
Japanese Patent Office. Non-Final Office Action. Issued in Application No. 2019-524067 dated Oct. 5, 2021. 9 pages including English translation.
Taiwanese Intellectual Property Office. Non-Final Office Action. Issued in Taiwanese Application No. 106138809 dated Nov. 5, 2021. 11 pages including English translation.
U.S. Patent & Trademark Office. Restriction Requirement. Issued in U.S. Appl. No. 17/053,684 dated Aug. 6, 2021.10 pages.
Advisory Action for U.S. Appl. No. 17/053,684 dated Nov. 2, 2022, 4 pages.
First Office Action with English Translation for Chinese Application No. 201780069098.8 dated Nov. 28, 2022, 15 pages.
Office Action for U.S. Appl. No. 17/053,684 dated Jan. 20, 2023, 10 pages.
Office Action issued in U.S. Appl. No. 17/053,684 dated May 11, 2023.
Office Action issued in CN Application No. 201780069098.8 dated Aug. 3, 2023.
Office Action for U.S. Appl. No. 17/538,330 dated Mar. 16, 2023, 10 pages.
Final Office Action for U.S. Appl. No. 17/053,684, dated May 11, 2023, 6 pages.
Notice of Allowance in U.S. Appl. No. 17/538,330, dated Sep. 7, 2023, 11 pages.
Non-Final Office Action in U.S. Appl. No. 17/053,684, dated Sep. 8, 2023, 13 pages.
Chinese Grant Notification issued in CN Application No. 2017/80069098.8, dated Oct. 25, 2023, 4 pages.

(56) References Cited

OTHER PUBLICATIONS

Pande et al., "Synthesis and Antibacterial Evaluation of Carvosamide Derivatives of Amino Acids", Pharmaceutical Chemistry Journal, Apr. 2014, vol. 48, No. 1, pp. 1-5.
Office Action in JP Application No. 2022-179784, dated Nov. 7, 2023, 5 pages (abstract).

* cited by examiner

BICYCLIC PEPTIDYL INHIBITOR OF TUMOR NECROSIS FACTOR-ALPHA

CROSS REFERENCE TO RELATED APPLICATIONS

This application is a continuation of U.S. patent application Ser. No. 16/462,914, filed on May 21, 2019, which is a national stage application filed under U.S.C. § 371 of PCT International Application No. PCT/US2017/062945, filed on Nov. 22, 2017, which claims the benefit of priority to U.S. Provisional Application No. 62/425,471, filed Nov. 22, 2016, each of which is incorporated by reference herein in its entirety.

STATEMENT REGARDING FEDERALLY FUNDED RESEARCH

This invention was made with government support under grant numbers GM062820, GM110208, and GM122459 awarded by the National Institutes of Health. The government has certain rights in the invention.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: 10336-278US1_ST25.txt, date recorded: Apr. 29, 2020, file size ~2.6 kilobytes).

BACKGROUND

Tumor necrosis factor-alpha (TNFα) is a pleiotropic inflammatory cytokine with a myriad of and often-conflicting functions. It is produced as a 26-kDab type II transmembrane protein and released from the membrane as a soluble 51-kDa noncovalently associated homotrimer (Pennica, D.; et al., "Human Tumour Necrosis Factor: Precursor Structure, Expression and Homology to Lymphotoxin." *Nature* 1984, 312:724-729; Kriegler, M.; et al., "A Novel Form of TNF/cachectin is a Cell Surface Cytotoxic Transmembrane Protein: Ramifications for the Complex Physiology of TNF." *Cell* 1988, 53:45-53; Tang, P.; et al., "Human pro-Tumor Necrosis Factor Is a Homotrimer." *Biochemistry (Mosc.)* 1996, 35:8216-8225). Most of the TNFα's biological functions are mediated through binding to TNFα receptor-1 (TNFR1) (Chen, G.; et al., "TNF-R1 Signaling: A Beautiful Pathway." *Science* 2002, 296:1634-1635; Wajant, H.; et al., "Tumor Necrosis Factor Signaling." *Cell Death Differ.* 2003, 10:45-65). For example, binding of TNFα to TNFR1 activates the transcription factor NF-κB, which mediates the transcription of a vast array of proteins involved in cell survival and proliferation, inflammatory response, and anti-apoptotic factors. It can also activate the MAPK pathways especially the c-Jun N-terminal kinase (JNK), which in turn regulates several important cellular functions including cell growth, differentiation, survival and apoptosis. Finally, TNFα-TNFR1 interaction induces death signaling by activating caspase-8.

Because of its role in promoting inflammatory responses, TNFα causes many of the clinical problems associated with autoimmune disorders such as rheumatoid arthritis, ankylosing spondylitis, inflammatory bowel disease (IBD), psoriasis, hidradenitis suppurativa, and refractory asthma (Esposito, E.; et al., "TNF-Alpha as a Therapeutic Target in Inflammatory Diseases, Ischemia-Reperfusion Injury and Trauma." *Curr. Med. Chem.* 2009, 16:3152-3167). These disorders are currently treated with macromolecular TNF inhibitors such as monoclonal antibodies infliximab (Remicade), adalimumab (Humira), and certolizumab pegol (Cimzia), or a circulating receptor fusion protein etanercept (Enbrel). These proteins bind specifically to TNFα and prevent it from interacting with its cognate receptors. The main limitations of protein-based drugs are their high costs of production, requirement of injections, and potential immunogenicity. Therefore, despite of the remarkable clinical success of the protein inhibitors, there remain significant interests in developing low-molecular-weight TNFα inhibitors (including small molecules (He, M. M.; et al., "Small-Molecule Inhibition of TNF-α." *Science* 2005, 310:1022-1025; Buller, F.; et al., "Discovery of TNF Inhibitors from a DNA-Encoded Chemical Library based on Diels-Alder Cycloaddition." *Chem. Biol.* 2009, 16:1075-1086; Chan, D. S.; et al., "Structure-Based Discovery of Natural-Product-like TNF-α Inhibitors." *Angew. Chem. Int. Ed.* 2010, 49:2860-2864; Ma, L.; et al., "A Novel Small-Molecule Tumor Necrosis Factor α Inhibitor Attenuates Inflammation in a Hepatitis Mouse Model." *J. Biol. Chem.* 2014, 289: 12457-12466), cyclic peptides (Takasaki, W.; et al., "Structure Based Design and Characterization of Exocyclic Peptidomimetics That Inhibit TNFα Binding to Its Receptor." In *Peptide Science—Present and Future*; Shimonishi, Y, Ed.; Springer Netherlands, 1999; pp 61-63; Lian, W.; et al., "Screening Bicyclic Peptide Libraries for Protein—Protein Interaction Inhibitors: Discovery of a Tumor Necrosis Factor-α Antagonist." *J. Am. Chem. Soc.* 2013, 135:11990-11995; Luzi, S.; et al., "Subunit Disassembly and Inhibition of TNFα by a Semi-Synthetic Bicyclic Peptide." *Protein Eng. Des. Sel.* 2015, 28:45-52), and α-helical peptides (Shen, Q.; et al., "De novo design of helical peptides to inhibit tumor necrosis factor-α by disrupting its trimer formation." *Med. Chem. Commun.*, 2016, 7:725-729), which have the potential to be administered orally.

For the cyclic peptide TNFα inhibitors, they can offer significant advantages over monoclonal antibodies. Because TNFα is an extracellular target, a metabolically stable cyclic peptide inhibitor against TNFα can be administered orally, greatly improving convenience, patient comfort and compliance. Since peptides (including cyclic peptides) are generally impermeable to the cell membrane and cross the gut epithelium poorly, an orally administered cyclic peptide drug would be largely confined within the gastrointestinal tract, minimizing systemic exposure and therefore the risk of serious infections and development of anti-drug antibodies (which may cause eventual loss of drug response). What are still needed are new cyclic peptide TNFα inhibitors with improved efficacy, bioavailability, and/or stability. The compounds and compositions disclosed herein, as well as methods of using such compounds and compositions, address these and other needs.

SUMMARY

Disclosed herein are compounds, compositions, methods for making and using such compounds and compositions. In further aspects disclosed herein are bicyclic peptides, compositions comprising such bicyclic peptides, and methods of making and using them. Methods of screening combinatorial libraries of bicyclic peptides displayed on small-molecule scaffolds are also disclosed. Screening a bicyclic peptide library against TNFα identified potent antagonists that protect cells from TNFα-induced cell death are disclosed.

Also disclosed herein is a method of treating or preventing a disorder in a subject, such as a human, comprising administering to the subject an effective amount of a compound disclosed herein or a pharmaceutically acceptable salt thereof. In some examples, the subject is an animal, such as a human. In some examples, the subject is identified as having a need for treatment of the disorder. In some examples, the method treats a disorder. In some examples, the disorder is associated with TNFα-induced cell death, such as dysfunctional regulation of TNFα-induced cell death. In some examples the disorder is associated with uncontrolled cellular proliferation, such as cancer. In some examples, the disorder is cancer. In some examples the disorder is an inflammatory disorder since TNFα is involved in inflammation; examples of such inflammatory disorders include irritable bowel syndrome. In some examples, the disorder is an autoimmune disorder since TNFα is involved in immune mediated disorders; examples of such disorders include rheumatoid arthritis, ankylosing spondylitis, inflammatory bowel disease, Crohn's disease, ulcerative colitis, psoriasis, hidradenitis suppurativa, and refractory asthma.

Also disclosed herein is a method for identifying a drug candidate for treatment of a disorder, the method comprising the steps of: exposing a compound disclosed herein, a compound prepared by the methods disclosed herein, a library disclosed herein, or a library prepared by the methods disclosed to a receptor associated with the disorder; b) detecting reaction between the receptor and the compound or the library; and c) determining the identity of compound reacting with the receptor.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

FIG. 7A is a graph showing the viability of WEHI-13VAR fibroblasts as a function of TNFα concentration in the presence and absence of 10 μM C1-74-2. FIG. 7B is a Western blot analysis of the cytoplasmic levels of NF-kB on HT29 colon cancer cells after pretreatment with varying concentrations of C1-74-2 and stimulation with 1 ng/mL TNFα. GAPDH was used as loading control. FIG. 7C is a Western blot analysis of the nuclear levels of NF-kB in HT29 cells after pretreatment with varying concentrations of C1-74-2 and stimulation with 1 ng/mL TNFα. Histone H3 was used as loading control.

DETAILED DESCRIPTION

Figure 1A:
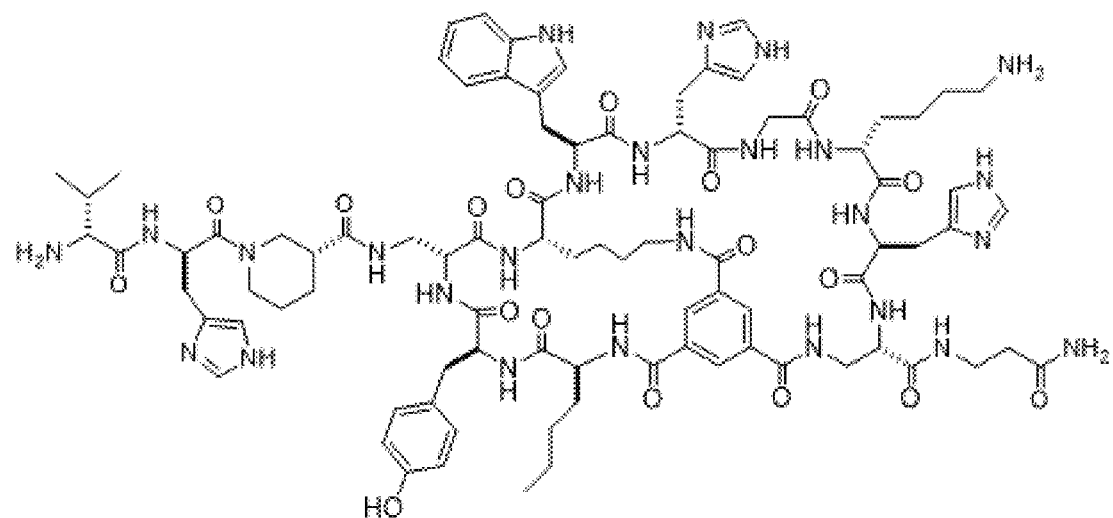
FIG. 1A shows the structure of anticachexin C1-74-2.

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

General Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" refers to the target of administration, e.g. a subject. Thus the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig, fish, bird, rodent, or fruit fly. The term does not denote a particular age or sex. Thus, adult and newborn subjects, as well as fetuses, whether male or female, are intended to be covered. In some examples, the subject is a mammal. A patient refers to a subject afflicted with a disease or disorder. The term "patient" includes human and veterinary subjects. In some examples of the disclosed methods, the subject has been diagnosed with a need for treatment of cancer, autoimmune disease, and/or inflammation prior to the administering step. In some examples of the disclosed method, the subject has been diagnosed with cancer prior to the administering step. The term subject also includes a cell, such as an animal, for example human, cell.

As used herein, the term "treatment" refers to the medical management of a patient with the intent to cure, ameliorate, or stabilize a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; and supportive treatment, that is, treatment employed to supplement another specific therapy directed toward the improvement of the associated disease, pathological condition, or disorder. In some examples, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease.

As used herein, the term "prevent" or "preventing" refers to precluding, averting, obviating, forestalling, stopping, or hindering something from happening, especially by advance action.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with cancer" means having been subjected to a physical examination by a person of skill, for example, a physician, and found to have a condition that can be diagnosed or treated by a compound or composition that can treat or prevent cancer. As a further example, "diagnosed with a need for treating or preventing cancer" refers to having been subjected to a physical examination by a person of skill, for example, a physician, and found to have a condition characterized by cancer or other disease wherein treating or preventing cancer would be beneficial to the subject.

As used herein, the phrase "identified to be in need of treatment for a disorder," or the like, refers to selection of a subject based upon need for treatment of the disorder. For example, a subject can be identified as having a need for treatment of a disorder (e.g., a disorder related to cancer) based upon an earlier diagnosis by a person of skill and thereafter subjected to treatment for the disorder. It is contemplated that the identification can, in some examples, be performed by a person different from the person making the diagnosis. It is also contemplated, in some examples, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In some examples, a preparation can be administered therapeutically; that is, administered to treat an existing disease or condition. In some examples, a preparation can be administered prophylactically; that is, administered for prevention of a disease or condition.

The term "contacting" as used herein refers to bringing a disclosed compound and a target (e.g., a cell, target receptor, transcription factor, or other biological entity) together in such a manner that the compound can affect the activity of the target either directly, i.e., by interacting with the target itself, or indirectly, i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary and can be administered in one or more dose administrations daily, for one or several days. Guidance can be found in the literature for appropriate dosages for given classes of pharmaceutical products. In some examples, a preparation can be administered in a "prophylactically effective amount"; that is, an amount effective for prevention of a disease or condition.

As used herein, "$EC_{50}$," is intended to refer to the concentration or dose of a substance (e.g., a compound or a drug) that is required for 50% enhancement or activation of a biological process, or component of a process, including a protein, subunit, organelle, ribonucleoprotein, etc. $EC_{50}$ also refers to the concentration or dose of a substance that is required for 50% enhancement or activation in vivo, as further defined elsewhere herein. Alternatively, $EC_{50}$ can refer to the concentration or dose of compound that provokes a response halfway between the baseline and maximum response. The response can be measured in an in vitro or in vivo system as is convenient and appropriate for the biological response of interest. For example, the response can be measured in vitro using cultured cells or in an ex vivo organ culture system with isolated cells. Alternatively, the response can be measured in vivo using an appropriate research model such as rodent, including mice and rats. The mouse or rat can be an inbred strain with phenotypic characteristics of interest such as cancer or inflammation. As appropriate, the response can be measured in a transgenic or knockout mouse or rat wherein the gene or genes has been introduced or knocked-out, as appropriate, to replicate a disease process.

As used herein, "$IC_{50}$," is intended to refer to the concentration or dose of a substance (e.g., a compound or a drug) that is required for 50% inhibition or diminuation of a biological process, or component of a process, including a protein, subunit, organelle, ribonucleoprotein, etc. $IC_{50}$ also refers to the concentration or dose of a substance that is required for 50% inhibition or diminuation in vivo, as further defined elsewhere herein. Alternatively, $IC_{50}$ also refers to the half maximal (50%) inhibitory concentration (IC) or inhibitory dose of a substance. The response can be measured in an in vitro or in vivo system as is convenient and appropriate for the biological response of interest. For example, the response can be measured in vitro using cultured cells or in an ex vivo organ culture system with isolated cells. Alternatively, the response can be measured in vivo using an appropriate research model such as rodent, including mice and rats. The mouse or rat can be an inbred strain with phenotypic characteristics of interest such as cancer or inflammation. As appropriate, the response can be measured in a transgenic or knockout mouse or rat wherein a gene or genes has been introduced or knocked-out, as appropriate, to replicate a disease process.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

Chemical Definitions

As used herein, the term "substituted" is contemplated to include all permissible substituents of organic compounds. In some examples, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain examples, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more CH$_2$ groups linked to one another. The polyalkylene group can be represented by the formula —(CH$_2$)$_a$—, where "a" is an integer of from 2 to 500.

The terms "alkoxy" and "alkoxyl" as used herein refer to an alkyl or cycloalkyl group bonded through an ether linkage; that is, an "alkoxy" group can be defined as —OA$^1$ where $A^1$ is alkyl or cycloalkyl as defined above. "Alkoxy" also includes polymers of alkoxy groups as just described; that is, an alkoxy can be a polyether such as $-OA^1-OA^2$ or $-OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

"Carbocyclyl," "carbocyclic ring" or "carbocycle" refers to a ring structure, wherein the atoms which form the ring are each carbon. Carbocyclic rings can comprise from 3 to 20 carbon atoms in the ring. Carbocyclic rings include aryls and cycloalkyl, cycloalkenyl and cycloalkynyl as defined herein. The carbocyclic group can be substituted or unsubstituted. The carbocyclic group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $-NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula —($A^1$O(O)C-$A^2$-C(O)O)$_a$— or —($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula —$(A^1O\text{-}A^2O)_n$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned herein are preferably those that result in the formation of stable or chemically feasible compounds. In is also contemplated that, in some examples, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in some examples, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$O(CH_2)_{0-4}R^\circ$, —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH=CHPh, which may be substituted with $R^\circ$; —$(CH_2)_{0-4}O(CH_2)_{0-1}$-pyridyl which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR$—, $SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; $C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —$(C_{1-4}$ straight or branched)alkylene)O—$N(R^\circ)_2$; or —$(C_{1-4}$ straight or branched) alkylene)C(O)O—$N(R^\circ)_2$, wherein each $R^\circ$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)O$_2$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR, —(C$_{1-4}$ straight or branched alkylene)C(O)OR, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include ═O and ═S.

Suitable divalent substituents on a saturated carbon atom of an "optionally substituted" group include the following: ═O, ═S, ═NNR*$_2$, ═NNHC(O)R*, ═NNHC(O)OR*, ═NNHS(O)$_2$R*, ═NR*, ═NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(halonR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(halonR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "*Protective Groups in Organic Synthesis*," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In some examples, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

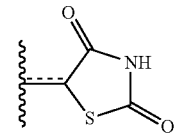

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the compounds and compositions disclosed herein unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In some examples, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the compounds and compositions disclosed herein include all such possible isomers, as well as mixtures of such isomers.

As used herein, the symbol

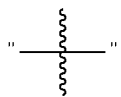

(hereinafter can be referred to as "a point of attachment bond") denotes a bond that is a point of attachment between two chemical entities, one of which is depicted as being attached to the point of attachment bond and the other of which is not depicted as being attached to the point of attachment bond. For example,

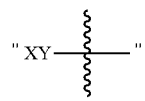

indicates that the chemical entity "XY" is bonded to another chemical entity via the point of attachment bond. Furthermore, the specific point of attachment to the non-depicted chemical entity can be specified by inference. For example, the compound $CH_3$—$R^3$, wherein $R^3$ is H or

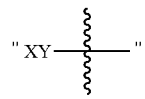

infers that when $R^3$ is "XY", the point of attachment bond is the same bond as the bond by which $R^3$ is depicted as being bonded to $CH_3$.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the compounds and compositions disclosed herein include all such possible diastereomers as well as their racemic mixtures, their substantially pure resolved enantiomers, all possible geometric isomers, and pharmaceutically acceptable salts thereof Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds disclosed herein include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$ respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds and prodrugs thereof can generally be prepared by carrying out the procedures below, by substituting a readily available isotopically labeled reagent for a non-isotopically labeled reagent.

The compounds described herein can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds disclosed herein to form solvates and hydrates. Unless stated to the contrary, all such possible solvates are included in the discussion herein.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

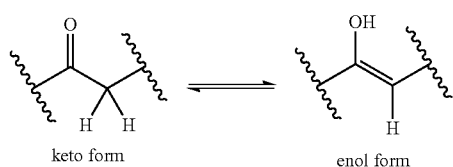

keto form     enol form

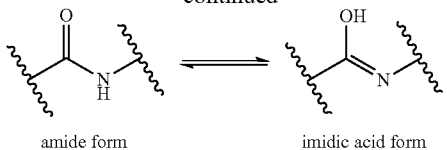

amide form     imidic acid form

Likewise, amides with an N-hydrogen can exist in an equilibrium of the amide form and the imidic acid form. Unless stated to the contrary, all such possible tautomers are included herein.

It is known that chemical substances form solids which are present in different states of order which are termed polymorphic forms or modifications. The different modifications of a polymorphic substance can differ greatly in their physical properties. The compounds can be present in different polymorphic forms, with it being possible for particular modifications to be metastable. Unless stated to the contrary, all such possible polymorphic forms are included.

In some examples, a structure of a compound can be represented by a formula:

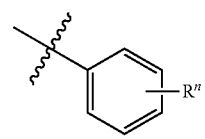

which is understood to be equivalent to a formula:

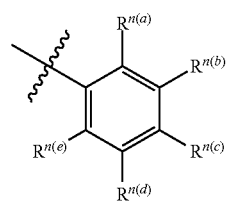

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions disclosed herein as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions disclosed herein. Thus, if there are a variety of additional steps that can be performed it is understood that each of these additional steps can be performed with any specific embodiment or combination of embodiments of the methods disclosed herein.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Abbreviations used herein are as follows: Alloc, allyloxycarbonyl; Cpa, L-4-chlorophenylalanine; dap, D-2,3-diaminopropionic acid; Dap, L-2,3-diaminopropionic acid; FA, fluorescence anisotropy; FITC, fluorescein isothiocyanate; Fpa, L-4-fluorophenylalanine; $F_2pa$, L-3,4-difluorophenylalanine; fpa, D-2-fluorophenylalanine; $f_2pa$, D-3,4-difluorophenylalanine; HRP, horseradish peroxidase; JNK, c-Jun N-terminal kinase; miniPEG, 8-amino-3,6-dioxaoctanoic acid; MTT, 3-(4,5-dimethylthiazol-2-yl)-2,5-diphenyltetrazolium bromide; Nal, L-2-naphthylalanine; Nip, (R)-nipecotic acid; Nle, norleucine; Orn, ornithine; Phg, L-α-phenylglycine; PPI, protein-protein interaction; Sar, sarcosine; TNFα, tumor necrosis factor-alpha; TNFR, TNFα receptor.

Compounds

In previous studies, screening of a naïve bicyclic peptide against TNFα identified anticachexin C1 as a moderately potent TNFα antagonist, which blocks the TNFα-TNFRI interaction with an $IC_{50}$ value of 3.1 μM (Lian, W.; et al., supra). Cyclic and bicyclic peptide hits derived from other screening campaigns against protein-protein interaction (PPI) targets (which generally do not contain major binding pockets) typically exhibit a similar level of potencies (i.e., $IC_{50}/K_D$ values in the high nM to low μM range) (Liu, T., et al., "Synthesis and screening of a cyclic peptide library: Discovery of small-molecule ligands against human prolactin receptor." *Bioorg. Med. Chem.* 2009, 17:1026-1033; Liu, T.; et al., "High-Throughput Screening of One-Bead-One-Compound Libraries: Identification of Cyclic Peptidyl Inhibitors against Calcineurin/NFAT Interaction." *ACS Comb. Sci.* 2011, 13:537-546; Dewan, V.; et al., "Cyclic peptide inhibitors of HIV-1 capsid-human lysyl-tRNA synthetase interaction." *ACS Chem. Biol.* 2012, 7:761-769; Desimmie, B. A.; et al., "Phage Display-directed Discovery of LEDGF/p75 Binding Cyclic Peptide Inhibitors of HIV Replication." *Mol. Therapy* 2012, 20:2064-2075; Birts, C. N.; et al., "A cyclic peptide inhibitor of C-terminal binding protein dimerization links metabolism with mitotic fidelity in breast cancer cells." *Chem. Sci.* 2013, 4:3046-3057; Miranda, E.; et al., "A Cyclic Peptide Inhibitor of HIF-1 Heterodimerization That Inhibits Hypoxia Signaling in Cancer Cells." *J. Am. Chem. Soc.* 2013, 135:10418-10425). These hits require substantial improvement in potency (and specificity) before becoming useful as therapeutic agents or chemical probes.

Disclosed herein, SAR analysis and optimization was performed on all nine residues within the bicyclic structure of anticachexin C1, which in certain examples improved the potency by 44-fold ($IC_{50}$=70 nM). Further improvement of the potency was achieved by constructing and screening a second-generation library, in which a degenerate tripeptide sequence was appended to the side chain of a noncritical residue, to engage in additional interactions with the TNFα surface. The resulting TNFα inhibitor ($IC_{50}$=12 nM) can be used as a potent TNFα inhibitor or can serve as a useful lead for further development into therapeutic agents. The combination of ring residue optimization and exocyclic structural extension can offer a general strategy for optimization of cyclic/bicyclic peptide hits derived from combinatorial libraries.

More specifically, a planar scaffold, trimesic acid, can be used in order to maximize the surface area of the resulting molecules and therefore their ability to interact with flat protein surfaces such as the PPI interfaces. A bicyclic peptide library was generated by "wrapping" a peptide sequence of up to 10 random residues around the trimesoyl group. Peptide cyclization was mediated by the formation three amide bonds between the trimesoyl scaffold and the N-terminal amine, the side chain of a C-terminal L-2,3-diaminopropionic acid (Dap), and the side chain of a fixed lysine within the random region.

In a particular aspect, disclosed herein are bicyclic peptides of Formula I.

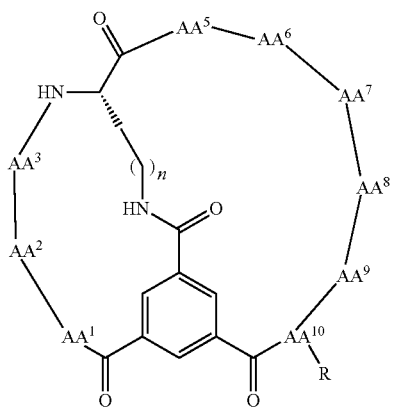

wherein AA$^1$-AA$^3$ and AA$^5$-AA$^{10}$ are amino acid residues, R is null, carboxylic acid, amide, or C$_{1-20}$ keto, ester, amino acid residue, or functionalized peptide moiety of from 2 to 10 amino acid residues in length, and n is an integer of from 1 to 6. Each amino acid residue can be a natural or non-natural amino acid residue. The term "non-natural amino acid" refers to an organic compound that is a congener of a natural amino acid in that it has a structure similar to a natural amino acid so that it mimics the structure and reactivity of a natural amino acid. The non-natural amino acid can be a modified amino acid, and/or amino acid analog, that is not one of the 20 common naturally occurring amino acids or the rare natural amino acids selenocysteine or pyrrolysine. Non-natural amino acids can also be the D-isomer of the natural amino acids. In some examples, one or more amino acid residues is the D-isomer. Examples of suitable amino acids include, but are not limited to, alanine, allosoleucine, arginine, asparagine, aspartic acid, cysteine, glutamine, glutamic acid, glycine, histidine, isoleucine, leucine, lysine, methionine, naphthylalanine, phenylalanine, proline, pyroglutamic acid, serine, threonine, tryptophan, tyrosine, valine, a derivative, or combinations thereof. These, and others, are listed in the Table A along with their abbreviations used herein.

TABLE A

Amino Acid Abbreviations

| Amino Acid | Abbreviations* |
|---|---|
| Alanine | Ala (A) |
| Allosoleucine | AIle |
| Arginine | Arg (R) |
| asparagine | Asn (N) |
| aspartic acid | Asp (D) |
| cysteine | Cys (C) |
| cyclohexylalanine | Cha |
| 4-chlorophenylalanine | Cpa |
| 2,3-diaminopropionic acid | Dap |
| 3,4,-difluorophenylalanice | F$_2$pa |
| 4-fluorophenylalanine | Fpa (Σ) |
| glutamic acid | Glu (E) |
| glutamine | Gln (Q) |
| glycine | Gly (G) |
| histidine | His (H) |
| homoproline | Pip (Θ) |
| isoleucine | Ile (I) |
| leucine | Leu (L) |
| lysine | Lys (K) |
| methionine | Met (M) |
| naphthylalanine | Nal (Φ) |

TABLE A-continued

Amino Acid Abbreviations

| Amino Acid | Abbreviations* |
|---|---|
| norleucine | Nle (Ω) |
| phenylalanine | Phe (F) |
| phenylglycine | Phg (Ψ) |
| 4-(phosphonodifluoromethyl)phenylalanine | F$_2$Pmp (Λ) |
| pipecolic acid | Pp (ϑ) |
| proline | Pro (P) |
| sarcosine | Sar (Ξ) |
| selenocysteine | Sec (U) |
| serine | Ser (S) |
| threonine | Thr (T) |
| tyrosine | Tyr (Y) |
| tryptophan | Trp (W) |
| valine | Val (V) |

*single letter abbreviations: when shown in capital letters herein it indicates the L-amino acid form, when shown in lower case herein it indicates the D-amino acid form The amino acids AA$^1$-AA$^3$ and AA$^5$-AA$^{10}$ can be coupled to one another by a peptide bond or a modified peptide bond, such as by —N(alkyl)C(O)—. In certain examples, disclosed are a subset of compounds of Formula I where n is 3; this is labeled as Formula I-A.

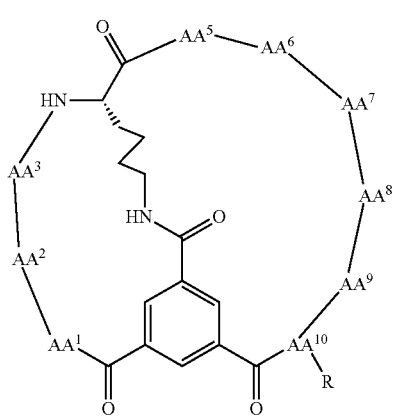

wherein AA$^1$-AA$^3$ and AA$^5$-AA$^{10}$ and R are as defined above for Formula I.

In still further examples, disclosed herein are compounds of Formula II:

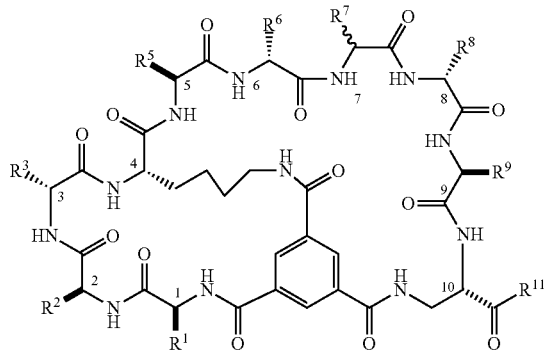

wherein R$^1$, R$^2$, R$^3$, R$^5$, R$^6$, R$^7$, R$^8$, R$^9$, are side chains of amino acid residues AA$^{1-3}$ and AA$^{5-9}$ respectively. R$^{11}$ is OH, NH$_2$, R$^{12}$, or NHR$^{12}$, where R$^{12}$ is an amino acid residue, or substituted or unsubstituted, branched or straight chain C$_{1-20}$ alkyl, substituted or unsubstituted, branched or straight chain OC$_{1-20}$ alkyl, or a functionalized peptide moiety of from 2 to 10 amino acid residues in length, any of which is optionally coupled to a detectable moiety or therapeutic moiety.

In specific examples, disclosed herein are compounds of Formula II, wherein R$^1$ can be a hydrophobic moiety. For example, R$^1$ can be phenyl, benzyl, or substituted or unsubstituted, branched or straight chain C$_{1-20}$ alkyl. In specific examples, R$^1$ can be methyl, ethyl, n-propyl, i-propyl, n-butyl, s-butyl, i-butyl, t-butyl, pentyl, or hexyl. In preferred examples, R$^1$ can be phenyl or n-butyl.

In specific examples, disclosed herein are compounds of Formula II, wherein R$^2$ can be an aryl moiety. For example, R$^2$ can be unsubstituted phenyl or benzyl, or phenyl or benzyl substituted with one or more halo, OH, SH, CO$_2$H, or NH$_2$ groups. In specific examples, R$^2$ can be benzyl (CH$_2$C$_6$H$_6$), 4-hydroxybenzyl, 4-fluorobenzyl, 4-chlorobenzyl, or 3,4-difluorobenzyl. In preferred examples, R$^2$ can be 4-hydroxybenzyl.

In specific examples, disclosed herein are compounds of Formula II, wherein R$^3$ can be a small (e.g., less than 5 atoms in length) neutral or hydrophilic moiety. For example, R$^3$ can be H, unsubstituted C$_{1-6}$ alkyl or C$_{1-6}$ alkyl substituted with one or more halo, OH, SH, CO$_2$H, or NH$_2$ groups. In specific examples, R$^3$ can be —CH$_2$OH, —CHOHCH$_3$, —CH$_2$SH, —CH$_2$CO$_2$, —(CH$_2$)$_2$CO$_2$H, —(CH$_2$)$_4$NH$_2$, or —CH$_2$CONH$_2$. In preferred examples, R$^3$ can be —CH$_3$ or —CH$_2$OH.

In other examples, R$^3$ is a peptide of from 2 to 8 amino acids in length, e.g., from 3 to 6, from 4 to 5, from 2 to 4, or from 3 to 5 amino acids in length. The amino acids in the peptide of R$^3$ in these examples can be natural or unnatural amino acids. In specific examples R$^3$ is a tripeptide comprising natural and/or unnatural amino acids. In further specific examples, R$^3$ is a tripeptide X$^1$-X$^2$-X$^3$ where X$^1$ and X$^3$ are nonatural amino acids, e.g., D-α-amino acids (4-iodo-D-phenylalanine, 4-cyano-D-phenylalanine, 2-fluoro-D-phenylalanine (fpa), 3,4-difluoro-D-phenylalanine (f2pa), D-Trp, D-Asp, D-Val, D-Thr, D-Pro, D-Ser, D-Leu, D-Phe, D-Ala, D-Tyr, D-Nal, D-Glu, D-Asn, D-Lys, D-Arg, D-His). In further examples, X$^2$ is an unnatural amino acid, e.g., 3-amino benzoic acid (Abz), L-β-homoisoleucine, (R)-nipecotic acid (Nip), 4-amino-1-methylpyrrole-3-carboxylic acid, γ-aminobutyric acid, β-Ala, D-homophenylalanine, D-Thr, D-Pro, D-Ser, D-Leu, D-Phe, (S)-3-amino-5-phenylpentanoic acid (apa), D-Tyr, D-Nal, D-Glu, D-Asn, D-Lys, D-Arg, and D-His.

In specific examples, disclosed herein are compounds of Formula II, wherein R$^5$ can be an aryl moiety. For example, R$^5$ can be unsubstituted phenyl, benzyl, heteroaryl or CH$_2$heteroaryl, or phenyl, benzyl, heteroaryl or —CH$_2$heteroaryl substituted with one or more halo, OH, SH, CO$_2$H, or NH$_2$ groups. In specific examples, R$^5$ can be benzyl 4-hydroxybenzyl, 4-fluorobenzyl, 4-chlorobenzyl, 3,4-difluorobenzyl, —CH$_2$Imidazole, or —CH$_2$Indole. In a preferred examples, R$^5$ can be —CH$_2$Indole.

In specific examples, disclosed herein are compounds of Formula II, wherein R$^6$ can be a hydrophilic moiety. For example, R$^6$ can be CH$_2$Imidazole, or C$_{1-6}$ alkyl, benzyl, or phenyl substituted with one or more halo, OH, SH, CO$_2$H, or NH$_2$ groups. In a preferred example, R$^6$ can be CH$_2$Indole.

In specific examples, disclosed herein are compounds of Formula II, wherein R$^7$ can be a small (e.g., less than 5 atoms in length) moiety such as H, unsubstituted C$_{1-2}$ alkyl, or C$_{1-2}$ alkyl substituted with OH, SH, NH$_2$, or CO$_2$H. In a preferred example, R$^7$ is H.

In specific examples, disclosed herein are compounds of Formula II, wherein R$^8$ can be a hydrophilic moiety. For example, R$^8$ can be C$_{1-6}$ alkyl substituted with one or more halo, OH, SH, CO$_2$H, or NH$_2$ groups. In specific examples, R$^8$ can be —CH$_2$OH, —CHOHCH$_3$, —CH$_2$SH, —CH$_2$CO$_2$, —(CH$_2$)$_2$CO$_2$H, —(CH$_2$)$_4$NH$_2$, or —CH$_2$CONH$_2$. In a preferred example, R$^8$ can be —(CH$_2$)$_4$NH$_2$.

In specific examples, disclosed herein are compounds of Formula II, wherein R$^9$ can be can be CH$_2$Imidazole, or C$_{1-6}$ alkyl, benzyl, or phenyl substituted with one or more halo, OH, SH, CO$_2$H, or NH$_2$ groups. In a preferred example, R$^9$ can be CH$_2$Imidazole.

In specific examples, R$^{11}$ and R$^{12}$ can be, independently, arginine, lysine, aspartic acid, norleucine, phenylalanine, beta alanine or any of the sequences for R$_1$ shown in Table 5 or 6, any of which can be coupled to a detectable moiety or therapeutic moiety.

Disclosed herein is a bicyclic peptide having Formula II-A.

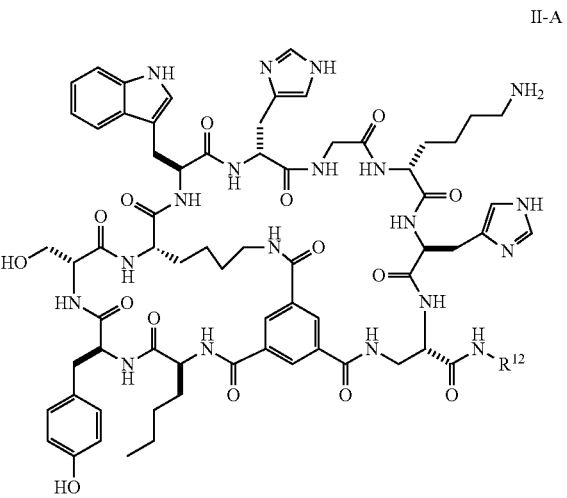

II-A wherein R$^{11}$ is H or R$^{12}$ as defined in Formula II.

In some examples, the compounds disclosed herein can linked to label moiety at R$^{11}$ or R$^{12}$. The label moiety can comprise any detectable label. Examples of suitable detectable labels include, but are not limited to, a UV-Vis label, a near-infrared label, a luminescent group, a phosphorescent group, a magnetic spin resonance label, a photosensitizer, a photocleavable moiety, a chelating center, a heavy atom, a radioactive isotope, a isotope detectable spin resonance label, a paramagnetic moiety, a chromophore, or any combination thereof. In some embodiments, the label is detectable without the addition of further reagents.

In some embodiments, the label moiety is a biocompatible label moiety, such that the compounds can be suitable for use in a variety of biological applications. "Biocompatible" and "biologically compatible", as used herein, generally refer to compounds that are, along with any metabolites or degradation products thereof, generally non-toxic to cells and tissues, and which do not cause any significant adverse effects to cells and tissues when cells and tissues are incubated (e.g., cultured) in their presence.

The label moiety can contain a luminophore such as a fluorescent label or near-infrared label. Examples of suitable luminophores include, but are not limited to, metal porphyrins; benzoporphyrins; azabenzoporphyrine; napthoporphyrin; phthalocyanine; polycyclic aromatic hydrocarbons such as perylene, perylene diimine, pyrenes; azo dyes; xanthene dyes; boron dipyoromethene, aza-boron dipyoromethene, cyanine dyes, metal-ligand complex such as bipyridine, bipyridyls, phenanthroline, coumarin, and acetylacetonates of ruthenium and iridium; acridine, oxazine derivatives such as benzophenoxazine; aza-annulene, squaraine; 8-hydroxyquinoline, polymethines, luminescent producing nanoparticle, such as quantum dots, nanocrystals; carbostyril; terbium complex; inorganic phosphor; ionophore such as crown ethers affiliated or derivatized dyes; or combinations thereof. Specific examples of suitable luminophores include, but are not limited to, Pd (II) octaethylporphyrin; Pt (II)-octaethylporphyrin; Pd (II) tetraphenylporphyrin; Pt (II) tetraphenylporphyrin; Pd (II) meso-tetraphenylporphyrin tetrabenzoporphine; Pt (II) meso-tetrapheny metrylbenzoporphyrin; Pd (II) octaethylporphyrin ketone; Pt (II) octaethylporphyrin ketone; Pd (II) meso-tetra(pentafluorophenyl)porphyrin; Pt (II) meso-tetra (pentafluorophenyl) porphyrin; Ru (II) tris(4,7-diphenyl-1,10-phenanthroline) (Ru (dpp)$_3$); Ru (II) tris(1,10-phenanthroline) (Ru(phen)$_3$), tris(2,2'-bipyridine)ruthenium (II) chloride hexahydrate (Ru (bpy)$_3$); erythrosine B; fluorescein; fluorescein isothiocyanate (FITC); eosin; iridium (III) ((N-methyl-benzimidazol-2-yl)-7-(diethylamino)-coumarin)); indium (III) ((benzothiazol-2-yl)-7-(diethylamino)-coumarin))-2-(acetylacetonate); Lumogen dyes; Macroflex fluorescent red; Macrolex fluorescent yellow; Texas Red; rhodamine B; rhodamine 6G; sulfur rhodamine; m-cresol; thymol blue; xylenol blue; cresol red; chlorophenol blue; bromocresol green; bromcresol red; bromothymol blue; Cy2; a Cy3; a Cy5; a Cy5.5; Cy7; 4-nitrophenol; alizarin; phenolphthalein; o-cresolphthalein; chlorophenol red; calmagite; bromo-xylenol; phenol red; neutral red; nitrazine; 3,4,5,6-tetrabromphenolphtalein; congo red; fluorescein; eosin; 2',7'-dichlorofluorescein; 5(6)-carboxy-fluorecsein; carboxynaphtofluorescein; 8-hydroxypyrene-1,3,6-trisulfonic acid; semi-naphthorhodafluor; semi-naphthofluorescein; tris (4,7-diphenyl-1,10-phenanthroline) ruthenium (II) dichloride; (4,7-diphenyl-1,10-phenanthroline) ruthenium (II) tetraphenylboron; platinum (II) octaethylporphyin; dialkylcarbocyanine; dioctadecylcycloxacarbocyanine; fluorenylmethyloxycarbonyl chloride; 7-amino-4-methylcourmarin (Amc); green fluorescent protein (GFP); and derivatives or combinations thereof.

In some examples, the label moiety is a fluorescence label. In some examples, the fluorescence label is a small molecule. Such small molecules are known in the art.

In some examples, the label moiety has a structure represented by a formula:

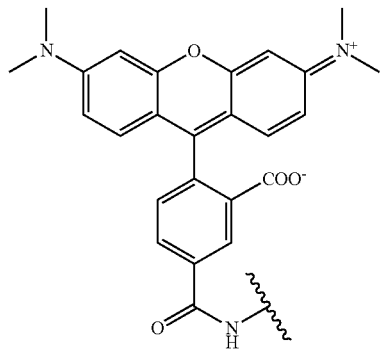

In the disclosed compounds $R^{11}$ or $R^{12}$ can be a substituted or unsubstituted, branched or straight chain $C_{1-20}$ alkyl, substituted or unsubstituted, branched or straight chain $OC_{1-20}$ alkyl, or a functionalized peptide side moiety of from two to 10 amino acid residues in length. As is shown herein, when $R^{11}$ or $R^{12}$ is a functionalized peptide, the potency of the disclosed cyclic peptides can be further boosted, generating a "lollipop" shaped molecule. Optimization of the tripeptidyl branch structure by medicinal chemistry approaches was envisioned to further increase the potency of C1-74-2. Importantly, through judicious choice of building blocks, the compound potency was increased without increasing its hydrophobicity. Second, this study provides another demonstration that relatively small, structurally constrained cyclic and bicyclic peptides (MW<2000) can recognize flat protein surfaces in an antibody-like manner and therefore serve as effective PPI inhibitors. Third, this work illustrates the importance of having access to both natural and unnatural building blocks (e.g., D-amino acids and β-amino acids) during library design and the power of chemical synthesis in generating such libraries.

Pharmaceutical Compositions

Also disclosed herein are pharmaceutical compositions comprising the disclosed compounds. That is, a pharmaceutical composition can be provided comprising a therapeutically effective amount of at least one disclosed compound. In some examples, a pharmaceutical composition can be provided comprising a prophylactically effective amount of at least one disclosed compound.

Also disclosed herein are pharmaceutical compositions comprising a pharmaceutically acceptable carrier and any of the compounds disclosed herein, wherein the compound is present in an effective amount. Also disclosed herein are neutraceutical compositions comprising a neutraceutically acceptable carrier and any of the compounds disclosed herein, wherein the compound is present in an effective amount.

In some examples of the compositions, the compound is present in an amount greater than about an amount selected from 5 mg, 10 mg, 25 mg, 50 mg, 100 mg, 150 mg, 200 mg, 250 mg, 300 mg, 400, mg, 500 mg, 750 mg, 1000 mg, 1,500 mg, or 2,000 mg.

The disclosed pharmaceutical compositions can further comprise one or more anticancer drugs.

Example anticancer drugs include 13-cis-Retinoic Acid, 2-Amino-6-Mercaptopurine, 2-CdA, 2-Chlorodeoxyadenosine, 5-fluorouracil, 6-Thioguanine, 6-Mercaptopurine, Accutane, Actinomycin-D, Adriamycin, Adrucil, Agrylin, Ala-Cort, Aldesleukin, Alemtuzumab, Alitretinoin, Alkaban-AQ, Alkeran, All-transretinoic acid, Alpha interferon, Altretamine, Amethopterin, Amifostine, Aminoglutethimide, Anagrelide, Anandron, Anastrozole, Arabinosylcytosine, Aranesp, Aredia, Arimidex, Aromasin, Arsenic trioxide, Asparaginase, ATRA, Avastin, BCG, BCNU, Bevacizumab, Bexarotene, Bicalutamide, BiCNU, Blenoxane, Bleomycin, Bortezomib, Busulfan, Busulfex, C225, Calcium Leucovorin, Campath, Camptosar, Camptothecin-11, Capecitabine, Carac, Carboplatin, Carmustine, Carmustine wafer, Casodex, CCNU, CDDP, CeeNU, Cerubidine, cetuximab, Chlorambucil, Cisplatin, Citrovorum Factor, Cladribine, Cortisone, Cosmegen, CPT-11, Cyclophosphamide, Cytadren, Cytarabine, Cytarabine liposomal, Cytosar-U, Cytoxan, Dacarbazine, Dactinomycin, Darbepoetin alfa, Daunomycin, Daunorubicin, Daunorubicin hydrochloride, Daunorubicin liposomal, DaunoXome, Decadron, Delta-Cortef, Deltasone, Denileukin diftitox, DepoCyt, Dexamethasone, Dexamethasone acetate, Dexamethasone sodium phosphate, Dexasone, Dexrazoxane, DHAD, DIC, Diodex, Docetaxel, Doxil, Doxorubicin, Doxorubicin liposomal, Droxia, DTIC, DTIC-Dome, Duralone, Efudex, Eligard, Ellence, Eloxatin, Elspar, Emcyt, Epirubicin, Epoetin alfa, Erbitux, Erwinia L-asparaginase, Estramustine, Ethyol, Etopophos, Etoposide, Etoposide phosphate, Eulexin, Evista, Exemestane, Fareston, Faslodex, Femara, Filgrastim, Floxuridine, Fludara, Fludarabine, Fluoroplex, Fluorouracil, Fluorouracil (cream), Fluoxymesterone, Flutamide, Folinic Acid, FUDR, Fulvestrant, G-CSF, Gefitinib, Gemcitabine, Gemtuzumab ozogamicin, Gemzar, Gleevec, Lupron, Lupron Depot, Matulane, Maxidex, Mechlorethamine, -Mechlorethamine Hydrochlorine, Medralone, Medrol, Megace, Megestrol, Megestrol Acetate, Melphalan, Mercaptopurine, Mesna, Mesnex, Methotrexate, Methotrexate Sodium, Methylprednisolone, Mylocel, Letrozole, Neosar, Neulasta, Neumega, Neupogen, Nilandron, Nilutamide, Nitrogen Mustard, Novaldex, Novantrone, Octreotide, Octreotide acetate, Oncospar, Oncovin, Ontak, Onxal, Oprevelkin, Orapred, Orasone, Oxaliplatin, Paclitaxel, Pamidronate, Panretin, Paraplatin, Pediapred, PEG Interferon, Pegaspargase, Pegfilgrastim, PEG-INTRON, PEG-L-asparaginase, Phenylalanine Mustard, Platinol, Platinol-AQ, Prednisolone, Prednisone, Prelone, Procarbazine, PROCRIT, Proleukin, Prolifeprospan 20 with Carmustine implant, Purinethol, Raloxifene, Rheumatrex, Rituxan, Rituximab, Roveron-A (interferon alfa-2a), Rubex, Rubidomycin hydrochloride, Sandostatin, Sandostatin LAR, Sargramostim, Solu-Cortef, Solu-Medrol, STI-571, Streptozocin, Tamoxifen, Targretin, Taxol, Taxotere, Temodar, Temozolomide, Teniposide, TESPA, Thalidomide, Thalomid, TheraCys, Thioguanine, Thioguanine Tabloid, Thiophosphoamide, Thioplex, Thiotepa, TICE, Toposar, Topotecan, Toremifene, Trastuzumab, Tretinoin, Trexall, Trisenox, TSPA, VCR, Velban, Velcade, VePesid, Vesanoid, Viadur, Vinblastine, Vinblastine Sulfate, Vincasar Pfs, Vincristine, Vinorelbine, Vinorelbine tartrate, VLB, VP-16, Vumon, Xeloda, Zanosar, Zevalin, Zinecard, Zoladex, Zoledronic acid, Zometa, Gliadel wafer, Glivec, GM-CSF, Goserelin, granulocyte colony stimulating factor, Halotestin, Herceptin, Hexadrol, Hexalen, Hexamethylmelamine, HMM, Hycamtin, Hydrea, Hydrocort Acetate, Hydrocortisone, Hydrocortisone sodium phosphate, Hydrocortisone sodium succinate, Hydrocortone phosphate, Hydroxyurea, Ibritumomab, Ibritumomab Tiuxetan, Idamycin, Idarubicin, Ifex, IFN-alpha, Ifosfamide, IL 2, IL-11, Imatinib mesylate, Imidazole Carboxamide, Interferon alfa, Interferon Alfa-2b (PEG conjugate), Interleukin 2, Interleukin-11, Intron A (interferon alfa-2b), Leucovorin, Leukeran, Leukine, Leuprolide, Leurocristine, Leustatin, Liposomal Ara-C, Liquid Pred, Lomustine, L-PAM, L-Sarcolysin, Meticorten, Mitomycin, Mitomycin-C, Mitoxantrone, M-Prednisol, MTC, MTX, Mustargen, Mustine, Mutamycin, Myleran, Iressa, Irinotecan, Isotretinoin, Kidrolase, Lanacort, L-asparaginase, and LCR.

In some examples, the pharmaceutical composition is administered to a subject. In some examples, the subject is a mammal, fish or bird. In some examples, the mammal is a primate. In some examples, the mammal is a human. In some examples, the human is a patient.

In some examples, the pharmaceutical composition is administered following identification of the mammal in need of treatment of cancer or inflammation or an autoimmune disease. In some examples, the pharmaceutical composition is administered following identification of the mammal in need of prevention of cancer or inflammation or an autoimmune disease. In some examples, the mammal has been diagnosed with a need for treatment of cancer or inflammation or an autoimmune disease prior to the administering step.

In some examples, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically or neutraceutically acceptable non-toxic bases or acids. When the compound is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically or neutraceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared thereof, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds disclosed herein, or pharmaceutically acceptable salts thereof, or neutraceutically acceptable salts thereof, can be combined as the active ingredient in intimate admixture with a pharmaceutical carrier or neutraceutical carrier according to conventional pharmaceutical compounding techniques or conventional neutraceutical compounding techniques. The carrier can take a wide variety of forms depending on the form of preparation desired for administration, e.g., oral or parenteral (including intravenous). Thus, the pharmaceutical compositions or neutraceutical compositions disclosed herein can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds disclosed herein, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions disclosed herein can include a pharmaceutically acceptable carrier and a compound or a pharmaceutically acceptable salt of the compounds disclosed herein. The compounds disclosed herein, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules can be used for oral dosage units whereby solid pharmaceutical carriers are employed. Optionally, tablets can be coated by standard aqueous or nonaqueous techniques A tablet containing any of the compositions disclosed herein can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions disclosed herein can comprise any of the compounds disclosed herein (or pharmaceutically or neutraceutically acceptable salts thereof) as an active ingredient, a pharmaceutically acceptable carrier or neutraceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. In some examples, a preservative can be included to prevent the detrimental growth of microorganisms.

Pharmaceutical compositions disclosed herein suitable for injectable use include sterile aqueous solutions or dispersions. Furthermore, the compositions can be in the form of sterile powders for the extemporaneous preparation of such sterile injectable solutions or dispersions. In some examples, the final injectable form can be sterile and can be effectively fluid for easy syringability. In some examples, the pharmaceutical compositions can be stable under the conditions of manufacture and storage; thus, they can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof Pharmaceutical compositions disclosed herein can be in a form suitable for topical use such as, for example, an aerosol, cream, ointment, lotion, dusting powder, mouth washes, gargles, and the like. In some examples, the compositions can be in a form suitable for use in transdermal devices. These formulations can be prepared, utilizing any of the compounds disclosed herein or pharmaceutically acceptable salts thereof, via conventional processing methods. As an example, a cream or ointment can be prepared by mixing hydrophilic material and water, together with about 5 wt % to about 10 wt % of the compound, to produce a cream or ointment having a desired consistency.

Pharmaceutical compositions disclosed herein can be in a form suitable for rectal administration wherein the carrier is a solid. In some examples, the mixture forms unit dose suppositories. Suitable carriers include cocoa butter and other materials commonly used in the art. The suppositories can be conveniently formed by first admixing the composition with the softened or melted carriers) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing any of the compounds disclosed herein, and/or pharmaceutically acceptable salts thereof, can also be prepared in powder or liquid concentrate form.

In the treatment of cancer, the dosage level of the active ingredient comprising the compound or compositions disclosed herein can be about 0.01 to 500 mg per kg patient body weight per day and can be administered in single or multiple doses. In some examples, he dosage level will be about 0.1 to about 250 mg/kg per day; such as 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0, or 5.0 to 50 mg/kg per day. For oral administration, the compositions can be, for example, in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage of the patient to be treated. The compound can be administered on a regimen of 1 to 4 times per day, such as, for example, once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease or infection undergoing therapy.

Also disclosed herein are methods for the manufacture of a medicament for treating cancer in mammals (e.g., humans) comprising combining one or more disclosed compounds, products, or compositions with a pharmaceutically acceptable carrier or diluent. In some examples, the method for manufacturing a medicament comprises combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

Compositions, Formulations and Methods of Administration

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, Remington's Pharmaceutical Science by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 100% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively, or an immunotherapeutic such as ipilimumab and bortezomib.

In certain examples, compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts or prodrugs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art.

The dosage ranges for the administration of the compositions are those large enough to produce the desired effect in which the symptoms or disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter indications. Dosage can vary, and can be administered in one or more dose administrations daily, for one or several days.

Also disclosed are pharmaceutical compositions that comprise a compound disclosed herein in combination with a pharmaceutically acceptable carrier. In some examples, the pharmaceutical compositions are adapted for oral, topical or parenteral administration. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Methods of Using the Compounds and Compositions

Also provided herein are methods of use of the compounds or compositions described herein. Also provided herein are methods for treating a disease or pathology in a subject in need thereof comprising administering to the subject an effective amount of any of the compounds or compositions described herein.

A very important application is for specific delivery of drugs such as anticancer drugs. The bicyclic peptides disclosed herein can be directed to a cancer-specific or overexpressed surface protein. Then an anticancer drug can be covalently or noncovaelently attached to the bicyclic peptide, e.g., at R, $R^1$, $R^{11}$, or $R^{12}$.

Also provided herein are methods of treating, preventing, or ameliorating cancer in a subject. The methods include administering to a subject an effective amount of one or more of the compounds or compositions described herein, or a pharmaceutically acceptable salt thereof. The compounds and compositions described herein or pharmaceutically acceptable salts thereof are useful for treating cancer in humans, e.g., pediatric and geriatric populations, and in animals, e.g., veterinary applications. The disclosed methods can optionally include identifying a patient who is or can be in need of treatment of a cancer. Examples of cancer types treatable by the compounds and compositions described herein include bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer. Further examples include cancer and/or tumors of the anus, bile duct, bone, bone marrow, bowel (including colon and rectum), eye, gall bladder, kidney, mouth, larynx, esophagus, stomach, testis, cervix, mesothelioma, neuroendocrine, penis, skin, spinal cord, thyroid, vagina, vulva, uterus, liver, muscle, blood cells (including lymphocytes and other immune system cells). Further examples of cancers treatable by the compounds and compositions described herein include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

In some examples, the cancer can be associated with TNF-α induced cell death.

The methods of treatment or prevention of cancer described herein can further include treatment with one or more additional agents (e.g., an anti-cancer agent or ionizing radiation). The one or more additional agents and the compounds and compositions or pharmaceutically acceptable salts thereof as described herein can be administered in any order, including simultaneous administration, as well as temporally spaced order of up to several days apart. The methods can also include more than a single administration of the one or more additional agents and/or the compounds and compositions or pharmaceutically acceptable salts thereof as described herein. The administration of the one or more additional agents and the compounds and compositions or pharmaceutically acceptable salts thereof as described herein can be by the same or different routes. When treating with one or more additional agents, the compounds and compositions or pharmaceutically acceptable salts thereof as described herein can be combined into a pharmaceutical composition that includes the one or more additional agents.

The methods and compounds as described herein are useful for both prophylactic and therapeutic treatment. As used herein the term treating or treatment includes prevention; delay in onset; diminution, eradication, or delay in exacerbation of signs or symptoms after onset; and prevention of relapse. For prophylactic use, a therapeutically effective amount of the compounds and compositions or pharmaceutically acceptable salts thereof as described herein are administered to a subject prior to onset (e.g., before obvious signs of cancer), during early onset (e.g., upon initial signs and symptoms of cancer), or after an established development of cancer. Prophylactic administration can occur for several days to years prior to the manifestation of symptoms of an infection. Prophylactic administration can be used, for example, in the chemopreventative treatment of subjects presenting precancerous lesions, those diagnosed with early stage malignancies, and for subgroups with susceptibilities (e.g., family, racial, and/or occupational) to particular cancers. Therapeutic treatment involves administering to a subject a therapeutically effective amount of the compounds and compositions or pharmaceutically acceptable salts thereof as described herein after cancer is diagnosed.

Also disclosed herein are methods of treating or preventing a disorder in a subject, such as a human, comprising administering to the subject an effective amount of a compound disclosed herein or a pharmaceutically acceptable salt thereof. In some examples, the subject is an animal, such as a human. In some examples, the subject is identified as having a need for treatment of the disorder. In some examples, the method treats a disorder. In some examples, the disorder is associated with TNF-α-induced cell death, such as dysfunctional regulation of TNF-α-induced cell death. In some examples, the disorder is associated with uncontrolled cellular proliferation, such as cancer. In some examples, the disorder is cancer. In some examples, the disorder is an inflammatory disorder. In some examples, the disorder is an autoimmune disorder, such as a disorder selected from rheumatoid arthritis, ankylosing spondylitis, Crohn's disease, ulcerative colitis, psoriasis, hidradenitis suppurativa, and refractory asthma.

In some examples, the subject has been diagnosed with the disorder prior to the administration step.

In some examples, the compound is administered in an amount between about 0.01 to 500 mg per kg patient body weight per day and can be administered in single or multiple doses. In some examples, the dosage level can be about 0.1 to about 250 mg/kg per day, such as about 0.05 to 100 mg/kg per day, or about 0.1 to 50 mg/kg per day. In some examples, the dosage can be 0.05 to 0.5, 0.5 to 5.0 or 5.0 to 50 mg/kg per day. In some examples, the dosage level can be 0.5 to 100 mg/kg per day. For oral administration, the compositions are can be provided in the form of tablets containing 1.0 to 1000 milligrams of the active ingredient, such as 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, such as once or twice per day. This dosing regimen can be adjusted to provide the optimal therapeutic response.

In some examples, the subject is a domesticated animal. In some examples, the domesticated animal is a domesticated fish, domesticated crustacean, or domesticated mollusk. In some examples, the domesticated animal is poultry. In some examples, the poultry is selected from chicken, turkey, duck, and goose. In some examples, the domesticated animal is livestock. In some examples, the livestock animal is selected from pig, cow, horse, goat, bison, and sheep.

In some examples, the method further comprises the step of identifying the animal in need of treatment or prevention of cancer. In some examples, the mammal has been diagnosed with a need for treatment and prevention of cancer prior to the administering step.

Protection Against TNF-α Induced Cell Death

Also disclosed herein are methods for protection against TNFα-induced cell death. The method can comprise administering an effective amount of a compound disclosed herein, a compound made by a method disclosed herein, a library disclosed herein, or a compound identified by methods disclosed herein to a subject identified as having a need for protection against TNFα-induced cell death.

In some examples, the amount is therapeutically effective. In some examples, the amount is prophylactically effective.

In some examples, the subject is a cell. In some examples, the subject is an animal. In some examples, the subject is a human.

Manufacture of a Medicament

Also disclosed herein are methods for the manufacture of a medicament for treating or preventing cancer comprising combining a therapeutically effective amount of a disclosed compound or product of a disclosed method with a pharmaceutically acceptable carrier or diluent.

Also disclosed herein are methods for manufacturing a medicament associated with treating or preventing cancer or the need to treat or prevent cancer with a pharmaceutically acceptable carrier or diluent.

In some examples, the medicament comprises a disclosed compound.

Kits

Also disclosed are kits that comprise a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

Also disclosed herein are kits comprising one or more of the disclosed compounds, and one or more of: a) at least one anticancer compound, b) instructions for treating a disorder associated with cancer, or c) instructions for treating cancer.

In some examples, the kit further comprises at least one agent, wherein the compound and the agent are co-formulated.

In some examples, the compound and the agent are co-packaged. The agent can be any agent as disclosed herein, known to have a side effect of cancer, an agent known to increase the risk of cancer, agent known to treat cancer in a subject.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using, and/or the disclosed compositions.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Materials and Reagents.

Certain materials, reagents and kits were obtained from specific vendors as indicated herein. Fmoc-protected amino acids were purchased from Advanced ChemTech (Louisville, KY), Peptides International (Louisville, KY), or Aapptec (Louisville, KY). O-Benzotriazole-N,N,N',N'-tetramethyluronium hexafluorophosphate (HBTU) and 1-hydroxybenzotriazole hydrate (HOBt) were from Aapptec. All solvents and other chemical reagents were obtained from Sigma-Aldrich, Fisher Scientific (Pittsburgh, Pa.), or VWR (West Chester, PA) and were used without further purification unless noted otherwise. N-(9-Fluorenylmethoxycarbonyloxy) succinimide (Fmoc-OSu) was from Advanced ChemTech. Phenyl isothiocyanate was purchased in 1-mL sealed ampoules from Sigma-Aldrich, and a freshly opened ampoule was used in each experiment. FITC, Texas Red-CoA, biotin-CoA and actinomycin D (A1410) were purchased from Sigma-Aldrich. Cell culture media, fetal bovine serum (FBS), penicillin-streptomycin, 0.25% trypsin-EDTA, Dulbecco's phosphate-buffered saline (DPBS; 2.67 mM potassium chloride, 1.47 mM potassium phosphate monobasic, 137 mM sodium chloride, 8.06 mM sodium phosphate dibasic) were purchased from Thermo Scientific (Rockford, IL).

Individual Peptide Synthesis and Labeling.

Bicyclic peptides were synthesized on 50 mg of Rink amide resin LS (0.2 mmol/g) using standard Fmoc chemistry. For bicyclic peptides C1 to C74, the N-terminal Fmoc group was removed with 20% piperidine in DMF (5+15 mM) and trimesic acid was coupled onto the N-terminal amine using HBTU as the coupling agent (5 equiv trimesic acid, 5 equiv HBTU, and 10 equiv DIPEA in 2 mL of DMF). The Alloc groups on the side chains of cyclization residues (Lys and Dap) were removed by treatment with $Pd(PPh_3)_4$ and phenylsilane (0.1 and 10 equiv, respectively) in anhydrous DCM (2×2 h). The peptide was cyclized by incubating the resin with a solution of PyBOP/HOBt/DIPEA (5, 5, and 10 equiv, respectively) in 2 mL of DMF for 3 h on a carousel shaker. For bicyclic peptides C1-74-1 to C1-74-6, the Mmt groups on the side chains of cyclization residues (Lys and Dap) were removed by treatment with 2% TFA in DCM (6×5 min). The peptide was cyclized as described above and the Alloc group on the side chain of dap at position-3 was removed by treatment with $Pd(PPh_3)_4$ as described above. Peptide synthesis was then continued at the side chain of dap using standard Fmoc/HBTU chemistry. FITC-labeled bicyclic peptides were synthesized using Mmt-protected Lys and dap as the cyclization residues and an Alloc-protected Lys at the C-terminus. After the synthesis of the linear peptide was complete, the Mmt groups on the side chains of Lys and dap were removed by 2% TFA and the peptides were cyclized with PyBOP as described above. The Alloc group on the side chain of the C-terminal Lys was removed by treatment with $Pd(PPh_3)_4$ as described above and the resulting resin (20 mg) was treated with a mixture containing 10 mg FITC and 100 µL of DIPEA in 500 µL of DMF for 2 h at room temperature. Peptide cleavage off the resin and side chain deprotection were carried out by treatment for 2 h with 3 mL of a cocktail containing 82.5:5:5:5:2.5 (v/v) TFA/thioanisole/water/phenol/ethanedithiol. After evaporation of the solvents, the crude peptide was triturated with cold ethyl ether (3×2 mL) and purified by reversed-phase HPLC on a C18 column (which was eluted with a linear gradient of 10-60% acetonitrile in doubly distilled water containing 0.05% TFA over 50 min). All peptides had ≥95% purity as judged by analytical HPLC. The authenticity of each peptide was confirmed by MALDI-TOF mass spectrometry.

Protein Expression, Purification and Labeling.

Recombinant TNFα containing an N-terminal 13-aa ybbR tag was expressed in *Escherichia coli*, purified, and specifically labeled with a biotin or Texas red at the ybbR tag as previously described (Lian, W.; et al., supra).

Fluorescence Anisotropy.

FITC-labeled bicyclic peptide (50 or 100 nM) were incubated with varying concentrations of TNFα (0-5 µM) in 30 mM HEPES, pH 7.4, 150 mM NaCl, and 2 mM magnesium acetate for 2 h. The FA values were measured on a Molecular Devices Spectramax M5 spectrofluorimeter, with excitation and emission wavelengths at 485 and 525 nm, respectively. Equilibrium dissociation constants (KD) were determined by plotting the FA values as a function of TNFα concentration and fitting the data to the following equation $$Y = \frac{\left(A_{min} + \left(A_{max} \times \frac{Q_b}{Q_f} - A_{min}\right)\left(\frac{(L+x+K_d) - \sqrt{((L+x+K_d)^2 - 4Lx)}}{2L}\right)\right)}{\left(1 + \left(\frac{Q_b}{Q_f} - 1\right)\left(\frac{(L+x+K_d) - \sqrt{((L+x+K_d)^2 - 4Lx)}}{2L}\right)\right)}$$

where Y is the measured anisotropy at a given TNFα concentration x; L is the bicyclic peptide concentration; $Q_b/Q_f$ is the correction fact for dye-protein interaction; $A_{max}$ is the maximum anisotropy when all the peptides are bound to TNFα, while $A_{min}$ is the minimum anisotropy. Competition experiments were performed by incubating 100 nM Asn-Asn-Asn-Lys(FITC)-labeled anticachexin C1 (Table 1), 2 µM of TNFα, and varying concentrations of unlabeled competitor peptide (0-20 µM) in the above buffer for 2 h. The FA values were plotted against the competitor peptide concentration to determine the $IC_{50}$ values.

Inhibition of TNFα-TNRF1.

Inhibition of TNFα-TNRF1 interaction by ELISA was carried out as previously described (Lian, W.; et al., supra).

Library Synthesis.

The bicyclic peptide library was synthesized on 0.3 g of TentaGel S $NH_2$ Resin (90 µm, 0.28 mmol/g), with all reactions performed at room temperature unless otherwise noted. The linker sequence (BBFRM) was first added to the resin by standard Fmoc chemistry. To spatially segregate the beads into outer and inner layers, the resin (after removal of the N-terminal Fmoc group) was washed with DMF (2×5 mL) and water (2×5 mL), and soaked in 5 mL of water overnight. The resin was quickly drained and suspended in a solution of Fmoc-OSu (0.5 eq) and DIPEA (0.5 eq) in 5 mL of 1:1 (v/v) DCM/diethyl ether. The mixture was incubated on a carousel shaker for 30 min and the beads were washed with 1:1 DCM/diethyl ether (3×5 mL) and DMF (8×5 mL). Next, allyloxycarbonyl-N-hydroxysuccinimide (Alloc-OSu, 3 equiv) and DIPEA (3 equiv) in 2 mL of 1:1 DCM/DMF was added to the resin. After 1 h, the reaction was repeated once to ensure complete reaction. The Fmoc group was removed from the surface peptides by treating with 5 mL of 20% (v/v) piperidine in DMF (5+15 min). The resin was next incubated in a mixture of Ac-Val-OH (5 equiv), Fmoc-Val-OH (0.1 equiv), HATU (5 equiv) and DIPEA (5 equiv) dissolved in 2 mL of DMF for 1 h. After removal of the N-terminal Fmoc group, properly protected Fmoc-amino acids (Scheme 2) and trimesic acid were sequentially coupled to the bead surface by standard Fmoc/HBTU chemistry, using 5 equiv of Fmoc-amino acid/trimesic acid, 5 equiv of HBTU, and 10 equiv of DIPEA in 4 mL of DMF (2 h). After the entire peptide sequence was synthesized, the Mmt groups on the side chains of cyclization residues (Lys and Dap) were removed by treatment with 5 mL of DCM containing 2% TFA for 5 min and the 2% TFA treatment was repeated five times. For peptide cyclization, the resin was incubated with a solution of PyBOP/HOBt/DIPEA (5, 5, 10 equiv, respectively) in 4 mL of DMF on a carousel shaker for 3 h. Next, the Alloc groups on the side chain of dap (position-3) and the N-terminus of inner linker sequence (BBFRM) were removed by treatment with $Pd(PPh_3)_4$ and phenylsilane (0.1 and 10 equiv, respectively) in 4 mL of anhydrous DCM for 2 h (twice). The random sequence was then coupled to the exposed amines by the split-and-pool method (Lam, K. S.; et al., "A new type of synthetic peptide library for identifying ligand-binding activity." *Nature* 1991, 354:82-84; Houghten, R. A.; et al., "Generation and use of synthetic peptide combinatorial libraries for basic research and drug discovery." *Nature* 1991, 354:84-86; Furka, A.; et al., "General method for rapid synthesis of multicomponent peptide mixtures." *Int. J. Pep. Prot. Res.* 1991, 37:487-493). Briefly, the resin was split into 20 equal aliquots (15 mg each) and placed into 20 different reaction vessels. A different X3 building block as specified in FIG. 4B was coupled to each aliquot by using 5 equiv of Fmoc-amino acid, 5 equiv of HATU, and 10 equiv of DIPEA in 0.5 mL of DMF (2 h). The coupling reaction was repeated once to ensure complete coupling at each step. The resin from the 20 reactors were pooled into a single vessel and treated with 20% piperidine to remove the N-terminal Fmoc group. After washing and drying, the resin was again split into 20 equal portions by weighing and a different X2 residue was coupled to each portion. This pool-and-split procedure was repeated again to couple the X1 residue. Finally, the resin was pooled and the N-terminal Fmoc group was removed by piperidine. Side-chain deprotection was carried out by incubating the resin in 10 mL of a modified reagent K [78.5:7.5:5:5:2.5:1:1 (v/v) TFA/phenol/water/thioanisole/ethanedithiol/anisole/triisopropylsilane] for 3 h. The resulting peptide library was washed with TFA (5 mL) and DCM (3×5 mL) and dried under vacuum before storage at −20° C.

Library Screening.

Library resin (20 mg, ~60,000 beads) was swollen in DCM, washed exhaustively with DMF, doubly distilled $H_2O$, and incubated in 1 mL of blocking buffer (137 mM NaCl, 2.7 mM KCl, 10 mM $Na_2HPO_4$, 1.8 mM $KH_2PO_4$, pH 7.4, 0.05% Tween 20 and 0.1% gelatin) containing 500 nM biotinylated TNFα at 4° C. overnight. After quickly washing with the blocking buffer (1 mL), the beads were suspended in 1 mL of the blocking buffer containing streptavidin-alkaline phosphatase (1 μg/mL final concentration) at 4° C. for 10 mM The beads were washed with 1 mL of the blocking buffer (3×) and 1 mL of a staining buffer (30 mM Tris, pH 8.5, 100 mM NaCl, 5 mM $MgCl_2$, 20 μM $ZnCl_2$) (3×). Next, 1 mL of the staining buffer and 100 μL of a BCIP stock solution (5 mg/mL) were added to the beads in a petri dish (exposed to air) and the mixture was incubated with gentle rocking. After 30 min, beads of the most intense turquoise color were manually removed with a micropipette under a dissecting microscope. After washing with DMF (3×1 mL), 8 M guanidine hydrochloride (1 mL with incubation for 30 min), dd$H_2O$ (3×1 mL), and PBS (1 mL), the beads were incubated overnight at 4° C. with 60 nM Texas red-labeled TNFα in the blocking buffer. The beads were examined under an Olympus SZX12 microscope equipped with a fluorescence illuminator (Olympus America, Center Valley, PA) and the most intensely fluorescent beads (19 beads) were manually isolated and subjected to sequencing analysis by partial Edman degradation-mass spectrometry (Thakkar, A.; et al., "Traceless capping agent for peptide sequencing by partial Edman degradation and mass spectrometry." *Anal. Chem.* 2006, 78:5935-5939).

MTT Assay.

WEHI-13VAR fibroblasts were purchased from American Type Culture Collection (ATCC). For maintenance, cells were grown in full medium as RPMI-1640 supplemented with 10% FBS and 1% Abs. For toxicity assay, cells were seeded in a 96-well plate at a density of $5\times10^3$ cells/well in 100 μL of RPMI-1640/1% Abs supplemented with 10% or 5% FBS and allowed to grow overnight. Varying concentrations of recombinant human TNFα (0-250 ng/mL) or commercial mouse TNFα were (0-100 μg/mL) were incubated with 10 μM peptide and actinomycin D (1 μg/mL) in 100 μL of corresponding growth medium for 1 h at 37° C. Next, the medium in the 96-well plate was removed and replaced with the above fresh mixture and the cells were incubated overnight. Next day, 10 μL of the 3-(4, 5-dimethylthiazolyl-2)-2, 5-diphenyltetrazolium bromide (MTT, final concentration 0.5 mg/ml) was added to each well and incubated at 37° C. for 3 h, following by the addition of 100 μL of the MTT solubilization solution. The plate was kept in the incubator overnight to let the formazan crystals to completely dissolve, and the absorbance at 570 nm was measured on a TECAN plate reader. The $LD_{50}$ was obtained as plotting the viability as a function of the TNFα concentration.

Immunoblotting.

WEHI-13VAR cells were cultured in full growth media (RPMI, 5% FBS, 1% Pen/Strep) in 12-well plates to reach 80% confluence. TNFα (5 ng/mL final concentration) and varying concentrations of peptide inhibitor (0-6 μM) were pre-incubated in 0.5 mL of the growth medium for 30 mM in the $CO_2$ incubator. The mixture was then used to treat the cells at 37° C. and in the presence of 5% $CO_2$. After 1.5 h, the solution was removed and the cells were washed with cold DPBS twice. The cells were lysed in 50 μL of lysis buffer (50 mM Tris, pH 7.4, 150 mM NaCl, 1% NP-40, and 5% glycerol) containing a protease inhibitor cocktail (Complete mini, Roche, product number 04693159001) and a phosphatase inhibitor cocktail (PhosSTOP, Roche, product number 04906845001). After incubation on ice for 30 mM, the cell lysate was centrifuged at 15,000 rpm for 10 min in a microcentrifuge. An equal volume of 2×SDS-loading buffer was added to the supernatant. The total cellular proteins were separated by SDS-PAGE and transferred electrophoretically to a nitrocellulose membrane, which was subsequently immunoblotted using anti-JNK and anti-p-JNK Thr183/Tyr185 antibodies (both from Santa Cruz Biotechnology). The same samples were also separated on a different SDS-PAGE gel and stained by Coomassie brilliant blue to check the sample loading in all lanes.

To examine the effect of C1-74-2 on NF-kB translocation, HT29 colon cancer cells were cultured in DMEM supplemented with 10% FBS and 1% Abs in a 6-well plate to reach 80% confluence. The cells were then starved in serum free DMEM supplemented with 1% Abs for 24 hr. Commercial mouse TNFα (1 ng/mL final concentration), and varying concentrations of peptide (0-50 μM) were pre-incubated in 1.5 mL of serum free DMEM for 1 h at 37° C. DMSO was kept at 0.2% (vol/vol) in all tubes. The mixture was then added to cells and incubated for 30 min. The cells were harvested immediately, and for each well all fractions were collected and combined. The separation of subcellular fractions was achieved by stepwise lysis of the cell pellet. The cells were first lysed in 100 μL of hypotonic buffer (20 mM Tris pH 8.0, 4 mM $MgCl_2$, 6 mM $CaCl_2$, 0.5 mM DTT) and 100 μL of dounce lysis buffer (0.6 M Sucrose, 0.2% NP-40, 0.5 mM DTT) supplemented with 1× protease inhibitor cocktail and 1× phosphatase inhibitor cocktail. After centrifugation at 1000 g for 5 min, the supernatant (cytoplasmic fraction) was carefully removed. The precipitates were resuspended in 100 μL of RIPA lysis buffer supplemented with 1× protease inhibitor cocktail and 1× phosphatase inhibitor cocktail, and lysed by sonication for 2 sec at 50% amplitude. The mixture were kept on ice for 30 min and then centrifuged at 15,000 rpm for 10 mM, and the resulting supernatant was the nuclear fraction. The protein concentration was measured by BCA kit, and all samples were adjusted to same concentration and added with equal volume of 2×SDS-loading buffer to boil for 10 mM. Equal amount of proteins (~30 μg for cytoplasmic fraction and 15 μg for nuclear fraction) were separated by SDS-PAGE and transferred electrophoretically to a nitrocellulose membrane, which was immunoblotted using anti-NF-κB antibody, and Histone H3 and GAPDH were used as loading control for nuclear and cytoplasmic fraction, respectively.

Luciferase Assay.

NF-κB reporter (Luc)-HEK293 cells30 (BPS Bioscience, San Diego, CA) were seeded at a density of 5,000 cells per well in Greiner white 96-well cell culture microplates in 50 μL of growth medium (DMEM+10% FBS+1% P/S). Cells were incubated overnight at 37° C. in the presence of 5%

$CO_2$. TNFα (5 ng/mL) and different concentrations of compound C1-74-2 (0-6 μM) were incubated for 1 h in 5 μL of growth medium (DMEM+5% FBS+1% P/S) at 37° C. in the presence of 5% $CO_2$. The growth medium in the plate was replaced with 50 μL of fresh medium (DMEM+5% FBS+1% P/S). The pre-incubated TNFα and peptide mixture (5 μL) was added into each well, with 5 μL of growth medium only added as the control. The cells were incubated at 37° C. with 5% $CO_2$ for 2 h. Fifty μL of ONE-Step™ Luciferase Assay reagent (BPS Bioscience, San Diego, CA) was added into each well. The whole plate was incubated at room temperature for 5 min and the luminescence generated was measured on a Tecan M1000 Pro microplate reader.

Serum Stability Test.

Diluted human serum (25%) was centrifuged at 15,000 rpm for 10 min, and the supernatant was collected. A peptide stock solution was diluted into the supernatant to a final concentration of 5 μM and incubated at 37° C. At various time points (0-8 h), 200-μL aliquots were withdrawn and mixed with 50 μL of 15% trichloroacetic acid and 200 μL of acetonitrile. After incubation at 4° C. overnight, the mixture was centrifuged at 15,000 rpm for 10 min in a microcentrifuge, and the supernatant was analyzed by reversed-phase HPLC equipped with an analytical C18 column (Waters). The amount of remaining intact peptide (%, relative that of time zero control) was determined by integrating the area underneath the peptide peak (monitored at 214 nm).

Results

Identification of Significant Binding Residues of Anticachexin C1 by Alanine Scan.

To identify residues significant for TNFα binding, each residue of anticachexin C1 (other than D-alanine at position-3, L-lysine at position-4, and L-2,3-diaminopropionic acid (Dap) at position-10) was individually replaced with an alanine (or D-alanine). To facilitate binding analysis by fluorescence anisotropy (FA), a tetrapeptide NNNK (SEQ ID NO: 1) was added to the C-terminus of each bicyclic peptide and the lysine side chain was labeled with fluorescein isothiocyanate (FITC) during solid-phase synthesis (Scheme 1). The three asparagine residues were added to improve the aqueous solubility of the bicyclic peptides. The bicyclic peptide was prepared by first synthesizing the full-length linear sequence on Rink amide resin using standard Fmoc/HBTU chemistry. The side chains of the two internal cyclization residues, L-lysine and Dap, were protected with monomethoxytrityl (Mmt) groups, whereas the C-terminal lysine was protected with an allyloxycarbonyl (Alloc) group. After removal of the N-terminal Fmoc group, a trimesic acid was coupled to the N-terminal amine using HBTU as the coupling agent. Next, the Mmt groups were selectively removed from the Lys and Dap side chains by 2% TFA and the peptide was cyclized by treatment with (benzotriazol-1-yloxy)tripyrrolidinophosphonium hexafluorophosphate (PyBOP). The Alloc group on the C-terminal lysine side chain was removed by treatment with $Pd(PPh_3)_4$ and the bicyclic peptide was selectively labeled at the C-terminal lysine by treating the resin with FITC. The NNNK (SEQ ID NO: 1)-tagged anticachexin C1 bound to TNFα with a KD value of 0.80 μM, similar to the previously reported value (0.45 μM) (Lian, W., et al., supra). The two tyrosine side chains (at positions 2 and 5) are most significant for TNFα binding, as their removal decreased the affinity by 14- and 12-fold, respectively (Table 1). Additionally, D-phenylalanine at position-6, D-lysine at position-8, and histidine at position-9 also contribute significantly to TNFα binding (4- to 7-fold reduction of affinity upon substitution of alanine or D-alanine). On the other hand, phenylglycine (Phg)-1 and glycine-7 play more minor roles in binding.

TABLE 1

Effect of Alanine Substitution on Anticachexin C1 Activity

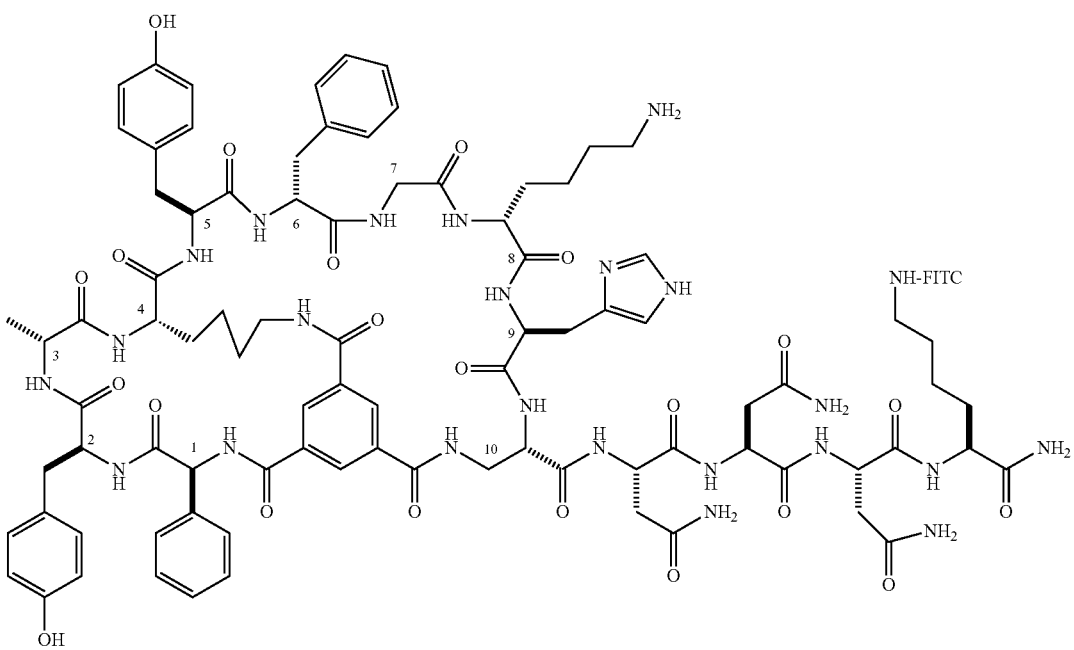

| Modification | $K_D$ (μM) | Fold of Affinity Reduction |
|---|---|---|
| C1 | 0.80 ± 0.30 | |
| Phg1 → Ala | 1.0 ± 0.3 | 1.2 |
| Tyr2 → Ala | 13 ± 6 | 14 |

TABLE 1-continued
| | | |
|---|---|---|
| Tyr5 → Ala | 11 ± 4 | 12 |
| D-Phe6 → D-Ala | 3.4 ± 1.0 | 4.0 |
| Gly7 → Ala | 1.2 ± 0.5 | 1.5 |
| D-Lys8 → D-Ala | 5.9 ± 2.0 | 7.0 |
| His9 → Ala | 4.4 ± 1.1 | 5.0 |
Scheme 1. Solid-Phase Synthesis of FITC-Labeled Anticachexin C1
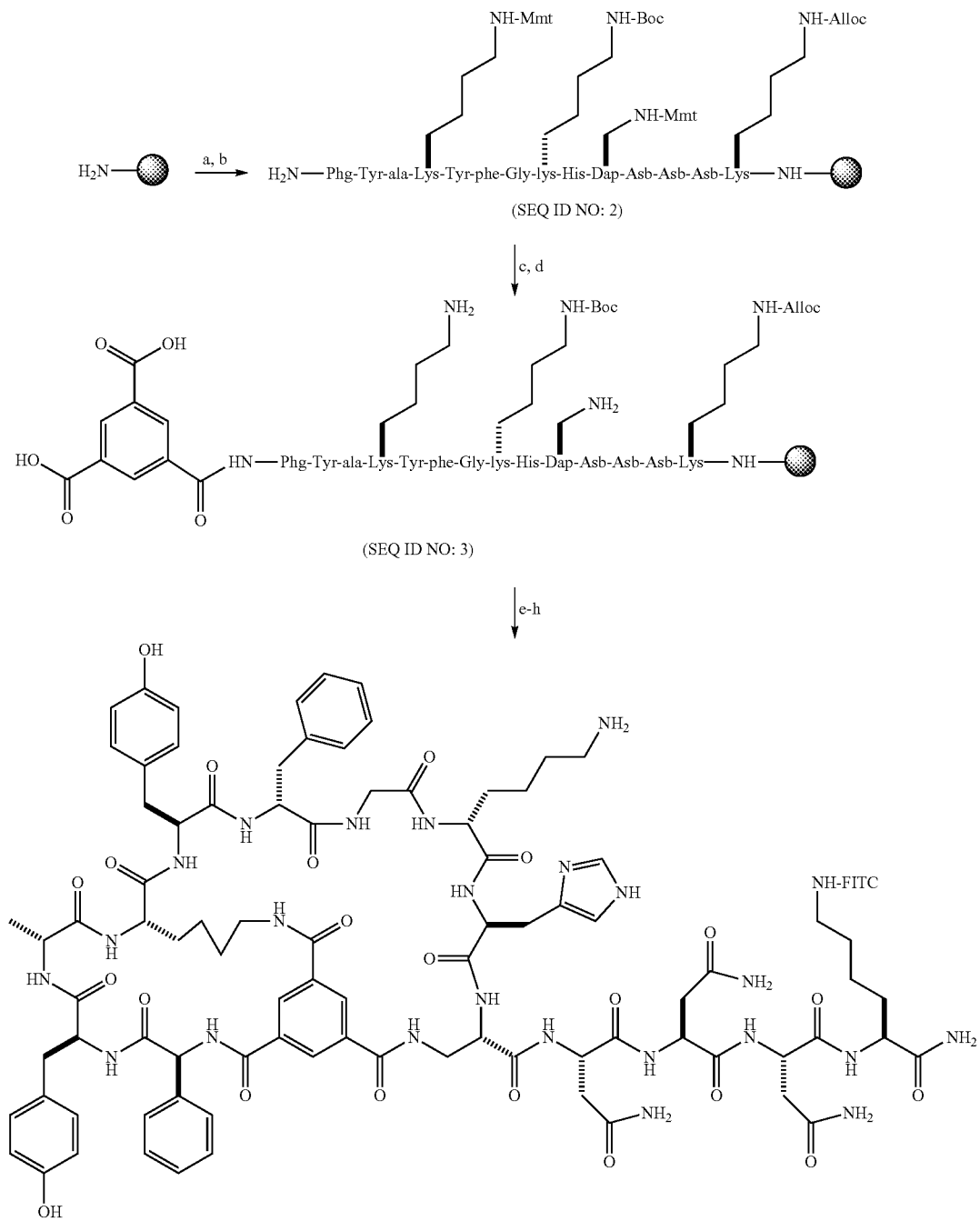
Reagents and conditions: (a) Standard Fmoc/HBTU chemistry; (b) piperidine; (c) trimesic acid, HBTU, DIPEA; (d) 2% TFA in /CH$_2$Cl$_2$; (e) PyBOP/HOBt/DIPEA; (f) Pd(PPh$_3$)$_4$; (g) FITC; and (h) reagent K.

Optimization of Position-1.

The optimization process was begun from the N-terminus (position-1) because of the apparently minor role played by Phg in TNFα binding. It was thought that Phg might be replaced with a variety of other amino acids without negatively impacting the TNFα binding affinity, e.g., hydrophilic residues which would improve the aqueous solubility of the resulting compounds. Surprisingly, removal (i.e., substitution of Gly) or replacement of the phenyl ring with any hydrophilic side chain (e.g., substitution of Ser, Thr, Asn, Asp, or Arg) greatly decreased TNFα binding (by ≥5-fold) (Table 2). On the other hand, replacement of the phenyl group with other hydrophobic side chains resulted in much smaller reduction in affinity, with n-butyl (norleucine) being ~2-fold better than the phenyl group (compare compounds C1 and C1-5). These results suggest that the side chain of residue-1 likely makes hydrophobic contacts with the TNFα surface. L-norleucine (Nle) was selected as the optimal residue for position-1 because, compared to Phg, Nle is also less susceptible to Cα epimerization during peptide synthesis.

Optimization of Positions-3 and 4.

Next, D-alanine was replaced at position-3 with amino acids containing small hydrophilic side chains (D-Ser, D-Thr, D-Asn, and L-Ser), to improve the aqueous solubility (Table 2, C1-11 through C1-17). These substitutions resulted in modest decreases in TNFα binding affinity, with D-Ser being least disruptive (~2-fold reduction). Inversion of the stereochemical configuration of D-alanine (to L-Ala or L-Ser) greatly reduced the binding affinity (C1-18 and C1-19, respectively). Therefore, a D-serine was temporarily selected as the "optimal" residue at position-3 to increase the solubility of the compounds during the subsequent optimization process. Next, the effect of ring size on the TNFα binding affinity was assessed by replacing the L-lysine at position-4 with L-ornithine (Orn) or L-Dap. Reduction of the ring size resulted in progressive decrease in binding affinity (Table 2, C1-20 and C1-21). Therefore, L-lysine was retained as the optimal moiety for peptide bicyclization.

TABLE 2

Activity of Anticachexin C1 Analogues with Modifications at Residues 1, 3, and 4

| Cmpd | $R^1$ | $R^3$ | n = | $K_D$ (μM) | Cmpd | $R^1$ | $R^3$ | n = | $K_D$ (μM) |
|---|---|---|---|---|---|---|---|---|---|
| C1 | Phg | D-Ala | 3 | 1.4 ± 0.4 | C1-11 | Nle | D-Ser | 3 | 1.5 ± 0.4 |
| C1-1 | Gly | D-Ala | 3 | 7.1 ± 4.6 | C1-12 | Nle | D-Asn | 3 | 1.4 ± 0.4 |
| C1-2 | Ala | D-Ala | 3 | 1.8 ± 0.6 | C1-13 | Val | D-Ser | 3 | 2.4 ± 1.1 |
| C1-3 | Abu | D-Ala | 3 | 2.0 ± 0.3 | C1-14 | Val | D-Thr | 3 | 2.9 ± 1.4 |
| C1-4 | Val | D-Ala | 3 | 1.7 ± 0.5 | C1-15 | Val | D-Asn | 3 | 3.2 ± 1.2 |
| C1-5 | Nle | D-Ala | 3 | 0.85 ± 0.08 | C1-16 | Leu | D-Asn | 3 | 2.7 ± 0.9 |
| C1-6 | Ser | D-Ala | 3 | 6.2 ± 2.5 | C1-17 | Phe | D-Asn | 3 | 2.2 ± 1.1 |
| C1-7 | Thr | D-Ala | 3 | 7.2 ± 4.4 | C1-18 | Nle | Ala | 3 | >20 |
| C1-8 | Asp | D-Ala | 3 | 7.0 ± 3.1 | C1-19 | Nle | Ser | 3 | 6.8 ± 4.2 |
| C1-9 | Asn | D-Ala | 3 | 7.9 ± 3.0 | C1-20 | Nle | D-Ser | 2 | 3.5 ± 0.7 |
| C1-10 | Arg | D-Ala | 3 | >10 | C1-21 | Nle | D-Ser | 0 | 5.9 ± 2.7 |

Optimization of Positions-2, 5, and 6.

Because Tyr-2 is significant for TNFα binding, relatively conservative substitutions of phenylalanine, 4-fluorophenylalanine (Fpa), 4-chlorophenylalanine (Cpa), 3,4-difluorophenylalanine ($F_2$pa), and histidine were made (Table 3, compounds C1-22 to C1-26). Phe and Fpa afforded similar binding affinity as Tyr, while the other substitutions caused significant loss of affinity. As expected, more drastic structural changes (e.g., substitution of Leu or Gln) also caused substantial reduction in binding affinity (C1-27 and C1-28). Based on these results, Tyr was kept at position-2 because of its better aqueous solubility than Phe or Fpa. Next, the moderately important D-Phe was replaced at position-6 with D-Tyr, D-His, D-Leu, or D-Gln and found that substitution of a D-His improved the binding affinity by ~2-fold (Table 3, compounds C1-29 to C1-32). D-His was thus selected as the optimal residue at position-6, because the imidazole ring offers additional benefits of aqueous solubility and metabolic stability. To test whether the Tyr at position-5 can be further improved, it was replaced with Fpa, Cpa, Trp, or 2-naphthylalanine (Nal) (Table 3, compounds C1-33 to C1-36) and discovered that substitution of Trp increased the TNFα binding affinity by 3-fold. Various combinations of substitutions at positions 2, 5, and 6 failed to further improve the potency of the compounds (C1-37 to C1-42). Thus, compound C1-35, which features optimal residues at positions 2, 5, and 6 (Tyr, Trp, and D-His, respectively), emerged as a relatively potent TNFα inhibitor ($K_D$=260 nM).

TABLE 3

Activity of Anticachexin C1 Analogues with Modifications at Residues 2, 5, and 6

| Cmpd | $R^2$ | $R^5$ | $R^6$ | $K_D$ (μM) | Cmpd | $R^2$ | $R^5$ | $R^6$ | $K_D$ (μM) |
|---|---|---|---|---|---|---|---|---|---|
| C1-11 | Tyr | Tyr | D-Phe | 1.5 ± 0.4 | C1-32 | Tyr | Tyr | D-Gln | 1.3 ± 0.3 |
| C1-22 | Phe | Tyr | D-Phe | 1.7 ± 0.7 | C1-33 | Tyr | Fpa | D-His | 0.76 ± 0.19 |
| C1-23 | Fpa | Tyr | D-Phe | 1.2 ± 0.5 | C1-34 | Tyr | Cpa | D-His | 1.6 ± 0.6 |
| C1-24 | Cpa | Tyr | D-Phe | 4.8 ± 1.0 | C1-35 | Tyr | Trp | D-His | 0.26 ± 0.08 |
| C1-25 | F2pa | Tyr | D-Phe | 5.4 ± 2.1 | C1-36 | Tyr | Nal | D-His | 1.3 ± 0.6 |
| C1-26 | His | Tyr | D-Phe | 2.1 ± 0.4 | C1-37 | Fpa | Tyr | D-Gln | 1.3 ± 0.7 |
| C1-27 | Leu | Tyr | D-Phe | 3.7 ± 0.4 | C1-38 | Fpa | Fpa | D-His | 2.1 ± 0.7 |
| C1-28 | Gln | Tyr | D-Phe | 4.3 ± 0.7 | C1-39 | Fpa | Tyr | D-His | 1.7 ± 0.7 |
| C1-29 | Tyr | Tyr | D-Tyr | 2.0 ± 0.4 | C1-40 | Cpa | Tyr | D-His | 4.1 ± 1.1 |
| C1-30 | Tyr | Tyr | D-His | 0.76 ± 0.16 | C1-41 | Trp | Tyr | D-His | 0.43 ± 0.15 |
| C1-31 | Tyr | Tyr | D-Leu | 2.5 ± 0.3 | C1-42 | Nal | Trp | D-His | >10 |

Optimization of Positions 7-9.

Substitution of sarcosine (Sar) or small L-amino acids [e.g., Ala and Ser] for Gly-7 had relatively minor effect (≤2-fold) and could either increase or decrease the TNFα binding affinity depending on whether Tyr or Trp was at position-5 (Table 1 and Table 4). Replacement with larger residues (e.g., Val and Leu), however, resulted in progressive loss of binding (by 3- to 6-fold), suggesting that a small L-amino acid at position-7 may be needed to accommodate a certain conformation of the bicycle. Either enhancing the positive charge at position 8 (by replacing the D-lysine with D-arginine) or removal of the charge (i.e., substitution of D-norleucine) almost completely abolished TNFα binding (Table 4, compounds C1-48 and C1-49). The side chain of D-lysine likely engages in a specific hydrogen bonding interaction(s) with a TNFα residue(s). Replacement of histidine at position-9 with a phenylalanine (compound C1-50) also greatly reduced the TNFα binding affinity (by ~30-fold). The Gly-D-Lys-His motif was therefore left unchanged at positions 7-9, because it contributes greatly to TNFα binding and aqueous solubility.

TABLE 4

Activity of Anticachexin C1 Analogues with Modifications at Residues 7-9

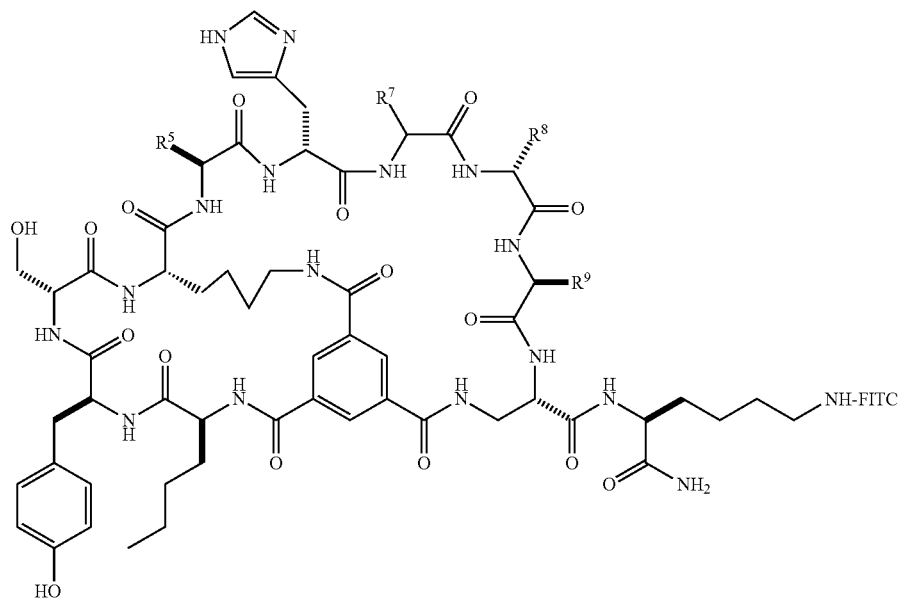

| Cmpd | R⁵ | R⁷ | R⁸ | R⁹ | $K_D$ (μM) |
| --- | --- | --- | --- | --- | --- |
| C1-30 | Tyr | Gly | D-Lys | His | 0.76 ± 0.16 |
| C1-35 | Trp | Gly | D-Lys | His | 0.26 ± 0.08 |
| C1-43 | Tyr | Sar | D-Lys | His | 0.33 ± 0.10 |
| C1-44 | Tyr | Ala | D-Lys | His | 0.32 ± 0.10 |
| C1-45 | Trp | Ser | D-Lys | His | 0.42 ± 0.13 |
| C1-46 | Trp | Val | D-Lys | His | 0.88 ± 0.22 |
| C1-47 | Trp | Leu | D-Lys | His | 1.7 ± 0.7 |
| C1-48 | Tyr | Gly | D-Arg | His | >10 |
| C1-49 | Tyr | Gly | D-Nle | His | >10 |
| C1-50 | Trp | Gly | D-Lys | Phe | 7.5 ± 2.2 |

Extension at C-Terminus (Position 11).

To improve the potency of C1-35, the possibility of extending the bicyclic structure at the C-terminus was explored and it was envisioned that a proper exocyclic appendage might engage in additional interactions with TNFα. Initially, a hydrophilic amino acid Asp, Asn, Arg, or 8-amino-3,6-dioxaoctanoic acid (miniPEG) was inserted between the C-terminal Dap and Lys(FITC), hoping to also improve the aqueous solubility of the compounds (Table 5, compounds C1-51 to C1-54). Surprisingly, insertion of any of the amino acids greatly decreased TNFα binding (by 3- to >40-fold), with Asn being least disruptive (3-fold reduction in affinity). Addition of hydrophobic amino acids (Phe, D-Phe, Nle, or Ile) also decreased the binding affinity to various degrees (C1-55 to C1-58). The notable exception was β-alanine (β-Ala) which, when inserted at position-11 (C1-59), substantially increased the TNFα binding affinity (by ~4-fold). It was hypothesized that the carboxamide group of β-Ala (and less effectively the free α-carboxamide of Lys(FITC) in C1-1 through C1-50) might interact with TNFα through a hydrogen bond(s). Note that in a previous peptide library, the bicyclic peptides were attached to the solid support through a β-Ala at the same position (Lian, W.; et al., supra). An Asn at this position provides a similar carboxamide group through its side chain (see Table 1 for structure). To test this notion and further improve the inhibitor potency, a series of compounds containing different β-amino acids at position-11 were synthesized and tested (Table 5, compounds C1-60 to C1-65). The results showed that, in general, β-amino acids at position-11 afford good TNFα binding activities, with the exception of 4-amino-1-methylpyrrole-3-carboxylic acid (C1-65) whose rigid planar structure might prevent the carboxamide group from hydrogen bonding with the yet unidentified residue(s) in TNFα. Since all side-chain modifications of β-Ala decreased TNFα binding, it was conclude that β-Ala is a beneficial residue at position-11 (Table 5, $K_D$=70 nM for C1-59).

TABLE 5

Effect of Residue 11 on TNFα Binding Affinity

| Cmpd | R^11 | $K_D$ (μM) | Cmpd | R^11 | $IC_{50}$ (μM) |
|---|---|---|---|---|---|
| C1-35 | Lys(FITC) | 0.26 ± 0.08 | C1-66 | β-Ala | 0.085 ± 0.050 |
| C1-51 | Asp-Lys(FITC) | 3.5 ± 1.8 | C1-67 | β-Ala-β-Ala | 1.5 ± 0.9 |
| C1-52 | Asn-Lys(FITC) | 0.79 ± 0.12 | C1-68 | β-Ala-Ala | 2.6 ± 1.1 |
| C1-53 | Arg-Lys(FITC) | >10 | C1-69 | β-Ala-Phe | 1.3 ± 1.1 |
| C1-54 | miniPEG-Lys(FITC) | 5.1 ± 1.2 | C1-70 | β-Ala-D-Phe | >10 |
| C1-55 | Phe-miniPEG-Lys(FITC) | 1.0 ± 0.4 | | | |
| C1-56 | D-Phe-miniPEG-Lys(FITC) | 0.63 ± 0.19 | | | |
| C1-57 | Ile-miniPEG-Lys(FITC) | 0.51 ± 0.29 | | | |
| C1-58 | Nle-miniPEG-Lys(FITC) | 1.4 ± 0.5 | | | |
| C1-59 | β-Ala-miniPEG-Lys(FITC) | 0.07 ± 0.01 | | | |
| C1-60 | [structure: N-ethyl Asn-miniPEG-Lys(FITC) derivative] | 0.38 ± 0.14 | | | |
| C1-61 | [structure: N-isopropyl Asn-miniPEG-Lys(FITC) derivative] | 0.42 ± 0.21 | | | |
| C1-62 | [structure: N-Me-β-homoAla-miniPEG-Lys(FITC)] | 0.21 ± 0.08 | C1-71 | [structure: N-Me-Val-amide] | 2.4 ± 1.3 |
| C1-63 | [structure: N-Me-aminocyclopentane carboxamide-miniPEG-Lys(FITC)] | 0.16 ± 0.15 | C1-72 | [structure: N-Me-aminocyclopentane carboxamide] | 0.11 ± 0.03 |

TABLE 5-continued

Effect of Residue 11 on TNFα Binding Affinity

| Cmpd | R¹¹ | $K_D$ (μM) | Cmpd | R¹¹ | $IC_{50}$ (μM) |
|---|---|---|---|---|---|
| C1-64 | (N-methylpiperidine-3-carbonyl)-NH-miniPEG-Lys(FITC) | 0.34 ± 0.23 | | | |
| C1-65 | (1-methyl-1H-pyrrole-3-carbonyl, 4-NH)-NH-miniPEG-Lys(FITC) | 1.9 ± 0.9 | C1-73 | 3-(methylamino)benzamide | 1.7 ± 0.7 |

Because of its high-throughput capability, FA analysis had been used to generate all of the SAR data described above. However, FA analysis is less reliable when the KD values become lower than the peptide ligand concentration used in the assay reactions (typically 50 nM), especially for TNFα-cyclic peptide interaction which, for yet unknown reasons, produced relatively small FA increases even when the fluorescent probe is fully bound (~2-fold). To confirm the SAR data obtained by FA analysis, some of the compounds in Table 5 (as well as new compounds) were resynthesized without the Lys(FITC) label and employed a more sensitive ELISA-based assay to determine the $IC_{50}$ values for inhibition of the TNFα-TNFR1 interaction. Briefly, biotinylated TNFα was immobilized onto a NeutrAvidin-coated surface. TNFR1 conjugated with horseradish peroxidase (HRP) (0.5 nM) was added along with different concentrations of a peptide inhibitor. After washing, the amount of bound TNFR1-HRP was quantitated by ELISA. Compound C1-66, which has the same core structure as C1-59, has an $IC_{50}$ value of 85 nM (Table 5). In agreement with the FA results, either extension at the C-terminus of β-Ala with another amino acid (C1-67 to C1-70) or side-chain modification of β-Ala (C1-71 to C1-73) decreased TNFα binding. As expected, reversion of D-Ser at position-3 back to D-Ala slightly increased the inhibitor potency, resulting in bicyclic peptide C1-74 as a potent TNFα inhibitor ($IC_{50}$=70 nM).

Extension at Position-3. Synthesis and Screening of a 2nd-Generation Library.

Finally, it was envisioned that "growing" C1-74 at one of its side chains might generate additional contacts with the TNFα surface and further increase the inhibitor potency. D-Ala at position 3 was selected for this purpose because the SAR data suggested that the D-Ala side chain points toward the solvent and tolerates a variety of substitutions. To identify a proper "appendage" that enhances C1-74 binding to TNFα, a second-generation bicyclic peptide library was constructed in which all library members contained the common core structure of C1-74, but different tripeptide sequences attached to the side chain of residue 3 (Scheme 2). The library was synthesized on 300 mg of 90-μm TentaGel resin (~900,000 beads) by modifying a previously reported procedure (Lian, W.; et al., supra). Briefly, the resin was spatially segregated into outer and inner layers and the N-terminal amine of a linker sequence (BBFRM (SEQ ID NO: 4) where B is β-Ala) was differentially protected with Fmoc and Alloc groups, respectively (Liu, R.; et al., "A novel peptide-based encoding system for "one-bead one-compound" peptidomimetic and small molecule combinatorial libraries." *J. Am. Chem. Soc.* 2002, 124:7678-7680;

Joo, S. H.; et al., "High-throughput sequence determination of cyclic peptide library members by partial Edman degradation/mass spectrometry." *J. Am. Chem. Soc.* 2006, 128: 13000-13009).

Figure 4A:
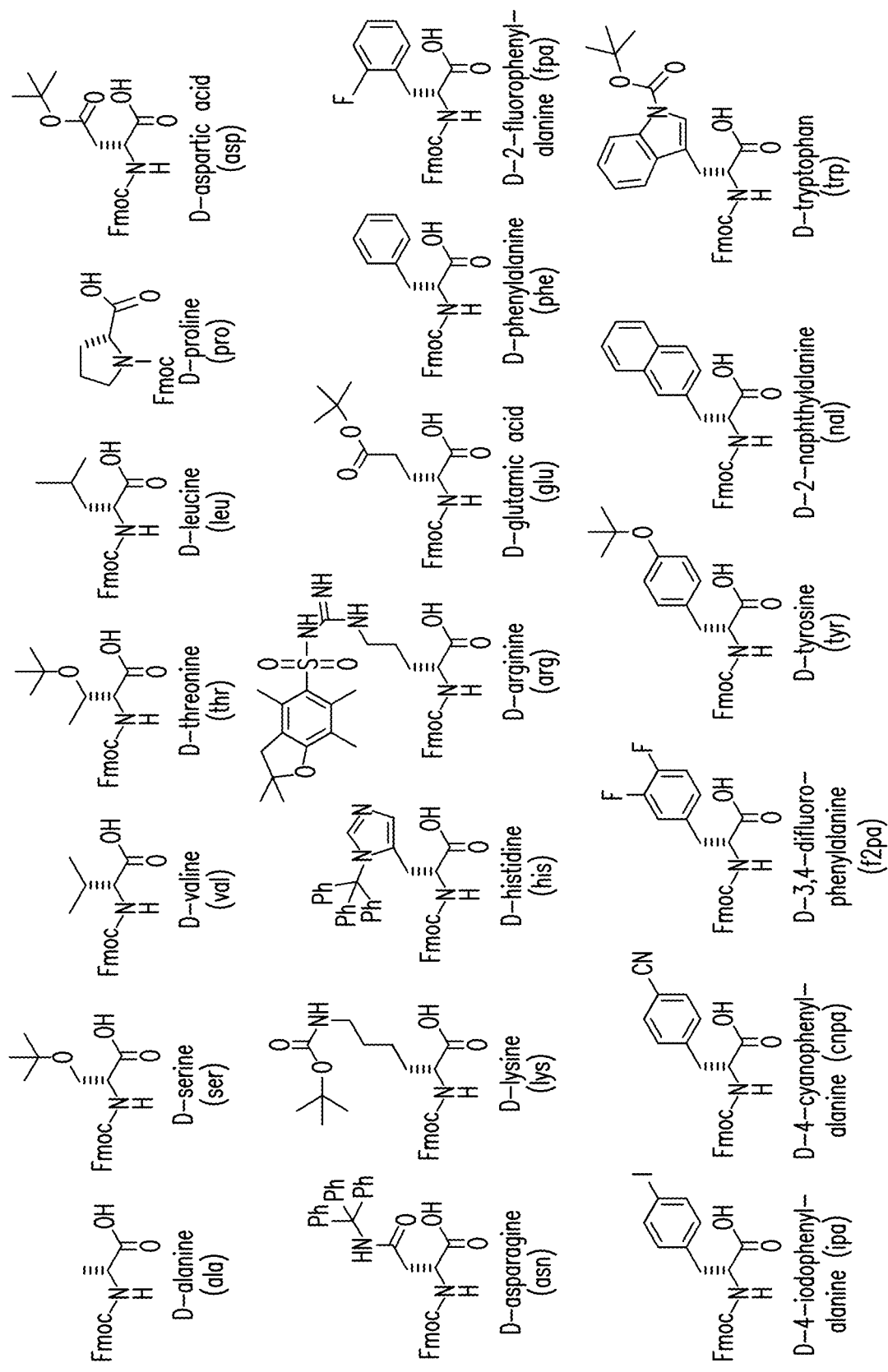
FIG. 4A shows structures of building blocks used at the X1 and X2 positions of the disclosed peptide library.
Figure 4B:
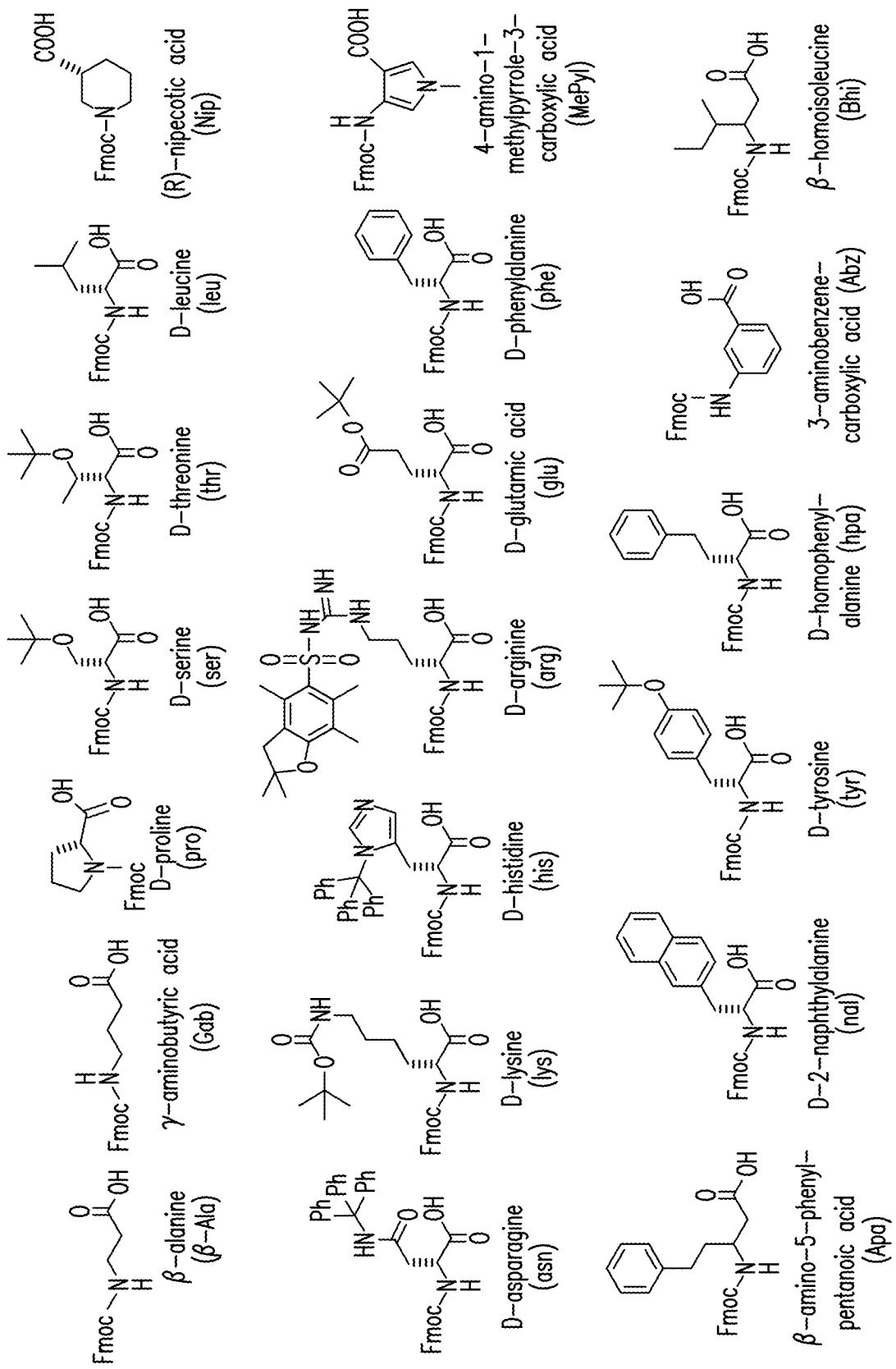
FIG. 4B shows structures of building blocks for the X3 position of the library.

Following removal of the Fmoc group from the surface layer, the ligand density in the surface layer was reduced by 50-fold (to improve the stringency of library screening) by capping the surface amines with a 49:1 (mol/mol) mixture of Ac-valine and Fmoc-Val (Chen, X.; et al., "On-bead screening of combinatorial libraries: Reduction of nonspecific binding by decreasing surface ligand density." *J. Comb. Chem.* 2009, 11:604-611). After removal of the Fmoc group again, a linear peptide corresponding to the sequence of C1-74 was synthesized on the surface layer, except that the D-alanine at position-3 was replaced with Alloc-protected (R)-2,3-diaminopropionic acid (dap). Next, the Mmt groups were removed under mild acidic conditions from the L-lysine and C-terminal L-Dap positions and the peptide was bicyclized by using trimesic acid as the scaffold (Lian, W.; et al., supra). Finally, the Alloc groups on dap at position-3 and the N-terminus of the linker sequence in the bead interior were removed by treatment with $Pd(PPh_3)_4$ and a random tripeptide sequence was coupled to the dap side chain as well as the inner linker sequence by the split-and-pool synthesis method (Lam, K. S.; et al., "A new type of synthetic peptide library for identifying ligand-binding activity." *Nature* 1991, 354:82-84; Houghten, R. A.; et al., "Generation and use of synthetic peptide combinatorial libraries for basic research and drug discovery." *Nature* 1991, 354:84-86; Furka, A.; et al., "General method for rapid synthesis of multicomponent peptide mixtures." *Int. J. Pep. Prot. Res.* 1991, 37:487-493). To maximize the proteolytic stability of the library compounds, D-α-amino acids (4-iodo-D-phenylalanine, 4-cyano-D-phenylalanine, 2-fluoro-D-phenylalanine (fpa), 3,4-difluoro-D-phenylalanine (f2pa), D-Trp, D-Asp, D-Val, D-Thr, D-Pro, D-Ser, D-Leu, D-Phe, D-Ala, D-Tyr, D-Nal, D-Glu, D-Asn, D-Lys, D-Arg, D-His) were used at the two N-terminal positions ($X^1$ and $X^2$) (FIG. 4A). At the C-terminal position ($X^3$), a structurally diverse set of unnatural amino acids (including 3-amino benzoic acid (Abz), L-β-homoisoleucine, (R)-nipecotic acid (Nip), 4-amino-1-methylpyrrole-3-carboxylic acid, γ-aminobutyric acid, β-Ala, D-homophenylalanine, D-Thr, D-Pro, D-Ser, D-Leu, D-Phe, (S)-3-amino-5-phenylpentanoic acid (apa), D-Tyr, D-Nal, D-Glu, D-Asn, D-Lys, D-Arg, and D-His) were employed (FIG. 4B). The resulting library has a theoretical diversity of 8,000 and each library bead carries a unique bicyclic peptide on its surface and the corresponding linear encoding tripeptide sequence in the interior.

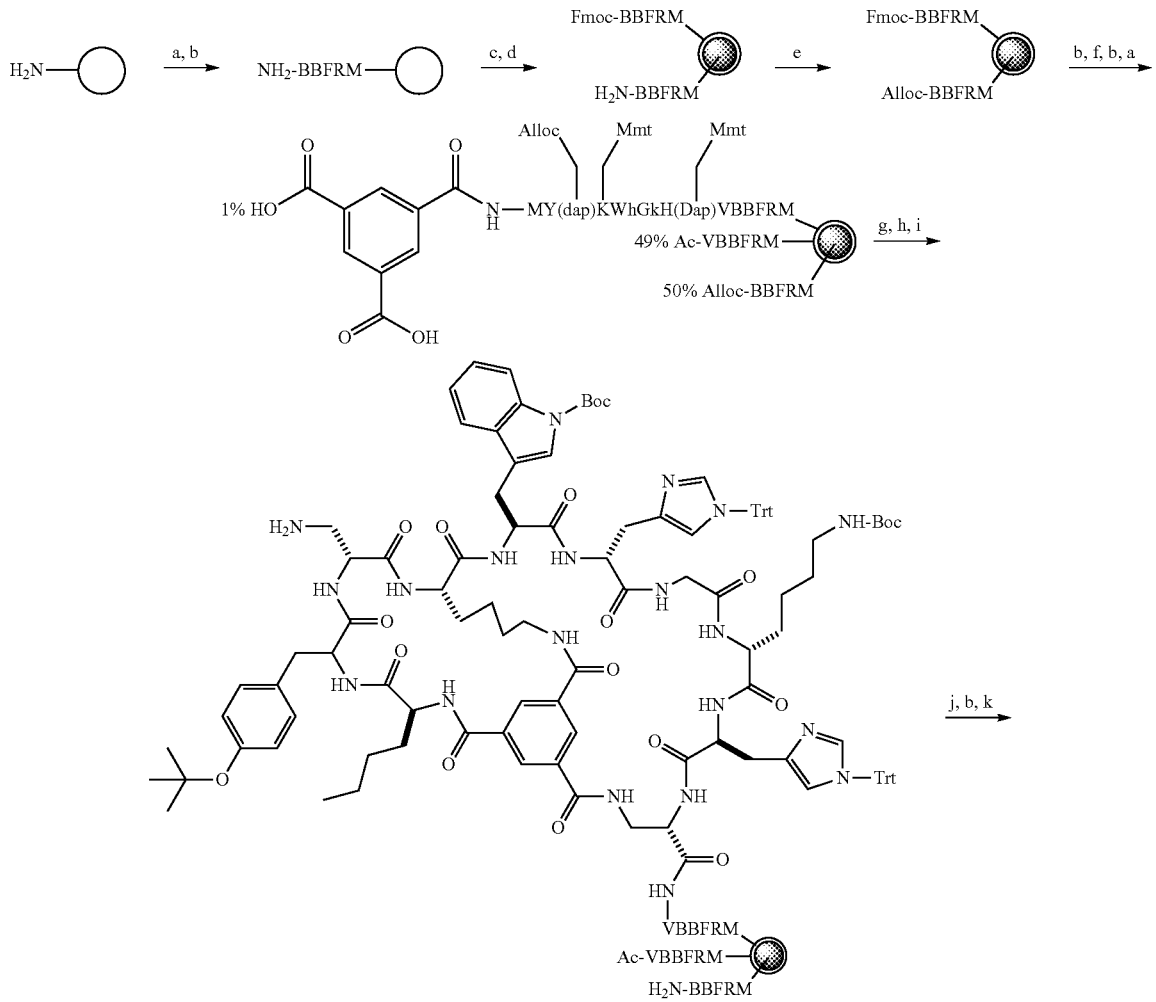

Scheme 2. Design and Synthesis of 2nd-Generation Bicyclic Peptide Library

-continued

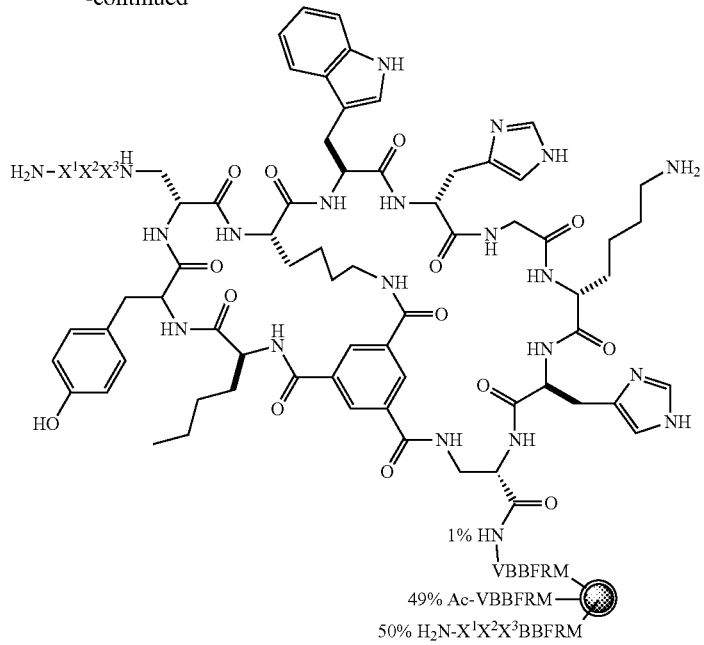

Reagents and conditions: (a) Standard Fmoc/HATU chemistry; (b) piperidine; (c) soak in water; (d) 0.5 equiv Fmoc-OSu in Et₂O/CH₂Cl₂; (e) Alloc-OSu; (f) 5 equiv Ac-Val-OH, 0.1 equiv Fmoc-Val-OH, HATU; (g) 2% TFA in /CH₂Cl₂; (h) PyBOP/HOBT/DIPEA; (i) Pd(PPh₃)₄; (j) split-and pool-synthesis; and (k) modified reagent K. B, β-alanine; k, D-lysine; h, D-histidine; M, methionine at the C-terminal position and noreucine at all other positions.

The library was subjected to two rounds of screening against TNFα. During the first round, ~20 mg of the library (~60,000 beads) was incubated with 500 nM biotinylated TNFα, followed by the addition of streptavidin-alkaline phosphatase and 5-bromo-4-chloro-3-indolyl phosphate (BCIP) (Lam, K. S.; et al., supra). The 38 most intensely turquoise colored beads were manually isolated, washed, and subjected to a second round of screening, during which the 38 beads were incubated with Texas-red labeled TNFα (60 nM). The 19 most intensely fluorescent beads were selected and the encoding peptides in their interior were sequenced by partial Edman degradation-mass spectrometry analysis (Thakkar, A.; et al., "Traceless capping agent for peptide sequencing by partial Edman degradation and mass spectrometry." Anal. Chem. 2006, 78:5935-5939), giving six complete sequences (Table 6, compounds C1-74-1 to C1-74-6). Four representative sequences [val-his-Nip (C1-74-2, FIG. 1A), f2pa-ala-phe (C1-74-3), and fpa-asn-apa (C1-74-4), and asp-asp-tyr (C1-74-5)] were individually resynthesized for further evaluation.

TABLE 6

Structures and Activities of Hits Identified from 2nd-Generation Library

| Cmpd | X¹-X²-X³ (R³) | IC₅₀ (nM) | LD₅₀ (ng/mL) |
|---|---|---|---|
| C1-74 | None (D-Ala at position-3) | 70 ± 20 | 3.2 ± 1.1 |
| C1-74-1 | 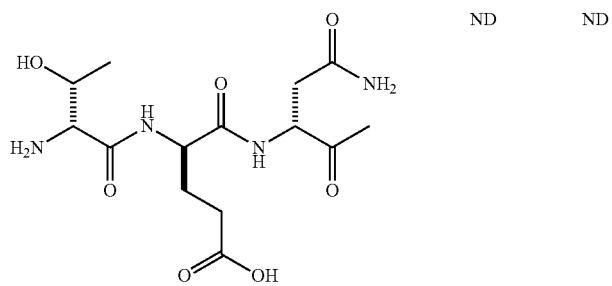 | ND | ND |

TABLE 6-continued

Structures and Activities of Hits Identified from 2$^{nd}$-Generation Library

| Cmpd | X$^1$-X$^2$-X$^3$ (R$^3$) | IC$_{50}$ (nM) | LD$_{50}$ (ng/mL) |
|---|---|---|---|
| C1-74-2 | | 12 ± 2 | 14 ± 6 |
| C1-74-3 | | 150 ± 43 | 2.6 ± 0.9 |
| C1-74-4 | | 30 ± 15 | 2.9 ± 1.0 |
| C1-74-5 | OH | 1350 ± 490 | 1.9 ± 0.6 |
| C1-74-6 | | ND | ND |

Figure 1B:
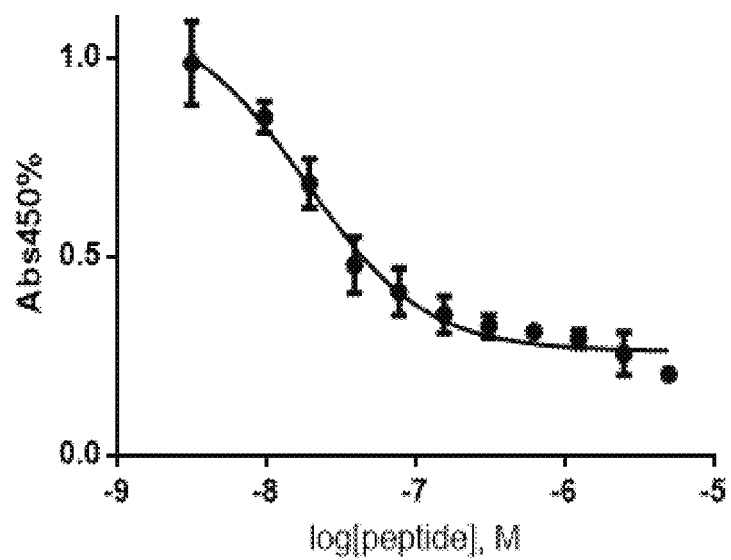
FIG. 1B is a graph showing inhibition of TNFα-TNFR1 interaction by C1-74-2 as monitored by ELISA. The remaining amount of bound TNFR1-HRP was plotted as a function of the C1-74-2 concentration.
Figure 5:
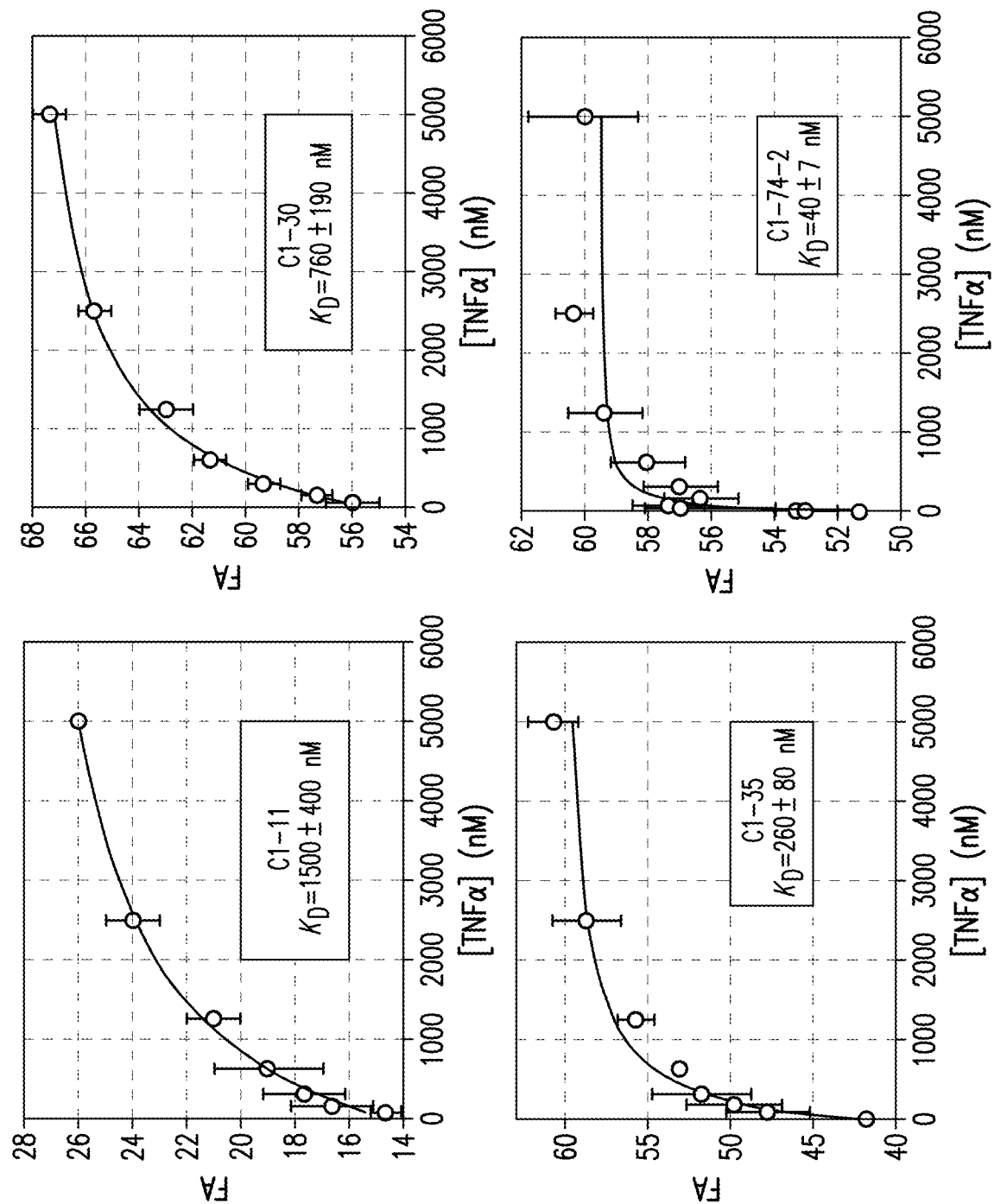
FIG. 5 is a group of graphs showing binding of representative anticachexin C1 analogs to TNFα as monitored by fluorescence anisotropy (FA). The error bars represent the standard deviation from three independent set of experiments.
Figure 6A:
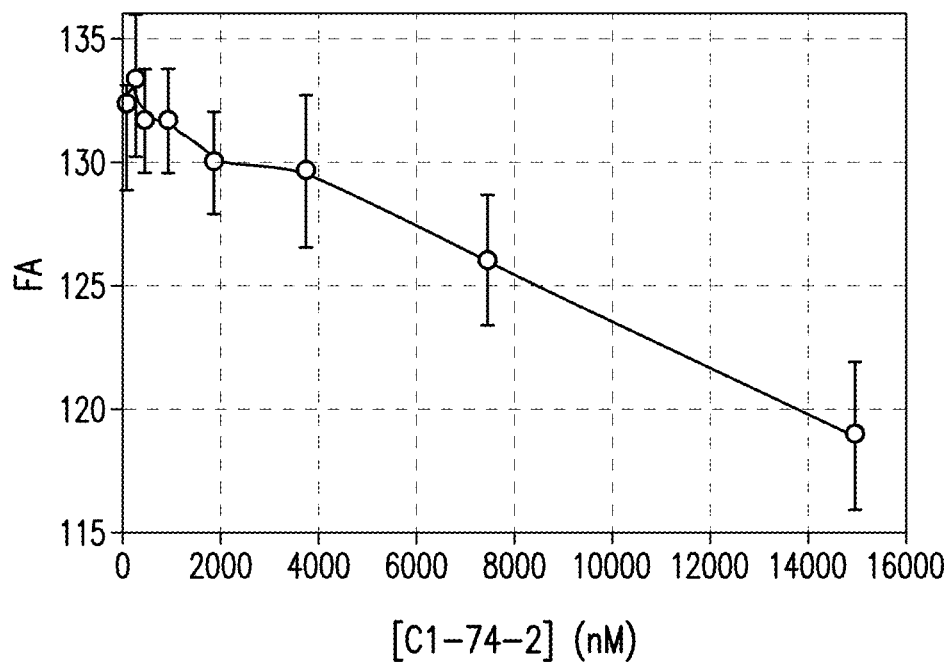
FIG. 6A is a graph showing the competition for binding to TNFα (2 μM) between C1-74-2 (0-15 μM) and C1-NNNK(FITC) (100 nM) as monitored by FA.
Figure 6B:
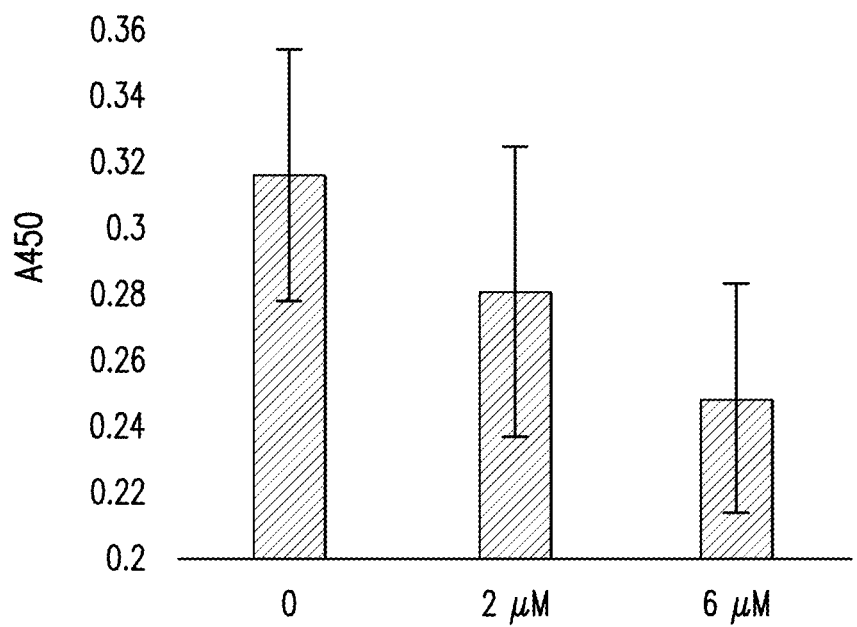
FIG. 6B is a graph showing binding of infliximab-HRP conjugate to immobilized TNFα in the absence and presence of C1-74-2 (0, 2, or 6 μM).

The four peptides were tested for inhibition of the TNFα-TNFR1 interaction by using the ELISA assay. Compound C1-74-2 was most potent, showing an IC$_{50}$ value of 12±2 nM (FIG. 1B), representing a ~6-fold improvement over C1-74 (Table 5). Compound C1-74-4 (IC$_{50}$=30 nM) is also more potent than the parent inhibitor, but only by ~2-fold. On the other hand, compounds C1-74-3 and C1-74-5 were actually less active than C1-74. These results demonstrate that extension of C1-74 at position-3 is effective for further increasing the TNFα binding affinity, but a properly appended structure is helpful for achieving such affinity enhancement. When labeled at the free N-terminal amine with 6-carboxyfluorescein and tested for binding to TNFα by FA, C-74-2 showed a KD value of 40±7 nM (FIG. 5). It also competed with FITC-labeled C1 for binding to TNFα in an FA based competition assay (FIG. 6A) and inhibited the binding of anti-TNFα antibody infliximab to a surface-immobilized TNFα in a concentration-dependent manner (FIG. 6B). Taken together, the above observations strongly suggest that C1-74-2 binds TNFα at a site that overlaps with the TNFR-binding site.

Biological Evaluation.

Figure 1C:
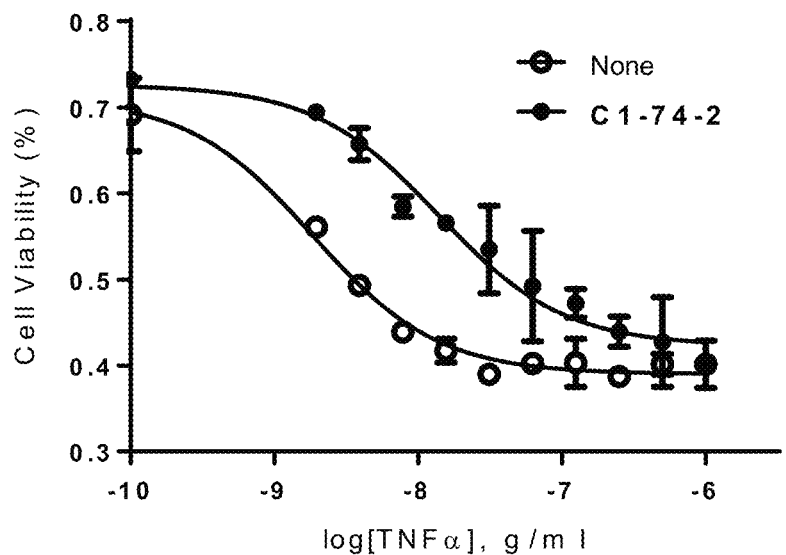
FIG. 1C shows data from a MTT assay of WEHI-13VAR cell viability as a function of TNFα concentration, in the absence and presence of 10 μM C1-74-2.
Figure 1D:
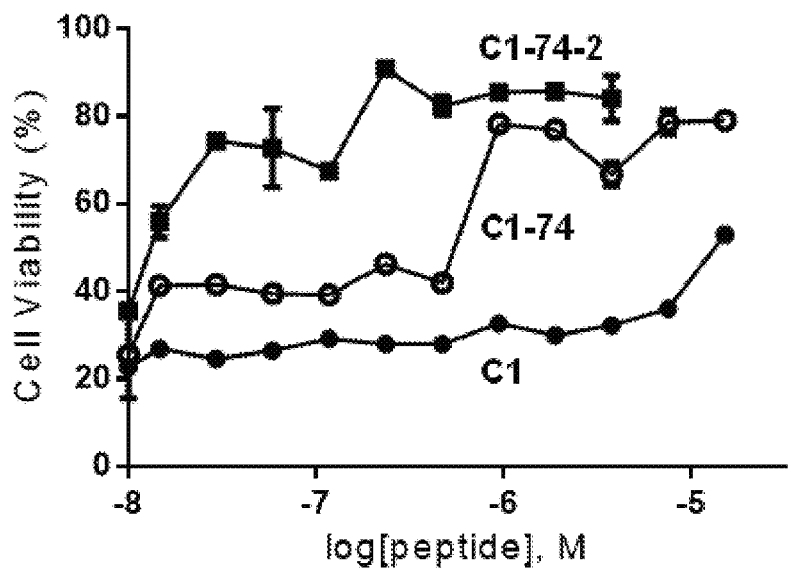
FIG. 1D shows data from a MTT assay of WEHI-13VAR cell viability as a function of peptide concentration, in the presence of 0.4 ng/mL TNFα. All measurements were performed in triplicates except for the C1 control in FIG. 1D, which was based on a single data set.

One of the biological functions of TNFα is to induce death signaling. Inhibitors against the TNFα-TNFR interaction are expected to protect cells against TNFα induced cell death. Therefore, anticachexin C1, C1-74, and C1-74-2 through C1-74-5 were compared for their ability to protect cultured WEHI-13VAR fibroblasts, which are highly sensitive to TNFα in the presence of actinomycin-D, against TNFα-induced cell death (Khabar, K. S. A.; et al., "WEHI-13VAR: A Stable and Sensitive Variant of WEHI 164 Clone 13 Fibrosarcoma for Tumor Necrosis Factor Bioassay." *Immunol. Lett.* 1995, 46:107-110). The cells were treated with a fixed concentration of peptides (10 µM) and varying concentrations of TNFα (0-1 µM), and the fraction of live cells was quantitated by the 3-(4,5-dimethylthiazol-2-yl)-2, 5-diphenyltetrazolium bromide (MTT) assay. In the absence of any peptide, TNFα showed an LD$_{50}$ value 1.9 ng/mL (FIG. 1C). Addition of 10 µM anticachexin C1-74-2 shifted the LD$_{50}$ value by almost an order of magnitude, to 14 ng/mL. In comparison, C1-74, C1-74-3, C1-74-4, and C1-74-5 were much less effective (LD$_{50}$ values 1.9-3.2 ng/mL, Table 6). The MTT assay was also conducted at a fixed concentration of TNFα (0.4 ng/mL) but varying concentrations of peptides (0-10 µM). All of the peptides protected the cells from TNFα-induced cell death in a concentration-dependent manner C1-74-2 was again most effective, showing an EC$_{50}$ value of ~50 nM and almost complete protection at ≥100 nM (FIG. 1D). In comparison, C1-74 had an EC$_{50}$ value of ~1 µM, whereas the parent compound (C1) showed significant protection only at ≥10 µM concentration.

Figure 2A:
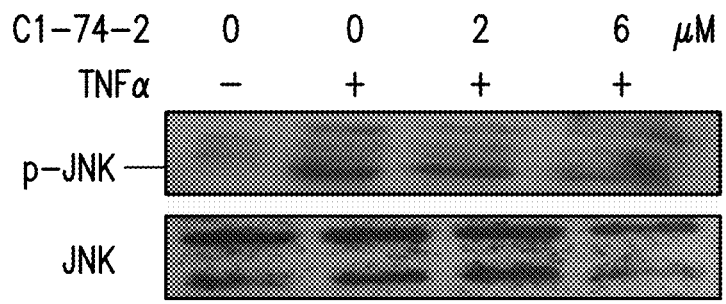
FIG. 2A is a picture from a Western blot showing the effect of C1-74-2 on TNFα-induced JNK phosphorylation in WEHI-13VAR cells.
Figure 2B:
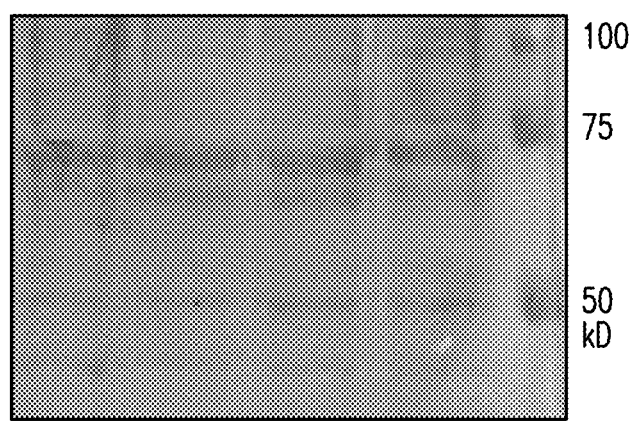
FIG. 2B is a picture from a Coomassie blue stain showing equal protein loading across all lanes.
Figure 2C:
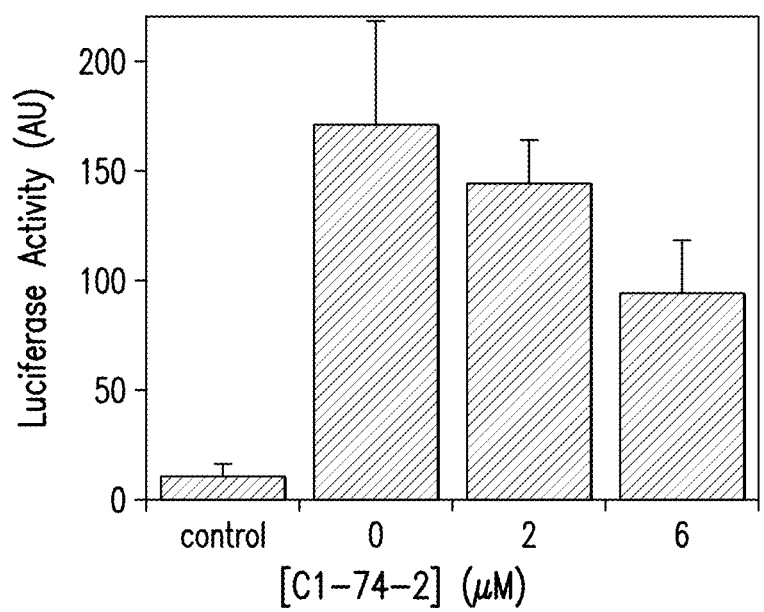
FIG. 2C is a graph showing the effect of C1-74-2 on TNFα-induced activation of NF-κB as monitored using a luciferase reporter assay in NF-κB reporter (Luc)-HEK 293 cells. Cells were treated with 5 ng/mL TNFα in the presence of varying concentrations of C1-74-2 (0-6 μM). Control, cells without TNFα or C1-74-2.

The effect of anticachexin C1-74-2 on other TNFα induced signaling pathways, namely the JNK and NF-κB pathways, were also assessed. WEHI-13VAR cells were treated with TNFα in the presence of increasing concentrations of C1-74-2 (0-20 µM) and the cell lysates were probed with antibodies specific for phosphorylated JNK (p-JNK) as well as total JNK. The p-JNK level, but not the total JNK protein level, decreased with the C1-74-2 concentration, demonstrating that C1-74-2 is indeed capable of inhibiting the activation of JNK signaling pathway (FIGS. 2A and 2B). To test the effect of C1-74-2 on the NF-κB pathway, a luciferase reporter assay, in which HEK293 cells were transfected with a luciferase gene under the control of NF-κB, was used (Takada, Y.; et al., "*Evodiamine* Abolishes Constitutive and Inducible NF-κB Activation by Inhibiting IκBα Kinase Activation, Thereby Suppressing NF-κB-regulated Antiapoptotic and Metastatic Gene Expression, Up-regulating Apoptosis, and Inhibiting Invasion." *J. Biol. Chem.* 2005, 280:17203-17212). Treatment of the NF-κB reporter (Luc)-HEK293 cells with 5 ng/mL TNFα alone caused a 17-fold increase in luciferase activity (FIG. 2C). However, pre-treatment of the cells with C1-74-2 (0-6 µM) followed by 5 ng/mL TNFα significantly decreased the magnitude of the TNFα-induced luciferase activity, with ~50% reduction of the luciferase activity at 6 µM C1-74-2.

Figure 3A:
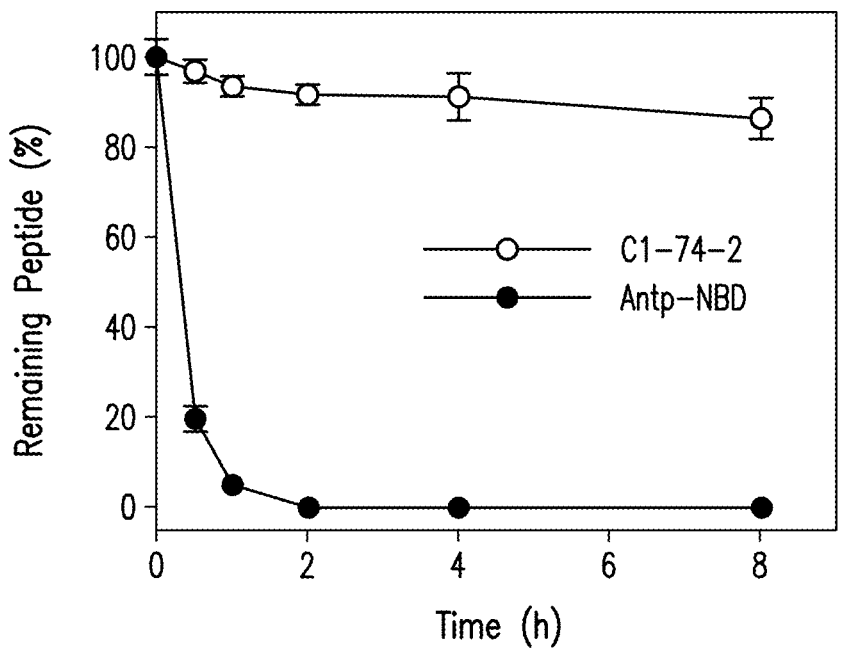
FIG. 3A is a graph showing serum stability of C1-74-2 and Antp-NBD.
Figure 3B:
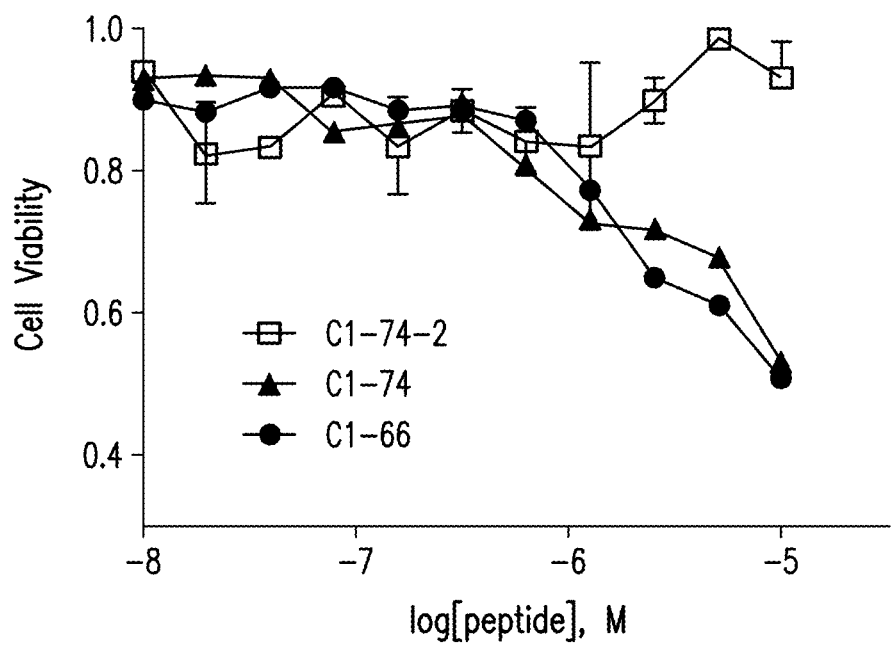
FIG. 3B is a graph showing the effect of C1-66, C1-74, and C1-74-2 on the viability of WEHI-13VAR cells as determined by the MTT assay (without TNFα). All measurements were performed in triplicates.

Compound C1-74-2 was tested for proteolytic stability and potential cytotoxicity. C1-74-2 is remarkably stable against proteolysis; incubation in human serum for 8 h at 37° C. resulted in only ~15% degradation (FIG. 3A). As a comparison, a linear peptide and clinical candidate, Antp-NBD (Habineza Ndikuyeze, G.; et al., "A Phase I Clinical Trial of Systemically Delivered NEMO Binding Domain Peptide in Dogs with Spontaneous Activated B-Cell like Diffuse Large B-Cell Lymphoma." *PLoS One* 2014, 9:e95404), was subjected to the same test. Antp-NBD showed a half-life of ~15 min and was completely degraded within 2 h. The exceptional stability of C1-74-2 is likely due to a combination of structural rigidity of the bicyclic system and the presence of multiple D-amino acids in the sequence. This property should facilitate its potential application as an oral drug for treatment of IBD. C1-74-2 is apparently non-toxic to mammalian cells. Treatment of WEHI-13VAR cells (without TNFα) with up to 25 µM C1-74-2 for up to 72 h did not result on significant reduction in cell viability (FIG. 3B). Interestingly, C1-74 and the structurally similar C1-66 (which contains a D-serine at position-3) both showed significant toxicity toward WEHI-13VAR cells at ≥1 µM concentration, likely due to off-target effects. Thus, the tripeptide appendage at position-3 not only improves the binding affinity to TNFα but also appears to block nonspecific binding to the off target(s).

Figure 7A:
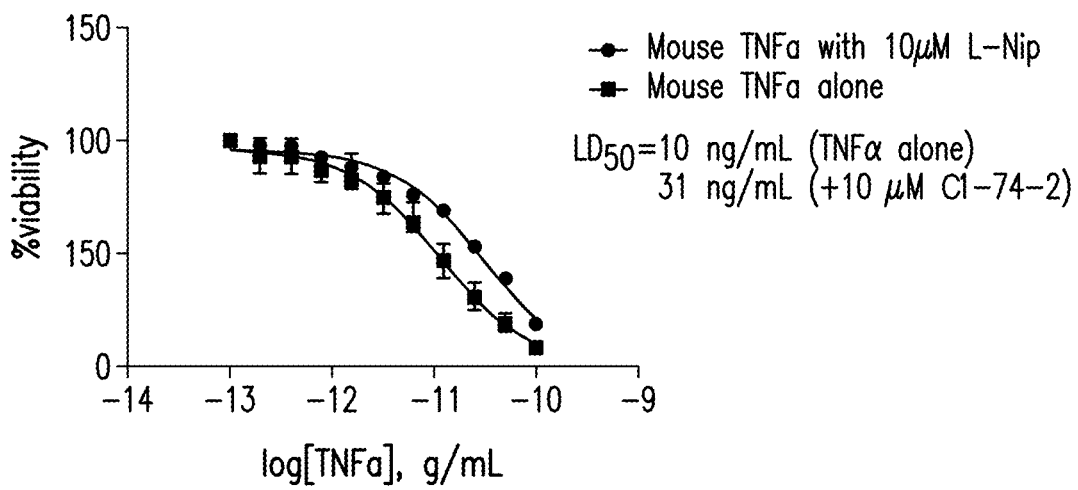
FIG. 7A-7C show cellular activity of C1-74-2.

TNFα inhibitor C1-74-2 was tested for its inhibitory activity against murine TNFα, a necessary step before testing C1-74-2 in a mouse model of inflammatory bowel disease. As shown in FIG. 7A, the addition of 10 µM C1-74-2 into the growth medium protected WEHI-13VAR fibroblasts from TNFα-induced cell death, shifting the LD$_{50}$ value of TNFα from 10 ng/mL (no inhibitor) to 31 ng/mL (with 10 µM C1-74-2). The magnitude of the shift was somewhat smaller than with human TNFα, suggesting that C1-74-2 binds to murine TNFα with lower affinity than human TNFα.

Figure 7B:
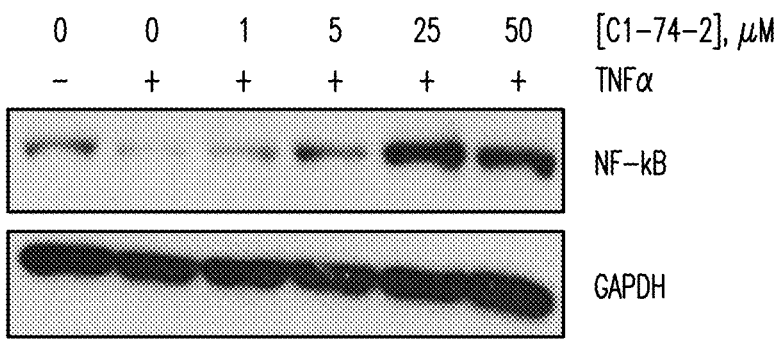
Figure 7C:
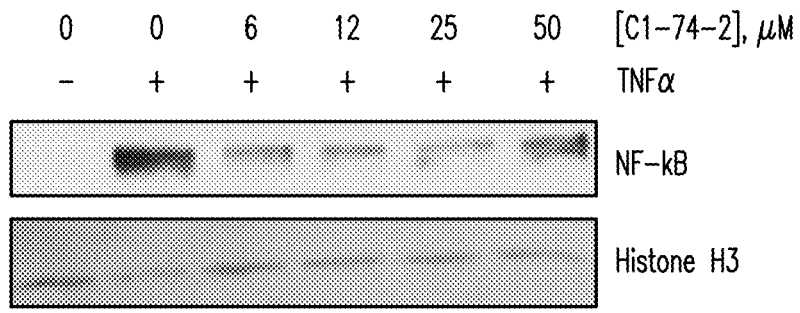

Next, C1-74-2 was tested for its ability to block TNFα-induced NF-kB nuclear translocation in HT29 cells. As shown in FIGS. 7B and 7C, treatment of HT29 cells with 1 ng/mL murine TNFα resulted in a decrease in the cytoplasmic concentration of NF-kB, with a concomitant increase in the nuclear concentration. However, addition of C1-74-2 dose-dependently blocked the nuclear translocation of NF-kB, as expected from its inhibition of TNFα function.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

The invention claimed is:

1. A compound comprising a bicyclic peptide of Formula 1:

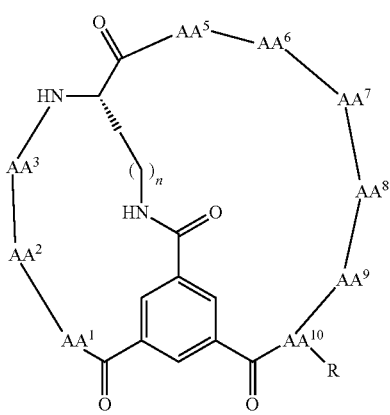

wherein $AA^1$-$AA^3$ and $AA^5$-$AA^{10}$ are independently amino acid residues;

wherein R is null, carboxylic acid, amide, or $C_{1-20}$ keto, ester, an amino acid, or a functionalized peptide moiety of from 2 to 10 amino acid residues in length;

wherein n is an integer from 1 to 6;

wherein at least two of $AA^1$, $AA^2$, $AA^3$, $AA^5$, $AA^7$, $AA^8$, $AA^9$, or $AA^{10}$ are independently amino acid residues with aryl or heteroaryl moieties; and $AA^6$ is an amino acid with a hydrophilic moiety.

2. The compound of claim 1, wherein $AA^1$ and $AA^2$ are independently amino acid residues comprising a hydrophobic moiety or an aryl moiety.

3. The compound of claim 2, wherein the hydrophobic moiety is phenyl, unsubstituted $C_{1-20}$ alkyl, or $C_{1-20}$ alkyl independently substituted with one or more OH, SH, $NH_2$ or $CO_2H$ groups.

4. The compound of claim 2, wherein the aryl moiety is unsubstituted phenyl or phenyl independently substituted with one or more halo, OH, SH, $NH_2$ or $CO_2H$ groups.

5. The compound of claim 2, wherein $AA^1$ is a residue of phenylglycine or norleucine.

6. The compound of claim 2, wherein $AA^2$ is a residue of tyrosine, 4-fluorophenylalanine, or phenylalanine.

7. The compound of claim 1, wherein $AA^3$ comprises a neutral or hydrophilic moiety.

8. The compound of claim 7, wherein the neutral or hydrophilic moiety is unsubstituted $C_{1-6}$ alkyl, or $C_{1-6}$ alkyl independently substituted with one or more halo, OH, SH, $CO_2H$, or $NH_2$ groups.

9. The compound of claim 1, wherein $AA^3$ is a residue of alanine, serine, threonine, or asparagine.

10. The compound of claim 1, wherein n is 3.

11. The compound of claim 1, wherein $AA^5$ is an amino acid residue comprising an aryl moiety.

12. The compound of claim 1, wherein $AA^5$ is a residue of tyrosine, 4-fluorophenylalanine, or tryptophan.

13. The compound of claim 1, wherein $AA^6$ is an amino acid residue comprising $CH_2$Imidazole, $C_{1-6}$ alkyl, unsubstituted phenyl, or phenyl independently substituted with one or more halo, OH, SH, $CO_2H$, or $NH_2$ groups.

14. The compound of claim 1, wherein $AA^7$ is an amino acid residue comprising unsubstituted $C_{1-2}$ alkyl, or $C_{1-2}$ alkyl independently substituted with one or more OH, SH, $NH_2$, or $CO_2H$ groups, or an amino acid residue wherein the side chain of the amino acid is H.

15. The compound of claim 1, wherein $AA^7$ is a residue of glycine, sarcosine, alanine, or serine.

16. The compound of claim 1, wherein $AA^8$ is an amino acid residue comprising a hydrophilic moiety.

17. The compound of claim 1, wherein $AA^8$ is an amino acid residue comprising unsubstituted $C_{1-6}$ alkyl or $C_{1-6}$ alkyl independently substituted with one or more halo, OH, SH, $CO_2H$, or $NH_2$ groups.

18. The compound of claim 1, wherein $AA^8$ is a lysine residue.

19. The compound of claim 1, wherein $AA^9$ is $CH_2$Imidazole, or $C_{1-6}$ alkyl, phenyl substituted with one or more halo, OH, SH, $CO_2H$, or $NH_2$ groups.

20. The compound of claim 1, wherein $AA^9$ is a histidine residue.

21. The compound of claim 1, wherein $AA^3$ comprises a side chain comprising a peptide of 2-8 amino acids in length.

22. The compound claim 21, wherein the peptide of 2-8 amino acids in length comprises a structure of:

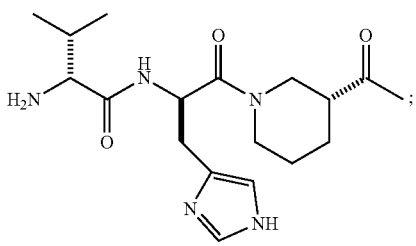

(i)

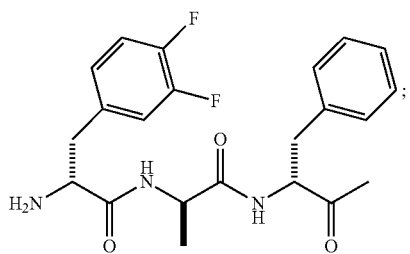

(ii)

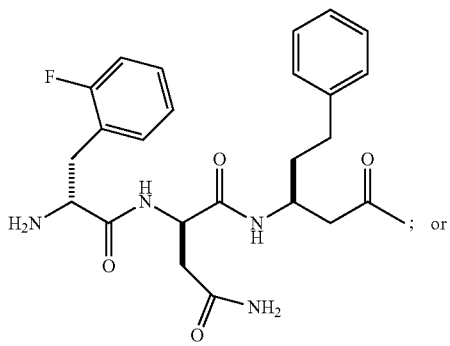

(iii)

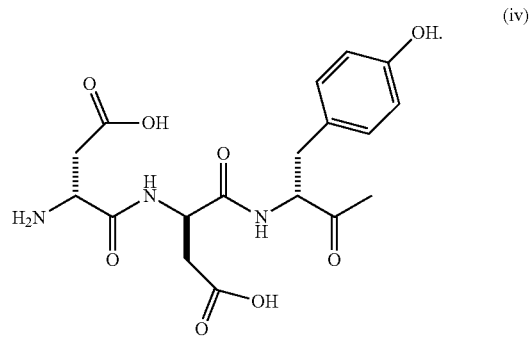

(iv)

23. A method for treatment of an inflammatory disorder, the method comprising the step of administering a therapeutically effective amount of the compound of claim 1 to a subject identified as having a need for treatment of the disorder.

24. A method for treatment of an autoimmune disorder, the method comprising the step of administering a therapeutically effective amount of the compound of claim 1 to a subject identified as having a need for treatment of the disorder.

25. A method for treatment of a disorder of uncontrolled cellular proliferation, the method comprising the step of administering a therapeutically effective amount of the compound of claim 1 to a subject identified as having a need for treatment of the disorder.

* * * * *

SEQUENCE LISTING

<160> NUMBER OF SEQ ID NOS: 4

<210> SEQ ID NO 1

-continued

```
<211> LENGTH: 4
<212> TYPE: PRT
<213> ORGANISM: Unknown
<220> FEATURE:
<223> OTHER INFORMATION: fluorescence anisotropy tetrapeptide
<220> FEATURE:
<221> NAME/KEY: MISC_FEATURE
<222> LOCATION: (4)..(4)
<223> OTHER INFORMATION: labeled with fluorescein isothiocyanate (FITC)

<400> SEQUENCE: 1

Asn Asn Asn Lys
1

<210> SEQ ID NO 2
<211> LENGTH: 14
<212> TYPE: PRT
<213> ORGANISM: Artificial Sequence
<220> FEATURE:
<223> OTHER INFORMATION: modified anticachexin C1
<220> FEATURE:
<221> NAME/KEY: MISC_FEATURE
<222> LOCATION: (1)..(1)
<223> OTHER INFORMATION: Xaa is phenylglycine
<220> FEATURE:
<221> NAME/KEY: MISC_FEATURE
<222> LOCATION: (3)..(3)
<223> OTHER INFORMATION: Xaa is D-alanine
<220> FEATURE:
<221> NAME/KEY: MISC_FEATURE
<222> LOCATION: (4)..(4)
<223> OTHER INFORMATION: modified with a monomethoxytrityl (Mmt) group
<220> FEATURE:
<221> NAME/KEY: MISC_FEATURE
<222> LOCATION: (6)..(6)
<223> OTHER INFORMATION: Xaa is D-phenylalanine
<220> FEATURE:
<221> NAME/KEY: MISC_FEATURE
<222> LOCATION: (8)..(8)
<223> OTHER INFORMATION: Xaa is D-Lysine
<220> FEATURE:
<221> NAME/KEY: MISC_FEATURE
<222> LOCATION: (8)..(8)
<223> OTHER INFORMATION: modified with a tert-butyl carbamate (Boc)
      group
<220> FEATURE:
<221> NAME/KEY: MISC_FEATURE
<222> LOCATION: (10)..(10)
<223> OTHER INFORMATION: Xaa is 2,3-diaminoproprionic acid
<220> FEATURE:
<221> NAME/KEY: MISC_FEATURE
<222> LOCATION: (10)..(10)
<223> OTHER INFORMATION: modified with a monomethoxytrityl (Mmt) group
<220> FEATURE:
<221> NAME/KEY: MISC_FEATURE
<222> LOCATION: (14)..(14)
<223> OTHER INFORMATION: modified with an allyloxycarbonyl (Alloc) group

<400> SEQUENCE: 2

Xaa Tyr Xaa Lys Tyr Xaa Gly Xaa His Xaa Asn Asn Asn Lys
1               5                   10

<210> SEQ ID NO 3
<211> LENGTH: 14
<212> TYPE: PRT
<213> ORGANISM: Artificial Sequence
<220> FEATURE:
<223> OTHER INFORMATION: modified anticachexin C1
<220> FEATURE:
<221> NAME/KEY: MISC_FEATURE
<222> LOCATION: (1)..(1)
<223> OTHER INFORMATION: Xaa is phenylglycine
<220> FEATURE:
<221> NAME/KEY: MISC_FEATURE
<222> LOCATION: (3)..(3)
```

```
<223> OTHER INFORMATION: Xaa is D-alanine
<220> FEATURE:
<221> NAME/KEY: MISC_FEATURE
<222> LOCATION: (6)..(6)
<223> OTHER INFORMATION: Xaa is D-phenylalanine
<220> FEATURE:
<221> NAME/KEY: MISC_FEATURE
<222> LOCATION: (8)..(8)
<223> OTHER INFORMATION: Xaa is D-Lysine
<220> FEATURE:
<221> NAME/KEY: MISC_FEATURE
<222> LOCATION: (8)..(8)
<223> OTHER INFORMATION: modified with a tert-butyl carbamate (Boc)
        group
<220> FEATURE:
<221> NAME/KEY: MISC_FEATURE
<222> LOCATION: (10)..(10)
<223> OTHER INFORMATION: Xaa is 2,3-diaminoproprionic acid
<220> FEATURE:
<221> NAME/KEY: MISC_FEATURE
<222> LOCATION: (14)..(14)
<223> OTHER INFORMATION: modified with an allyloxycarbonyl (Alloc) group

<400> SEQUENCE: 3

Xaa Tyr Xaa Lys Tyr Xaa Gly Xaa His Xaa Asn Asn Asn Lys
1               5                   10

<210> SEQ ID NO 4
<211> LENGTH: 5
<212> TYPE: PRT
<213> ORGANISM: Artificial Sequence
<220> FEATURE:
<223> OTHER INFORMATION: linker
<220> FEATURE:
<221> NAME/KEY: MISC_FEATURE
<222> LOCATION: (1)..(2)
<223> OTHER INFORMATION: Xaa is beta-alanine

<400> SEQUENCE: 4

Xaa Xaa Phe Arg Met
1               5
```